(12) United States Patent
Soll et al.

(10) Patent No.: US 10,240,158 B2
(45) Date of Patent: *Mar. 26, 2019

(54) COMPOSITIONS AND METHODS FOR MAKING SELENOCYSTEINE CONTAINING POLYPEPTIDES

(71) Applicant: Yale University, New Haven, CT (US)

(72) Inventors: Dieter Soll, Guilford, CT (US); Caroline Aldag, New Haven, CT (US); Michael Hohn, Scotch Plains, NJ (US); Corwin Miller, New Haven, CT (US)

(73) Assignee: Yale University, New Haven, CT (US)

( * ) Notice: Subject to any disclaimer, the term of this patent is extended or adjusted under 35 U.S.C. 154(b) by 65 days.

This patent is subject to a terminal disclaimer.

(21) Appl. No.: 15/202,194

(22) Filed: Jul. 5, 2016

(65) Prior Publication Data

US 2017/0002347 A1 Jan. 5, 2017

Related U.S. Application Data

(63) Continuation-in-part of application No. 14/131,382, filed as application No. PCT/US2012/046252 on Jul. 11, 2012, now Pat. No. 9,464,288.

(60) Provisional application No. 61/506,338, filed on Jul. 11, 2011.

(51) Int. Cl.
| | | |
|---|---|---|
| *C12N 15/11* | (2006.01) | |
| *C12N 15/67* | (2006.01) | |
| *C12N 15/70* | (2006.01) | |
| *C12P 21/02* | (2006.01) | |

(52) U.S. Cl.
CPC .............. *C12N 15/70* (2013.01); *C12N 15/11* (2013.01); *C12N 15/67* (2013.01); *C12P 21/02* (2013.01)

(58) Field of Classification Search
CPC . C12N 15/113; C12N 15/111; C12N 2320/50; C12N 15/11
See application file for complete search history.

(56) References Cited

U.S. PATENT DOCUMENTS

| 5,700,660 | A | 12/1997 | Leonard |
|---|---|---|---|
| 6,503,729 | B1 | 1/2003 | Bult |
| 7,723,069 | B2 | 5/2010 | Soll |
| 9,090,928 | B2 | 7/2015 | Park |
| 9,464,288 | B2 | 10/2016 | Soll |
| 2003/0082575 | A1 | 5/2003 | Schultz |
| 2014/0154744 | A1 | 6/2014 | Soll |

FOREIGN PATENT DOCUMENTS

| EP | 2246428 | 11/2010 |
|---|---|---|
| JP | 2008061538 | 3/2008 |
| WO | 0044906 | 8/2000 |
| WO | 2006107813 | 10/2006 |

OTHER PUBLICATIONS

Sherrer et al. Divergence of selenocysteine tRNA recognition by archaeal and eukaryotic O-phosphoseryl-tRNASec kinase Nucleic Acids Research, 2008, vol. 36, No. 6 1871-1880 (Year: 2008).*
Aldag, et al., "Rewiring translation for elongatiom-factor Tu-dependent selenocysteine incorporation", Angew Chem Int Ed., 52:1441-45 (2013).
Alessi, et al., "dentification of the sites in MAP kinase kinase-1 phosphorylated by p74raf-1", EMBO J., 13:1610-9 (1994).
Altschul et al., "Basic local alignment search tool", J. Mol. Biol., 215(3):403-410 (1990).
Ambrogelly, et al., "Cys-tRNACys formation and cysteine biosynthesis in methanogenlc archaea: two faces of the same problem?", Cell. Mol. LifeSci., 61:2437-45 (2004).
Arslan, et al., "Structurally modified firefly luciferase. Effects of amino acid substitution at position 286", Journal of the American Chemical Society, 119(45):10877-10887 (1997).
Bajaj, et al., "Mutagenesis-based definitions and probes of residue burial in proteins", PNAS, 102(45):16221-6 (2005).
Balch, et al., "Transport of coenzyme M (2-mercaptoethanesulfonic acid) in Methanobacterium ruminantium", J. Bacteriol., 137:264 (1979).
Basurko, et al., Phosphoserine aminotransferase, the second step-catalyzing enzyme for serine biosynthesis\, IUBMB Life, 48:525-9 (1999).
Bentin, et al., "Photoreactive bicyclic amino acids as substrates for mutant *Escherichia coli* phenylalanyl-tRNA synthetases", J. Biol. Chem. 279:19839-45 (2004).
Bernard, et al., "Positive-selection vectors using the F plasmid ccdB killer gene", Gene, 148:71-4 (1994).
Bilokapic, et al., "The unusual methanogenic seryl-tRNA synthetase recognizes tRNASer species from all three kingdoms of life", Eur. Journ. Biochemistry, 271(4):694-702 (2004).
Blight, et al., "Direct charging of tRNA(CUA) with pyrrolysine in vitro and in vivo", Nature, 431(7006):333-5 (2004).
Boyington, et al., "Crystal structure of formate dehydrogenase H: catalysis involving Mo, molybdopterin, selenocysteine, and an Fe4S4 cluster", Science, 275:1305-08 (1997).

(Continued)

*Primary Examiner* — Kagnew H Gebreyesus
(74) *Attorney, Agent, or Firm* — Pabst Patent Group LLP

(57) ABSTRACT

Non-naturally occurring tRNA$^{Sec}$ and methods of using them for recombinant expression of proteins engineered to include one or more selenocysteine residues are disclosed. The non-naturally occurring tRNA$^{Sec}$ can be used for recombinant manufacture of selenocysteine containing polypeptides encoded by mRNA without the requirement of an SECIS element. In some embodiments, selenocysteine containing polypeptides are manufactured by co-expressing a non-naturally occurring tRNA$^{Sec}$ a recombinant expression system, such as *E. coli*, with SerRS, EF-Tu, SelA, or PSTK and SepSecS, and an mRNA with at least one codon that recognizes the anticodon of the non-naturally occurring tRNA$^{Sec}$.

20 Claims, 19 Drawing Sheets

Specification includes a Sequence Listing.

(56) References Cited

OTHER PUBLICATIONS

Buchner, et al., "A method for increasing the yield of properly folded recombinant fusion proteins: single-chain Immunotoxins from renaturation of bacterial inclusion bodies", Anal. Biochem., 205:263-270 (1992).

Bunjun, et al., "A dual-specificity aminoacyl-tRNA synthetase in the deep-rooted eukaryote Giardia lamblia", PNAS, 97:12997-13002 (2000).

Calendar and Berg, "Purification and physical characterization of tyrosyl ribonucleic acid synthetases from *Escherichia coli* and Bacillus subtilis", Biochemistry, 5(5):1681-90 (1966a).

Calendar and Berg, "The catalytic properties of tyrosyl ribonucleic acid synthetases from *Escherichia coli* and Bacillus subtilis", Biochemistry, 5(5):1690-5 (1966b).

Carlson, et al., "Transfer RNAs that insert selenocysteine", Methods Enzymol, 347:24-39 (2002).

Chatterji and Pachter, "Large multiple organism gene finding by collapsed Gibbs sampling", J Comput Biol., 12(6):599-608 (2006).

Dale, et al.,"The affinity of elongation factor Tu for an aminoacyl-tRNA is modulated by the esterified amino acid", Biochemistry 43:6159-66 (2004).

Daly and Hearn, "Expression of heterologous proteins in Pichia pastoris: a useful experimental tool in protein engineering and production", J. Mol. Recognit., 18(2):119-38 (2005).

Das and Vothknecht, "Phenylalanyl-tRNA synthetase from the archaeon Methanobacterium thermoautotrophicum is an (alphabeta)2 heterotetrarneric protein", Biochlmie, 81(11):1037-9 (1999).

Datsenko, et al., "One-step inactivation of chromosomal genes in *Escherichia coli* K-12 using PCR products", PNAS, 97:6640-5 (2000).

Debinski, et al., "A wide range of human cancers express Interleukin 4 (IL4) receptors that can be targeted with chimeric toxin composed of IL4 and Pseudomonas exotoxin", J. Biol. Chem., 268:14065-14070 (1993).

Diamond, et al., "Dietary selenium affects methylation of the wobble nucleoside in the anticodon of selenocysteine tRNA([Ser]Sec).", J. Biol. Chem., 268:14215-23 (1993).

Eargle, et al., "Dynamics of Recognition between tRNA and elongation factor Tu", J Mol Biol., 377(5):1382-1405 (2008).

Ellman, et al., "Biosynthetic method for introducing unnatural amino acids site-specifically into proteins", Methods Enzymol., 202:301-36 (1991).

Engelhard, et al., "The insect tracheal system: a conduit for the systemic spread of Autographa californica M nuclear polyhedrosis virus", Proc. Natl. Acad. Sci. USA, 91:3224-3227(1994).

Fabrega, et al., "An aminoacyl tRNA synthetase whose sequence fits into neither of the two known classes", Nature, 411:110-4 (2001).

Fleer, et al.,"High-level secretion of correctly processed recombinant human interleukin-1 beta in Kluyveromyces lactis", Gene, 107:285-95 (1991).

Florens, et al., A proteomic view of the Plasmodium falciparum life cycle Nature, 419, 520-6 (2002).

Fromm, et al., "Expression of genes transferred into monocot and dicot plant cells by electroporation" Proc. Natl. Acad. Sci. USA, 82, 5824-8 (1985).

Fukunaga and Yokoyama, "Structural insights into the first step of RNA-dependent cysteine biosynthesis in archaea", Nat Struct Mol Biol., 14:272-9 (2007).

Giometti, et al., "Global analysis of a "simple" proteome: Methanococcus jannaschii", J. Chromatogr. B Anal. Technol. Biomed. Life Sci., 782(1-2):227-43 (2002).

Harrington, et al., "Formation of de novo centromeres and construction of first-generation human artificial microchromosomes", Nat Genet., 15:345-355 (1997).

Hitzeman, et al., "Isolation and characterization of the yeast 3-phosphoglycerokinase gene (PGK) by an immunological screening technique", J. Biol. Chem., 255:12073-80 (1980).

Hofer, et al., "An engineered selenocysteine defines a unique class of antibody derivatives",PNAS, 105(34):12451-6 (2008).

Hohn, et al., "Emergence of the universal genetic code imprinted in an RNA record", PNAS,103(48):18095-100 (2006)

Hohsaka, et al., "Five-base codons for incorporation of nonnatural amino acids into proteins", Nucleic Acids Res., 29:3646-51 (2001).

Holland and Holland, "Isolation and identification of yeast messenger ribonucleic acids coding for enolase, glyceraldehyde-3-phosphate dehydrogenase, and phosphoglycerate kinase", Biochem., 17:4900-7 (1978).

Ibba, et al., "The adaptor hypothesis revisited", Trends Biochem. Sci., 25:311-6 (2000).

Jacob, et al., "Sulfur and selenium: the role of oxidation state in protein structure and function", Angew. Chem. Int. Ed. Engl., 42:4742-58 (2003).

Jansen, et al., "Drag&Drop cloning in yeast", Gene, 344:43-51 (2005).

Johansson, et al., "Selenocysteine in proteins-properties and biotechnological use", Biochim Biophys Acta., 1726:1-13 (2005).

Kamtekar, et al., "Toward understanding phosphoseryl-tRNACys formation: the crystal structure of Methanococcus maripaludis phosphoseryl-tRNA synthetase", PNAS, 104(8):2620-5 (2007).

Karlin and Altschul, "Applications and statistics for multiple high-scoring segments in molecular sequences", Proc. Nat'l. Acad. Sci. USA, 90:5873-5787 (1993).

Kim, et al., "Sequence Divergence of Seryl-tRNA Synthetases in Archaea", J. Bacteriol., 180:6446-49 (1998).

Klein, et al., "High velocity microprojectiles for delivering nucleic acids into living cells", Nature, 327:70-73 (1987).

Kreitman and Pastan, "Purification and characterization of IL6-PE4E, a recombinant fusion of interleukin 6 with Pseudomonas exotoxin", Bioconjug. Chem., 4:581-585 (1993).

Kryukov, et al, "Characterization of mammalian selenoproteomes", Science, 300:1439-43 (2003).

LaRiviere, et al., "Uniform binding of aminoacyl-tRNAs to elongation factor Tu by thermodynamic compensation", Science, 294(5540):165-8 (2001).

Lee, et al., "The discriminator base influences tRNA structure at the end of the acceptor stem and possibly its interaction with proteins", PNAS, 90(15):7149-52 (1993).

Li, et al., "Cysteinyl-tRNA formation: the last puzzle of aminoacyl-tRNA synthesis", FEBS Lett., 462:302 (1999).

Li, et al., "Usage of an intronic promoter for stable gene expression in *Saccharomyces cerevisiae*", Lett Appl Microbiol., 40(5):347-52 (2005).

Ling , et al., "Phenylalanyl-tRNA synthetase editing defects result in efficient mistranslation of phenylalanine codons as tyrosine", RNA.,13(11):1881-6 (2007b).

Ling, et al., "Pathogenic mechanism of a human mitochondrial tRNAPhe mutation associated with myoclonic epilepsy with ragged red fibers syndrome", PNAS, 104(39):15299-304 (2007a).

Lipman, et al., "Synthesis of cysteinyl-tRNA(Cys) by a genome that lacks the normal cysteine-tRNA synthetase" Biochemistry 39:7792-8 (2000).

Liu, et al., "Catalytic mechanism of Sep-tRNA:Cys-tRNA synthase: sulfur transfer is mediated by disulfide and persulfide", J. Biol. Chem., 287:5426-33 (2012).

Logan and Shenk, "Adenovirus tripartite leader sequence enhances translation of mRNAs late after infection" Proc. Natl. Acad. Sci. USA, 81:3655-3659 (1984).

MacCoss, et al., "Probability-based validation of protein identifications using a modified SEQUEST algorithm", Anal. Chem., 74:5593-9 (2002).

Margelevicius and Venclovas, "PSI-BLAST-ISS: an intermediate sequence search tool for estimation of the position-specific alignment reliability", BMC Bioinformatics, 6:185 (2005).

Min, et al., "Transfer RNA-dependent amino acid biosynthesis: an essential route to asparagine formation", Proc. Natl. Acad. Sci. U.S.A., 99:2678 (2002).

Mino and Ishikawa, "A novel O-phospho-L-serine sulfhydrylation reaction catalyzed by O-acetylserine sulfhydrylase from Aeropyrum pernix K1", FEBS Lett., 551:133-8 (2003).

(56) References Cited

OTHER PUBLICATIONS

Mizutani, et al., "Possible Incorporation of phosphoserine into globin readthrough protein via bovine opal suppressor phosphoseryl-tRNA", FEBS Lett., 207(1):162-6 (1986).
Moore, "On the Determination of Cystine as Cysteic Acid", J. Biol. Chem., 238:235-7 (1963).
Needleman and Wunsch, "A general method applicable to the search for similarities in the amino acid sequence of two proteins", J. Mol. Biol., 4(3):443-53 (1970).
Nissen, et al., "Crystal structure of the ternary complex of Phe-tRNAPhe, EF-Tu, and a GTP analog", Science, 270(5241)1464-72 (1995).
Normanly, et al., "Changing the identity of a transfer RNA", Nature, 321:213-9 (1986).
Palioura, et al., "The human SepSecS-tRNASec complex reveals the mechanism of selenocysteine formation", Science, 325:321-5 (2009).
Park, et al., "Design and evolution of new catalytic activity with an existing protein scaffold", Science 311(5760):535-8 (2006).
Park, et al., "Expanding the genetic code of *Escherichia coli* with phosphoserine", Science, 33(6046):1151-4 (2011).
Pearson and Lipman, "Improved tools for biological sequence comparison", Proc. Nat'l. Acad. Sci. USA, 85:2444-8 (1988).
Polycarpo, et al., "Activation of the pyrrolysine suppressor tRNA requires formation of a ternary complex with class I and class II lysyl-tRNA synthetases", Mol.Cell, 12:287-94 (2003).
Polycarpo, et al., "An aminoacyl-tRNA synthetase that specifically activates pyrrolysine", Proc. Natl. Acad. Sci. U.S.A., 101;12450 (2004).
Raffa, "Diselenium, instead of disulfide, bonded analogs of conotoxins: novel synthesis and pharmacotherapeutic potential", Life Sci., 87(15-16):451-6 (2010).
Riaz and Mehmood, "Selenium in Human Health and Disease: A Review", JPMI, 26(02):120-33 (2012).
Rothman, et al., "Caged phosphoproteins", J Am Chem Soc., 127(3):846-7 (2005).
Ruan, et al., "Cysteinyl-tRNA(Cys) formation in Methanocaldococcus jannaschii: the mechanism is still unknown", J. Bacteriol. 186, 8-14 (2004).
Rudinger, et al., "Antideterminants present in minihelix(Sec) hinder its recognition by prokaryotic elongation factor Tu", EMBO J., 15(3):650-57 (1996).
Sadygov and Yates, A hypergeometric probability model for protein identification and validation using tandem mass spectral data and protein sequence databases\, Anal. Chem., 75:3792-8 (2003).
Sandig, et al., "Gene transfer into hepatocytes and human liver tissue by baculovirus vectors", Hum. Gene Ther., 7:1937-1945 (1996).
Sauerwald, et al., "RNA-dependent cysteine biosynthesis in archaea", Science, 307(5717):1969-72 (2005).
Schon, et al., "The selenocysteine-inserting opal suppressor series tRNA from *E. coli* is highly unusual in structure and modification", Nucleic Acids Res., 17(18):7159-65 (1989).
Schrader, et al. "Understanding the sequence of tRNA binding to EF-TU using tRNA mutagenesis", J Mol Biol, 386(5):1255-64 (2009).
Sebolt-Leopold, et al., "Targeting the mitogen-activated protein kinase cascade to treat cancer", Nat Rev Cancer, 4:937-47 (2004).
Shchedrina, et al., "Identification and characterization of a selenoprotein family containing a diselenide bond in a redox motif", PNAS, 104(35):13919-24 (2007).
Sherrer, et al., "Characterization and evolutionary history of an archaeal kinase Involved in selenocysteinyl-tRNA formation", Nucleic Acids Res., 36(4): 1247-59 (2008b).
Sherrer, et al., "Divergence of selenocysteine tRNA recognition by archaeal and eukaryotic O-phosphoseryl-tRNASec kinase", Nucleic Acids Res, 36:1871-80 (2008a).
Smith and Waterman, "Comparison of Biosequences", Adv. Appl. Math., 2:482-89 (1981).
Stathopoulos, et al., "Cysteinyl-tRNA synthetase is not essential for viability of the archaeon Methanococcus maripaludis", Proc. Natl. Acad. Sci. U.S.A., 98:14292-7 (2001).
Stathopoulos, et al., "One polypeptide with two aminoacyl-tRNA synthetase activities", Science, 287(5452):479-82 (2000).
Studier, "Protein production by auto-induction in high density shaking cultures", Protein Expr Purif.,41(1):207-34 (2005).
Tabb, et al., "DTASelect and Contrast: tools for assembling and comparing protein identifications from shotgun proteomics", J. Proteome Res., 1:21-6 (2002).
Takamatsu, et al., "Expression of bacterial chloramphenicol acetyltransferase gene in tobacco plants mediated by TMV-RNA", EMBO J., 6:307-311 (1987).
Tapiero, et al., "The antioxidant role of selenium and seleno-compounds", Biomed Pharmacother., 57:134-44 (2003).
Tomari, et al., "The role of tightly bound ATP in *Escherichia coli* tRNA nucleotidyltransferase", Genes Cells, 5:68998 (2000).
Tumbula, et al., "Transformation of Methanococcus maripaludis and identification of a PstI-like restriction system", FEMS Microbiol. Lett., 121:309-14 (1994).
Van Heeke and Schuster, "Expression of human asparagine synthetase in *Escherichia coli*", J. Biol. Chem., 264:5503-5509 (1989).
Varshney, et al., "Direct analysis of aminoacylation levels of tRNAs in vivo. Application to studying recognition of *Escherichia coli* initiator tRNA mutants by glutaminyl-tRNA synthetase", J. Biol. Chem. 266:24712 (1991).
Wang, et al., "Expanding the genetic code of *Escherichia coli*", Science, 292(5516):498-500 (2001).
Wanner, "Molecular genetic studies of a 10.9-kb operon in *Escherichia coli* for phosphonate uptake and biodegradation", FEMS Microbiol Lett., 79(1-):133-9 (1992).
White, "The biosynthesis of cysteine and homocysteine in Methanococcus jannaschii", Biochim. Biophys. Acta, 1624:46-53 (2003).
Whitman, et al., "Isolation and characterization of 22 mesophillic methanococci", Syst. Appl. Microbiol, 7:235-40 (1986).
Wolfson and Uhlenbeck, "Modulation of tRNAAla identity by inorganic pyrophosphatase", Proc. Natl. Acad. Sci. U.S.A., 99:5965-70 (2002).
Wu and Gross, "The length and the secondary structure of the D-stem of human selenocysteine tRNA are the major identity determinants for serine phosphorylation", EMBO J., 13:241-8 (1994).
Xu, et al., "New developments in selenium biochemistry: selenocysteine biosynthesis in eukaryotes and archaea", Biol TraceElem Res., 119(3):234-41 (2007).
Yoshizawa and Böck, "The many levels of control on bacterial selenoprotein synthesis", Biochim Biophys Acta., 1790:1404-14 (2009).
Yuan, et al., "Distinct genetic code expansion strategies for selenocysteine and pyrrolysine are reflected in different aminoacyl-tRNA formation systems", FEBS Lett., 584(2):342-9 (2010).
Yuan, et al., "RNA-dependent conversion of phosphoserine forms selenocysteine in eukaryotes and archaea", PNAS, 103:18923-7 (2006).
Zhang and Hou, "Synthesis of cysteinyl-tRNACys by a prolyl-tRNA synthetase", RNA Biol., 1:35-41 (2004).
Zhang, et al., "Aminoacylation of tRNA with phosphoserine for synthesis of cysteinyl-tRNA(Cys", Nat. Struct Mol. Biol., 15(5):507-14 (2008).
Zhu, et al., Shotgun Proteomics of Methanococcus jannaschii and insights into methanogenesis\, J. Proteome Res., 3:538 (2004).
U.S. Appl. No. 15/724,687, filed Oct. 4, 2017, Soll Dieter.
Aldag, et al., "Probing the role of the proximal heme ligand in cytochrome P450cam by recombinant incorporation of selenocysteine", PNAS, 106:5481-6 (2009).
Ambrogelly, et al., "Pyrrolysine is not hardwired for cotranslational insertion at UAG codons", PNAS, 104:3141-6 (2007).
Arner, "Recombinant expression of mammalian selenocysteine-containing thioredoxin reductase and other selenoproteins in *Escherichia coli*", Methods Enzymol., 347:226-35 (2002).
Arner, "Selenoproteins-What unique properties can arise with selenocysteine in place of cysteine", Exp. Cell Res 316:1296-1303 (2010).

(56) References Cited

OTHER PUBLICATIONS

Ataide, et al., "Stationary-phase expression and aminoacylation of a transfer-RNA-like small RNA", EMBO Rep, 6:742-7 (2005).
Bain, et al., "Ribosome-mediated incorporation of a non-standard amino acid into a peptide through expansion of the genetic code", Nature, 356:537-9 (1992).
Beld, et al., "Selenoglutathione: efficient oxidative protein folding by a diselenide", Biochemistry, 46:5382-90 (2007).
Biou, et al., "The 2.9 a crystal structure of T. thermophilus seryl-tRNA synthetase complexed with tRNA(Ser)", Science, 263:1404-10 (1994).
Bock, et al., "Selenocysteine in: The Aminoacyl-tRNA Synthetases", Ibba, M., Francklyn, C. and Cusack, S., Eds.,, pp. 320-327, Landes Bioscience, Georgetown, TX (2005).
Borrel, et al., "Unique characteristics of the pyrrolysine system in the 7th order of methanogens; implications for the evolution of a genetic code expansion cassette", Archaea, 374146 (2014).
Bröcker, et al., "Recoding the genetic code with selenocysteine", Angew. Chem. Int. Ed. Engl., 53, 319-23 (2014).
Campbell, et al., "UGA is an additional glycine codon in uncultured SR1 bacteria from the human microbiota", PNAS, 110:5540-5 (2013).
Cooley, et al., "Post-transcriptional nucleotide addition is responsible for the formation of the 5' terminus of histidine tRNA", PNAS, 79:6475-9 (1982).
Cravedi, et al., "Evolution of the Selenoproteome in Helicobacter pylori and Epsilonproteobacteria", Genome Biol Evol, 7:2692-2704 (2015).
Fan, et al., "Manipulating Cellular Activities Using an Ultrasound-Chemical Hybrid Tool", ACS Synth Biol. 6L2021-7 (2017).
Fan, et al., "Efficient Expression of Glutathione Peroxidase with Chimeric tRNA in Amber-less *Escherichia coli*", ACS Synth Biol., 7:249-57 (2018).
Fischer, et al., "The pathway to GTPase activation of elongation factor SelB on the ribosome", Nature, 540:80-5 (2016).
Gupta, et al., "Reconstitution of selenocysteine incorporation reveals intrinsic regulation by SECIS elements", J. Mol. Biol., 425:2415-22 (2013).
Hamashima, et al., "Alternative genetic code for amino acids and transfer RNA revisited", Biomol Concepts, 4:309-18 (2013).
Hamashima, et al., "Expansion of Noncanonical V-Arm-Containing tRNAs in Eukaryotes", Mol Biol Evol, 33:530-40 (2016).
Haruna, et al., "Engineering the elongation factor Tu for efficient selenoprotein synthesis", Nucleic Acids Res, 42:9976-83 (2014).
Himeno, et al., "Conversion of aminoacylation specificity from tRNA(Tyr) to tRNA(Ser) in vitro", Nucleic Acids Res, 18:6815-9 (1990).
Hou, et al., "A simple structural feature is a major determinant of the identity of a transfer RNA", Nature, 333:140-5 (1988).
Hubert, et al., "The 9/4 secondary structure of eukaryotic selenocysteine tRNA: more pieces of evidence", RNA, 4:1029-33 (1998).
Isaacs, et al., "Precise manipulation of chromosomes in vivo enables genome-wide codon replacement", Science, 333:348-53 (2011).
Itoh, et al., "Crystal structure of human selenocysteine tRNA", Nucleic Acids Res, 37:6259-6268 (2009).
Itoh, et al., "Tertiary structure of bacterial selenocysteine tRNA", Nucleic Acids Res, 41:6729-38 (2013).
Itoh, et al., "Decameric SelA●tRNA(Sec) ring structure reveals mechanism of bacterial selenocysteine formation", Science, 340:75-78 (2013b).
Ivanova, et al., "Stop codon reassignments in the wild",Science, 344:909-13 (2014).
Jewett, et al., "An integrated cell-free metabolic platform for protein production and synthetic biology", Mol. Syst. Biol., 4:220 (2008).
Kang, et al., "Ribosomal synthesis of nonstandard peptides", Biochem. Cell Biol., 86:92-99 (2008).
Katz, et al., "Non-canonical roles of tRNAs and tRNA mimics in bacterial cell biology", Mol Microbiol, 101(4):545-58 (2016).

Kim, et al., "Selenium utilization in thioredoxin and catalytic advantage provided by selenocysteine", Biochem Biophys Res Commun, 461:648-52 (2015).
Komatsoulis, et al., "Recognition of tRNA(Cys) by *Escherichia coli* cysteinyl-tRNA synthetase", Biochemistry, 32:7435-44 (1993).
Kumar, et al., "Selenite is a substrate for calf thymus thioredoxin reductase and thioredoxin and elicits a large non-stoichiometric oxidation of NADPH in the presence of oxygen.", Eur J Biochem, 207:435-9 (1992).
Lacourciere, et al., "Direct detection of potential selenium delivery proteins by using an *Escherichia coli* strain unable to incorporate selenium from selenite into proteins", PNAS, 99:9150-3 (2002).
Lajoie, et al., "Genomically recoded organisms expand biological functions", Science 342:357-60 (2013).
Larkin, et al., "Clustal W and Clustal X version 2.0.", Bioinformatics, 23:2947-8 (2007).
Laslett, et al., "ARAGORN, a program to detect tRNA genes and tmRNA genes in nucleotide sequences", Nucleic Acids Res, 32:11-16 (2004).
Liu, et al., "Adding new chemistries to the genetic code", Annu. Rev. Biochem., 79:413-44 (2010).
Liu, et al., "Adaptation to tRNA acceptor stem structure by flexible adjustment in the catalytic domain of class I tRNA synthetases", RNA, 18:213-21 (2012).
Llado, et al., "*Silvibacterium bohemicum* gen. nov. sp. nov., an acidobacterium isolated from coniferous soil in the Bohemian Forest National Park", Syst Appl Microbiol, 39:14-19 (2016).
Malyshev, et al., "A semi-synthetic organism with an expanded genetic alphabet", Nature, 509:385-8 (2014).
Marck, et al., "tRNomics: analysis of tRNA genes from 50 genomes of Eukarya, Archaea, and Bacteria reveals anticodon-sparing strategies and domain-specific features", RNA, 8:1189-1232 (2002).
Markowitz, et al., "IMG/M 4 version of the integrated metagenome comparative analysis system", Nucleic Acids Res, 42:D568-573 (2014).
Masson and Miller, "Expression of synthetic suppressor tRNA genes under the control of a synthetic promoter", Gene, 47:179-83 (1986).
McClain, et al., "Changing the identity of a tRNA by introducing a G-U wobble pair near the 3' acceptor end", Science, 240:793-6 (1988).
Mehta, et al., "Efficiency of mammalian selenocysteine incorporation", J. Biol. Chem., 279:37852-9 (2004).
Meinnel, et al., "Fast purification of a functional elangator tRNAmet expressed from a synthetic gene in vivo", Nucleic Acids Res., 16:8095-6 (1988).
Miller, et al., "A synthetic tRNA for EF-Tu mediated selenocysteine incorporation in vivo and in vitro," FEBS Letters, 589:2194-2199 (2015).
Mizutani, et al., "The dual identities of mammalian tRNA(Sec) for SerRS and selenocysteine synthase", Mol Biol Rep, 25:211-6 (1998).
Mühlhausen, et al., "A novel nuclear genetic code alteration in yeasts and the evolution of codon reassignment in eukaryotes", Genome Res, 26:945-955 (2016).
Mukai, et al., "Transfer RNAs with novel cloverleaf structures," Nucleic Acids Research, 45(5):2776-2785 (2017).
Mukai, et al., "Facile Recoding of Selenocysteine in Nature", Angew Chem Int Ed Engl, 55: 5337-41 (2016).
Mukai, et al., "RNA-Dependent Cysteine Biosynthesis in Bacteria and Archaea", MBio, 8, e00561-00517 (2017B).
Mustoe, et al., "Noncanonical secondary structure stabilizes mitochondrial tRNA(Ser(UCN)) by reducing the entropic cost of tertiary folding", J Am Chem Soc, 137:3592-9 (2015).
Naganuma, et al., "The selective tRNA aminoacylation mechanism based on a single G•U pair", Nature, 510:507-11 (2014).
Nozawa, et al., "Pyrrolysyl-tRNA synthetase-tRNA(Pyl) structure reveals the molecular basis of orthogonality", Nature, 457:1163-7 (2009).
Orellana, et al., "The additional guanylate at the 5' terminus of *Escherichia coli* tRNAHis is the result of unusual processing by RNase P.", Mol Cell Biol, 6:525-9 (1986).

(56) References Cited

OTHER PUBLICATIONS

Paleskava, et al., "Thermodynamic and kinetic framework of selenocysteyl-tRNASec recognition by elongation factor SelB", J. Biol. Chem., 285:3014-20 (2010).

Pallanck, et al., "The anticodon and discriminator base are major determinants of cysteine tRNA identity in vivo", J Biol Chem, 267:7221-3 (1992).

Santesmasses, et al., "Computational identification of the selenocysteine tRNA (tRNASec) in genomes", PLoS Comput Biol, 13, e1005383 (2017).

Seebeck, et al., "Artificial lantipeptides from in vitro translations", Chem. Commun. (Camb.), 47:6141-3 (2011).

Silva, et al., "Formation of a Ternary Complex for Selenocysteine Biosynthesis in Bacteria", J Biol Chem, 290:29178-29188 (2015).

Sprinzl, et al., "Compilation of tRNA sequences and sequences of tRNA genes", Nucleic Acids Research, 26(1):148-153 (1998).

Suzuki, et al., "The 'polysemous' codon—a codon with multiple amino acid assignment caused by dual specificity of tRNA identity", EMBO J, 16:1122-34 (1997).

Swart, et al., "Genetic Codes with No Dedicated Stop Codon: Context-Dependent Translation Termination", Cell, 166:691-702 (2016).

Tamura, et al., "Selenite reduction by the thioredoxin system: kinetics and identification of protein-bound selenide",Biosci Biotechnol Biochem, 75:1184-7 (2011).

Thyer, et al., "Evolving tRNA(Sec) for efficient canonical incorporation of selenocysteine", J Am Chem Soc, 137:46-49 (2015).

Tisné, et al., "NMR and biochemical characterization of recombinant human tRNA(Lys)3 expressed in *Escherichia coli*: identification of posttranscriptional nucleotide modifications required for efficient initiation of HIV-1 reverse transcription", RNA, 6:1403-1412 (2000).

Turanov, et al., "Genetic code supports targeted insertion of two amino acids by one codon", Science, 323:259-261 (2009).

Wu, et al., "The long extra arms of human tRNA((Ser)Sec) and tRNA(Ser) function as major identify elements for serylation in an orientation-dependent, but not sequence-specific manner", Nucleic Acids Res, 21:5589-5594 (1993).

Xu, et al., "Wobble decoding by the *Escherichia coli* selenocysteine insertion machinery", Nucleic Acids Res., 41:9800-9811 (2013).

Xu, et al., "Biosynthesis of selenocysteine on its tRNA in eukaryotes", PLoS Biol, 5, e4 (2007).

* cited by examiner

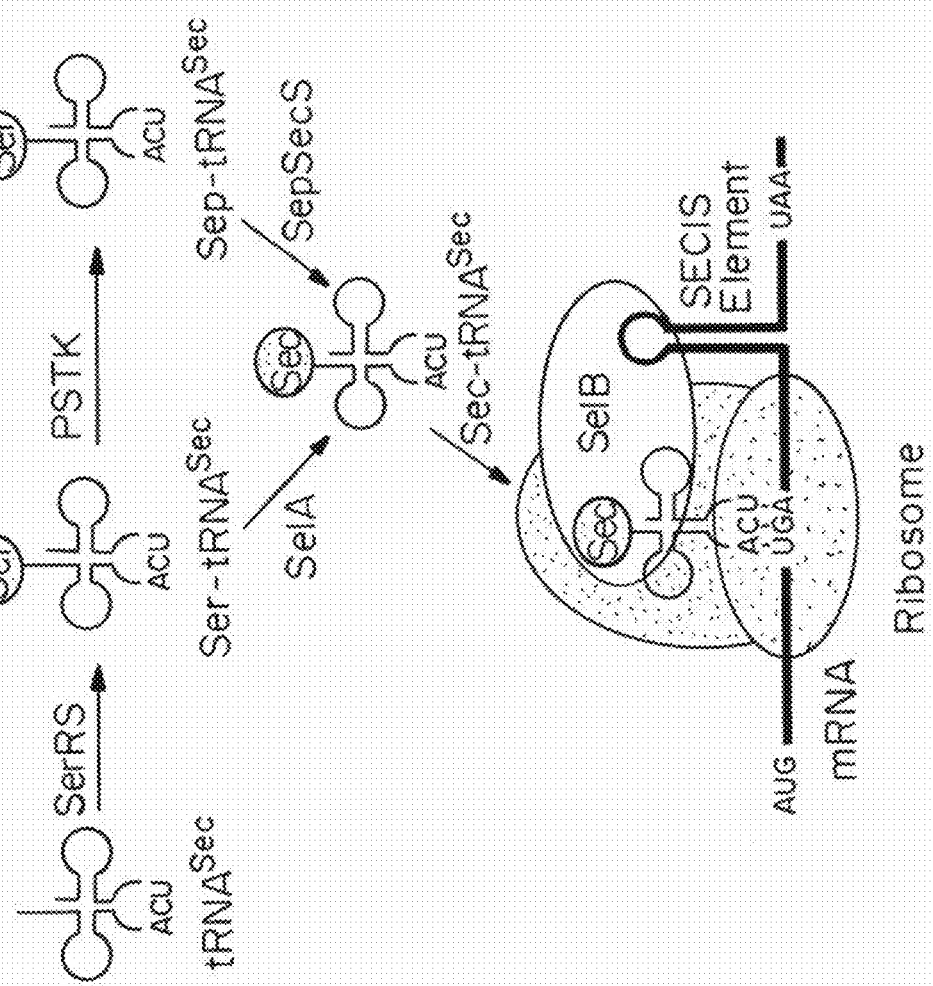
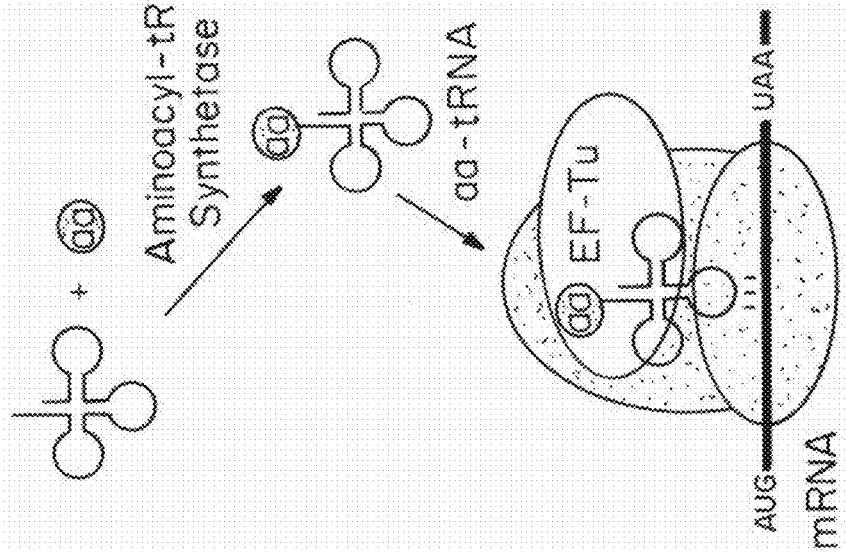
FIG. 1A
FIG. 1B

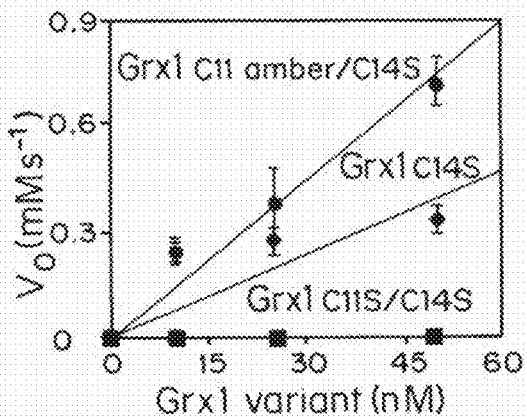
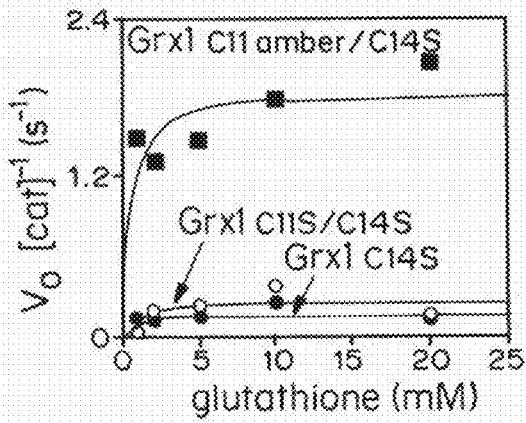
FIG. 7A
FIG. 7B
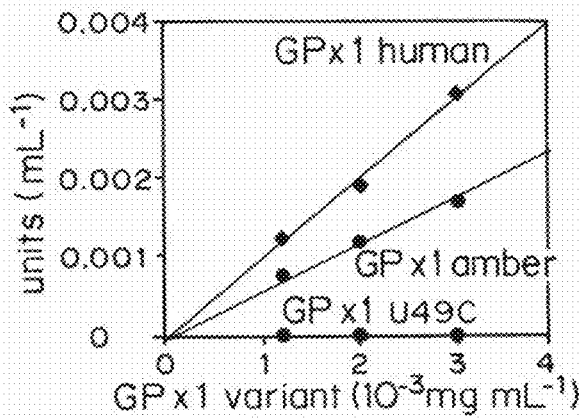
FIG. 7C
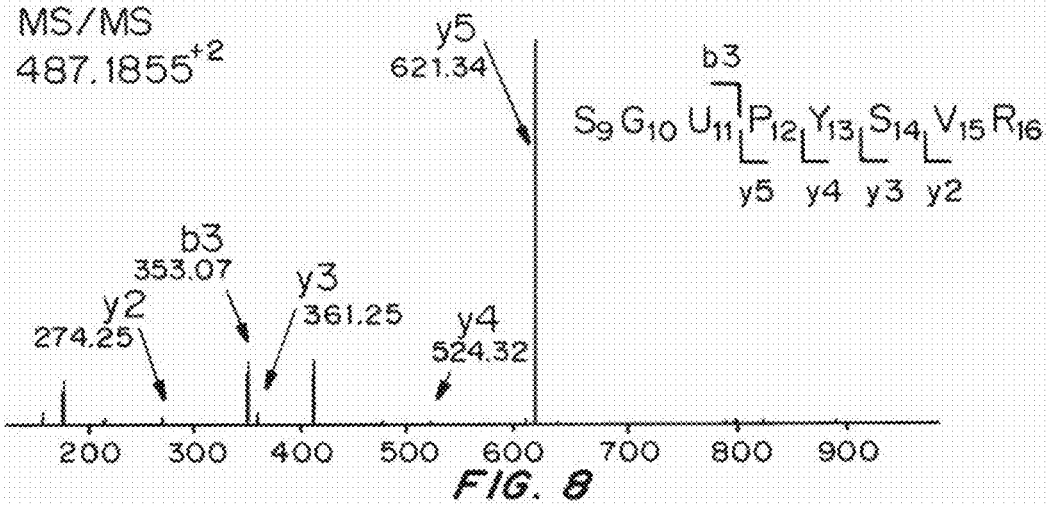
FIG. 8

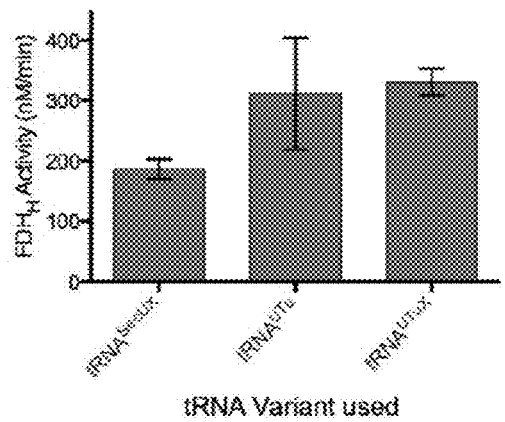 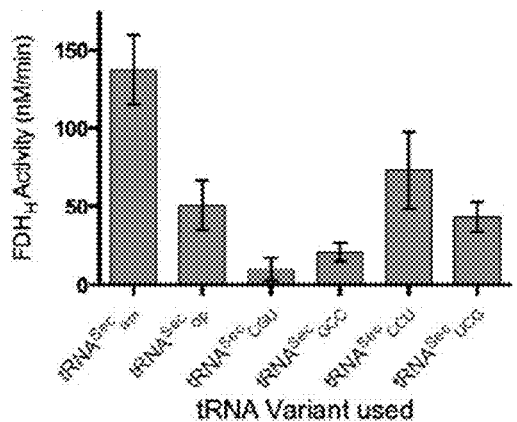
FIG. 19A  FIG. 19B
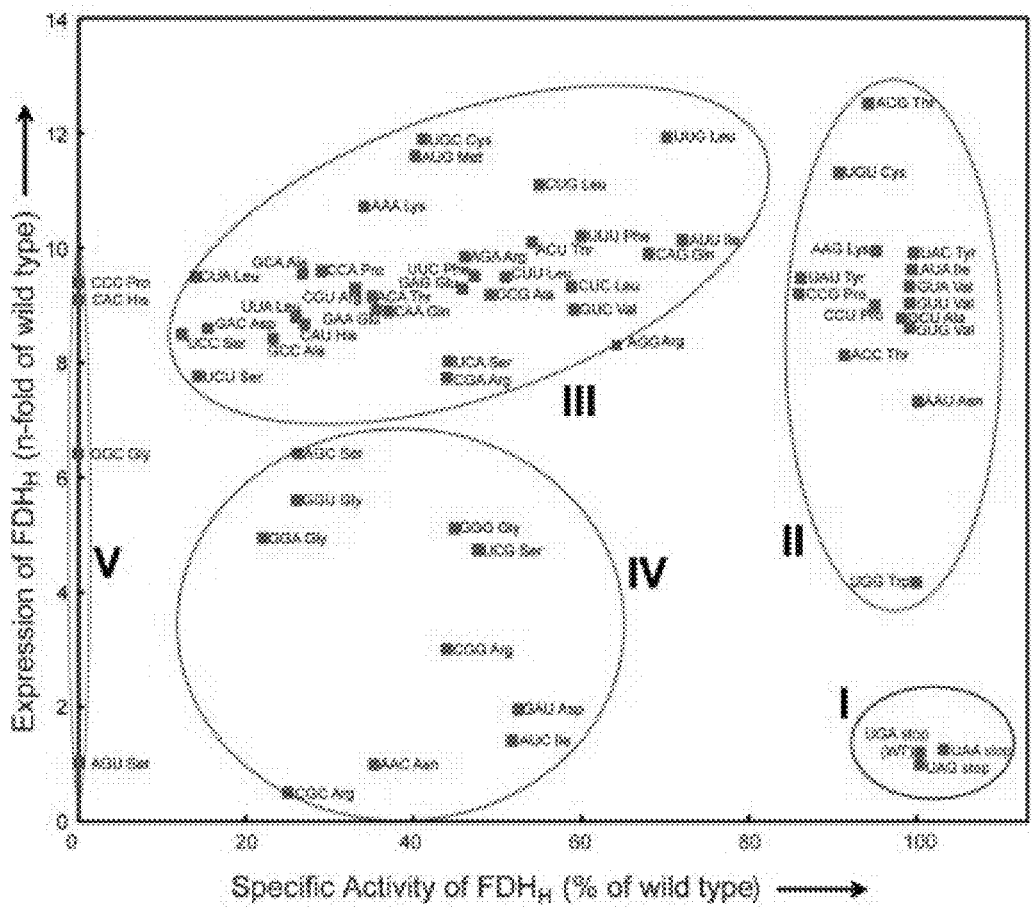
FIG. 20A

COMPOSITIONS AND METHODS FOR MAKING SELENOCYSTEINE CONTAINING POLYPEPTIDES

CROSS-REFERENCE TO RELATED APPLICATIONS

This application is a continuation-in-part of U.S. Ser. No. 14/131,382, filed Jan. 7, 2014, which is a 371 application of PCT/US2012/046252, entitled "Compositions and Methods for Making Selenocysteine Containing Polypeptides," filed Jul. 11, 2012, which claims priority to U.S. Provisional Application No. 61/506,338, entitled "System for Co-translational Selenocysteine Insertion at Any Position of a Protein" filed Jul. 11, 2011, each of which is incorporated by reference in its entirety.

STATEMENT REGARDING FEDERALLY SPONSORED RESEARCH OR DEVELOPMENT

This invention was made with government support under GM022854 awarded by National Institute of Health, DE-FG02-98ER20311 awarded by the Department of Energy and 0950474 awarded by the National Science Foundation. The government has certain rights in the invention.

REFERENCE TO THE SEQUENCE LISTING

The Sequence Listing submitted as a text file named "YU_5714_CIP_ST25.txt," created on Jul. 5, 2016, and having a size of 25,516 bytes is hereby incorporated by reference pursuant to 37 C.F.R. § 1.52(e)(5).

FIELD OF THE INVENTION

The field of the invention generally relates to compositions including recombinant tRNAs and methods of using them to manufacture recombinant selenocysteine containing polypeptides.

BACKGROUND OF THE INVENTION

Selenocysteine, commonly referred to as the twenty-first amino acid, is incorporated into at least 25 human proteins. Natural co-translational incorporation of selenocysteine (Sec) into proteins proceeds by a recoding process so that upon encountering the UGA codon in the messenger RNA the ribosome knows to recognize it as Sec instead of Stop. This process requires three components: (i) the aminoacyl-tRNA carrying selenocysteine, Sec-tRNA$^{Sec}$; (ii) the specialized elongation factor, SelB, carrying Sec-tRNA$^{Sec}$ to the ribosome, and (iii) the SECIS element, an RNA secondary structure of the mRNA just downstream of the UGA codon, that interacts with the SelB•Ser-tRNA$^{Sec}$ complex (Böck, A, Thanbichler, M, Rother, M & Resch, A (2005), eds Ibba M, Francklyn C S, & Cusack S (Landes Bioscience, Georgetown, Tex.), pp 320-327; Yoshizawa, S & Böck, A (2009) Biochim Biophys Acta 1790:1404-1414). Additionally, in order to protect the integrity of this recoding process, Sec-tRNA$^{Sec}$ is not recognized by the general elongation factor EF-Tu because of the presence of three base pairs that act as antideterminants (Rudinger, J, Hillenbrandt, R, Sprinzl, M & Giege, R (1996) EMBO J 15:650-657). Sec-tRNA$^{Sec}$ cannot be accommodated during normal translation because it is not an acceptable substrate for EF-Tu, and the SelB• Sec-tRNA$^{Sec}$ complex will not decode in-frame UGA codons in absence of the SECIS.

Insertion of selenocysteine into a recombinant protein, for example, substitution of a naturally occurring cysteine residue for selenocysteine, can alter the function of the protein. Substituting one or more naturally occurring Cys residues in the active site of an enzyme with a Sec can increase the activity of this enzyme. Diselenide bonds have very low redox potential. Therefore, replacing disulfide bonds with diselenide or selenocysteine-cysteine bonds can lower dosage, increase half-life, increase stability, reduce toxicity, alter pharmacokinetics, change folding properties, or combinations thereof of the recombinant selenocysteine containing protein relative to a reference protein without selenocysteines, such as a naturally occurring counterpart.

However, due the presence the SECIS element as an integral part of the open reading frame (within the mRNA) encoding the protein that harbors Sec in its sequence, it is not possible to insert Sec into proteins by a standard mutational scheme or in the construction of random mutagenic libraries, and production of Sec proteins is limited to costly and inefficient methods of protein synthesis. Accordingly, there is a need for alternative methods of manufacturing selenocysteine containing polypeptides.

It is an object of the invention to provide compositions and methods for recombinant expression of proteins engineered to include one or more selenocysteine residues without the requirement of a SECIS in the mRNA encoding the protein.

It is a further object of the invention to provide non-naturally occurring proteins including one or more selenocysteine residues.

SUMMARY OF THE INVENTION

Non-naturally occurring tRNA$^{Sec}$ and methods of using them for recombinant expression of proteins engineered to include one or more selenocysteine residues are disclosed. Typically, the non-naturally occurring tRNA$^{Sec}$ (1) can be recognized by SerRS and by EF-Tu, or variants thereof, and is characterized by one or more of the following elements: (2) when aminoacylated with serine, the non-naturally occurring Ser-tRNA$^{Sec}$ can be converted to non-naturally occurring Sec-tRNA$^{Sec}$ by SelA, or variant thereof, (3) when aminoacylated with serine, the non-naturally occurring Ser-tRNA$^{Sec}$ can be phosphorylated by PSTK or variant thereof, (4) when aminoacylated with phosphorylated serine, the non-naturally occurring Sep-tRNA$^{Sec}$ can serve as a substrate for SepSecS or variant thereof; and combinations thereof. In some embodiments, the non-naturally occurring Ser-tRNA$^{Sec}$ is characterized by elements (1) and (2). In some embodiments, the non-naturally occurring Ser-tRNA$^{Sec}$ is characterized by elements (1), (3), and (4). In some embodiments, the non-naturally occurring Ser-tRNA$^{Sec}$ is characterized by elements (1), (2), (3), and (4). In some embodiments, the non-naturally occurring Ser-tRNA$^{Sec}$ is characterized by elements (1), (2), and (3).

The non-naturally occurring tRNA$^{Sec}$ do not require a SECIS element in an mRNA to be incorporated into a growing polypeptide chain during translation. Typically the anticodon of the non-naturally occurring tRNA$^{Sec}$ is recognized or hybridizes to a stop codon.

Exemplary tRNAs, isolated nucleic acids encoding the tRNAs, vectors thereof, and host cells expressing the tRNA are also provided. For example, an isolated nucleic acid can include a nucleic acid sequence encoding a non-naturally occurring tRNA$^{Sec}$, wherein the non-naturally occurring tRNA$^{Sec}$ is recognized by SerRS and by EF-Tu, or variants thereof, and when aminoacylated with serine the Ser-tRNA is a substrate for SelA or a variant thereof. The tRNA$^{Sec}$ can be a variant of a naturally occurring E. coli tRNA$^{Ser}$, wherein the acceptor stem of E. coli tRNA$^{Ser}$ is replaced with the acceptor stem of E. coli tRNA$^{Sec}$. In some embodiments, the non-naturally occurring tRNA$^{Sec}$ includes at least 80%, 85%, 90%, 95%, or more sequence identity to SEQ ID NO:6, 7, or 8. The non-naturally occurring tRNA$^{Sec}$ can exhibit tighter binding with SelA than the tRNA of SEQ ID NO:7, while retaining Ser-tRNA formation by SerRS. In some embodiments, the non-naturally occurring tRNA$^{Sec}$ includes one or more mutations at positions U8, G9, or A27 in the core region; A14 or G15 in the D-arm; U21 in the D-loop; A52 or U62 in the T-arm; A59 in the T-loop; U44 and G48, or a combination thereof in the variable arm relative to SEQ ID NO:6, 7, or 8 (e.g., according to the nucleotide positional numbering established in Sprinzl, et al., *Nucleic Acids Research*, 26(1):148-153 (1998)). The mutations can be, for example, one or more, or preferably all, of: U8G, G9U, and A27G in the core region; A14U and G15C in the D-arm; deletion of U21 in the D-loop; A52G and U62C in the T-arm; A59C in the T-loop; and the insertion of residues U44 and G48 in the variable arm.

The mutations can also be relative to the backbone nucleotide numbering of SEQ ID NO:6, 7, or 8 beginning with the terminal 5' nucleotide in SEQ ID NO:6, 7, or 8. For example, the variant can have one or more mutations selected from the group consisting of (i) nucleotide positions 9 and/or 10 remain unchanged or are substituted; (ii) nucleotides 15 and/or 16 remain unchanged or are substituted; (iii) nucleotide 20 remains unchanged or is deleted; (iv) one or both of nucleotides 25 and 26 remain unchanged, one or both of nucleotides 25 and 26 are substituted, a nucleotide is inserted between nucleotides 25 and 26, or a combination thereof; (v) nucleotide 28 remains unchanged or is substituted; (vi) one or two nucleotides are inserted between nucleotides 45 and 46; (vii) one or two nucleotides are inserted between nucleotides 61 and 62; (viii) nucleotide 65 remains the same or is substituted; (ix) nucleotide 72 remains the same or is substituted; (x) nucleotide 75 remains the same or is substituted; or a combination thereof relative to SEQ ID NO:6, 7, or 8. In specific embodiments, the tRNA includes the sequence of any one of SEQ ID NO:59-85, or a variant thereof with a substituted anticodon.

In some embodiments, the isolated nucleic acid includes a heterologous expression control sequence for expression of the tRNA. In some embodiments, the nucleic acid encoding the tRNA is in an expression vector. Host cells including the nucleic acid encoding the tRNA are also provided. The host cell can be, for example, a prokaryote, archaeon, or eukaryote. The nucleic acid is incorporated into the genome of the cell or expressed episomally. The host cell can be a genetically recoded organism.

Methods of manufacturing selenocysteine containing polypeptides are also disclosed. The non-naturally occurring tRNA$^{Sec}$ can be used for recombinant manufacture of selenocysteine containing polypeptides encoded by mRNA without the requirement of an SECIS element. In some embodiments, the non-naturally occurring tRNA$^{Sec}$ is co-expressed in a recombinant expression system, such as E. coli, with SerRS, EF-Tu, SelA, or PSTK and SepSecS, or a combination of SelA, PSTK and SepSecS, and an mRNA with at least one codon that recognizes the anticodon of the non-naturally occurring tRNA$^{Sec}$ to manufacture a selenocysteine containing polypeptide encoded by the mRNA.

Nucleic acids encoding selenocysteine containing polypeptides are also disclosed. The nucleic acids encode a polypeptide of interest and include a non-natural tRNA$^{Sec}$ recognition codon, for example a "stop" codon, that hybridizes with the anticodon of the non-naturally occurring tRNA$^{Sec}$, such that a selenocysteine is transferred onto the growing polypeptide chain during translation. The selenocysteine containing polypeptides can be polypeptides that contain selenocysteine in nature, or polypeptides that do not contain selenocysteine in nature. For example, a non-naturally occurring tRNA recognition codon can be substituted for a cysteine codon in the naturally occurring mRNA, which changes the cysteine to a selenocysteine when the nucleic acid encoding the polypeptide is expressed recombinantly with the non-naturally occurring tRNA$^{Sec}$. Substituting one or more naturally occurring Cys residues with a Sec can increase activity, lower dosage, reduce toxicity, improve stability, increase efficacy, increase half-life or combinations thereof of a selenocysteine containing protein relative to its cysteine containing counterpart.

Methods of treating subjects in need thereof with recombinant selenocysteine containing polypeptides prepared using the disclosed compositions and methods are also disclosed. Particularly preferred proteins containing selenocysteine include antibodies and enzymes having altered binding affinity and/or pharmacokinetics.

BRIEF DESCRIPTION OF THE DRAWINGS

FIGS. 1A-1B are illustrations showing the canonical and Sec translation apparatuses respectively. The canonical amino acids are charged onto their respective tRNA by their cognate aminoacyl-tRNA synthetase. The aminoacyl-tRNA is then delivered by EF-Tu to the ribosome (FIG. 1A). In contrast, the Sec pathway requires several biosynthetic steps. First, tRNA$^{Sec}$ is misacylated to Ser-tRNA$^{Sec}$ by SerRS. While in bacteria Ser-tRNA$^{Sec}$ is directly converted by SelA to Sec-tRNA$^{Sec}$, archaea and eukaryotes employ an additional phosphorylation step by PSTK to form Sep-tRNA$^{Sec}$, which is then converted by SepSecS to the final product Sec-tRNA$^{Sec}$ (FIG. 1B). Sec-tRNA$^{Sec}$ is bound by elongation factor SelB and delivered to the ribosome. However, reassignment of the opal codon UGA to a Sec codon is only achieved if SelB also binds to the mRNA SECIS hairpin structure.

tRNA$^{UTu}_{am}$, SEQ ID NO:10). Transplanted PSTK identity elements are boxed. "<" identifies potential locations of additional base pairs in the acceptor stem. "Arrow" identifies the location of other possible mutations. Specifically, the <depict one possible insertion of a G-C base pair between the 1$^{st}$ and 2$^{nd}$ base pair and a second possible insertion of a G-C pair insertion between the 6$^{th}$ and 7$^{th}$ base pair of the acceptor stem. The arrows depict a possible change in the 50:64 base pair (A-U) to a U-A pair, and substitution of the serine anticodon (UGA) with opal (UCA) or amber (CUA) anticodon.

Figure 5:
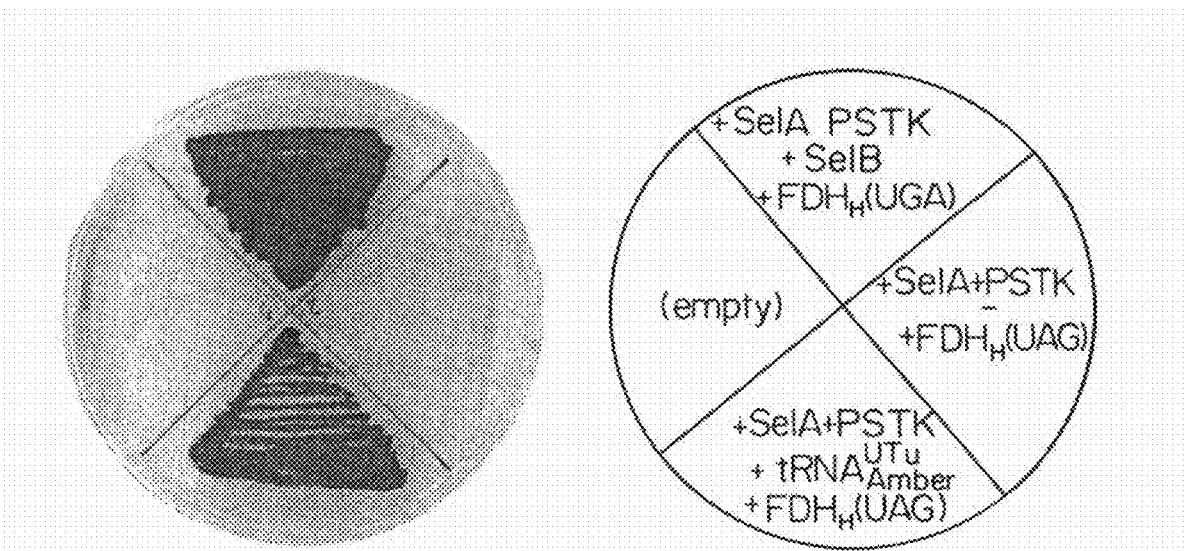

FIG. 5 is a photograph showing FDH$_H$ activity in *E. coli* MH5 (selA, selB, fdhF mutant) strain transformed with (clockwise from top) (1) SelA+PSTK+SelB+FDH$_H$(UGA); (2) SelA+PSTK+FDH$_H$(UAG); (3) SelA+PSTK+tRNA$^{UTu}$ (amber)+FDH$_H$(UAG); (4) empty plasmid.

Figure 6:
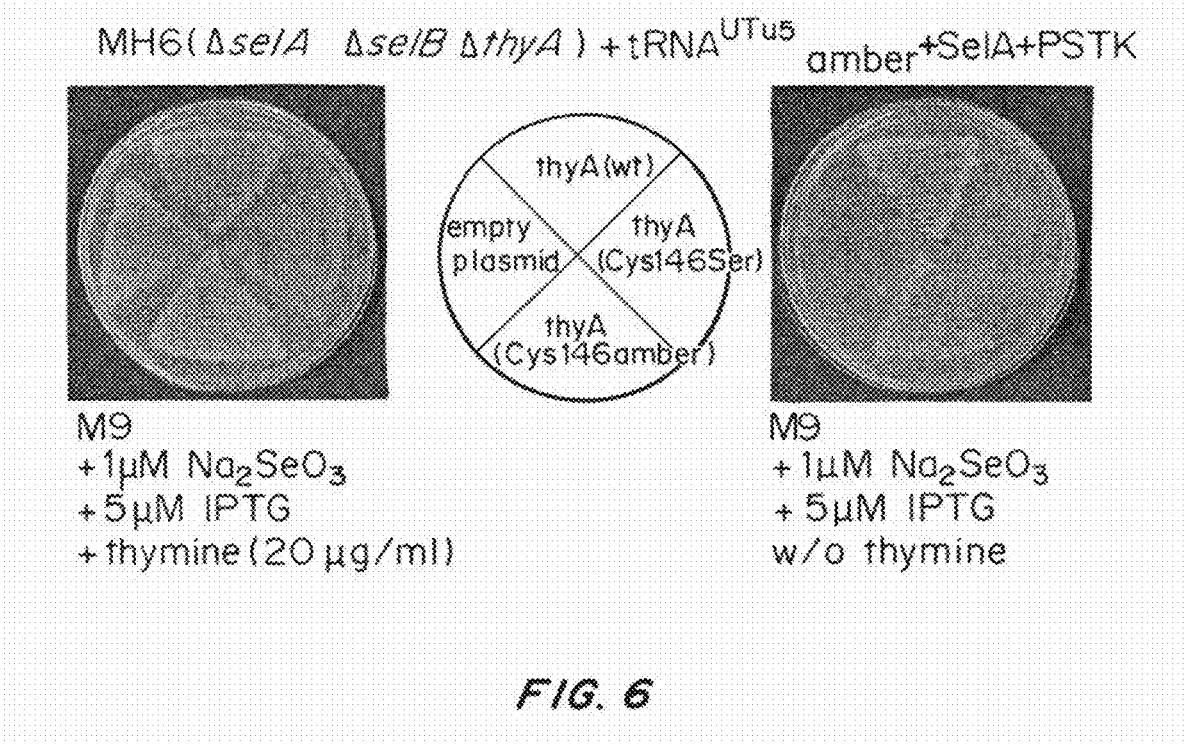

FIG. 6 is a photograph showing thymidylate synthase activity in *E. coli* MH6 (selA, selB, thyA mutant) strain transformed with (clockwise from top) (1) tRNA$^{UTu}$(amber)+SelA+PSTK+thyA (wildtype); (2) tRNA$^{UTu}$(amber)+SelA+PSTK+thyA (Cys146Ser); (3) tRNA$^{UTu}$(amber)+SelA+PSTK+thyA (Cys146amber); (4) empty plasmid; grown in M9+1 μM Na$_2$SeO$_3$+5 μM IPTG+thymine (20 μg/ml) (left panel) or M9+1 μM Na$_2$SeO$_3$+5 μM IPTG+w/o thymine (right panel).

FIG. 7A is a line graph showing the disulfide oxidoreductase activity ($V_0$(mMs$^{-1}$)) of Grx1$_{C11am/C14S}$Sec, Grx1$_{C11S/C14S}$ and Grx1$_{C14S}$ at increasing concentrations (nM). FIG. 7B is a line graph showing the peroxidase activity ($V_0$[cat]$^{-1}$(s$^{-1}$)) of Grx1$_{C11am/C14S}$Sec, Grx1$_{C11S/C14S}$ and Grx1$_{C14S}$ as a function of reduced glutathione concentration at 25° C. (mM). FIG. 7C is a line graph showing peroxidase activity (units (mL$^{-1}$)) of Sec containing GPx1$_{am}$ and Cys containing GPx1$_{Cys}$ that were overexpressed in *E. coli* and compared to commercially available GPx$_{hum}$ from human erythrocytes as a function of GPx1 (10$^{-3}$ mg mL$^{-1}$).

FIG. 8 is a spectrogram showing the presence of selenocysteine at amino acid position 11 in Grx1$_{C11am/C14S}$Sec by mass spectroscopy. Shown is the MS/MS spectrum of the trypsin-digested Sec-containing fragment $S_9G_{10}U_{11}P_{12}Y_{13}S_{14}V_{15}R_{16}$. Fragments observed in the second mass spectrometric analysis of this peptide are labeled with b3, y2, y3, y4 and y5. The Sec residue of the peptide in the MS/MS experiment was first treated with DTT, and then alkylated with iodoacetamide for oxidative protection of the selenol. The unit m/z describes the mass-to-charge ratio.

Figure 9A:
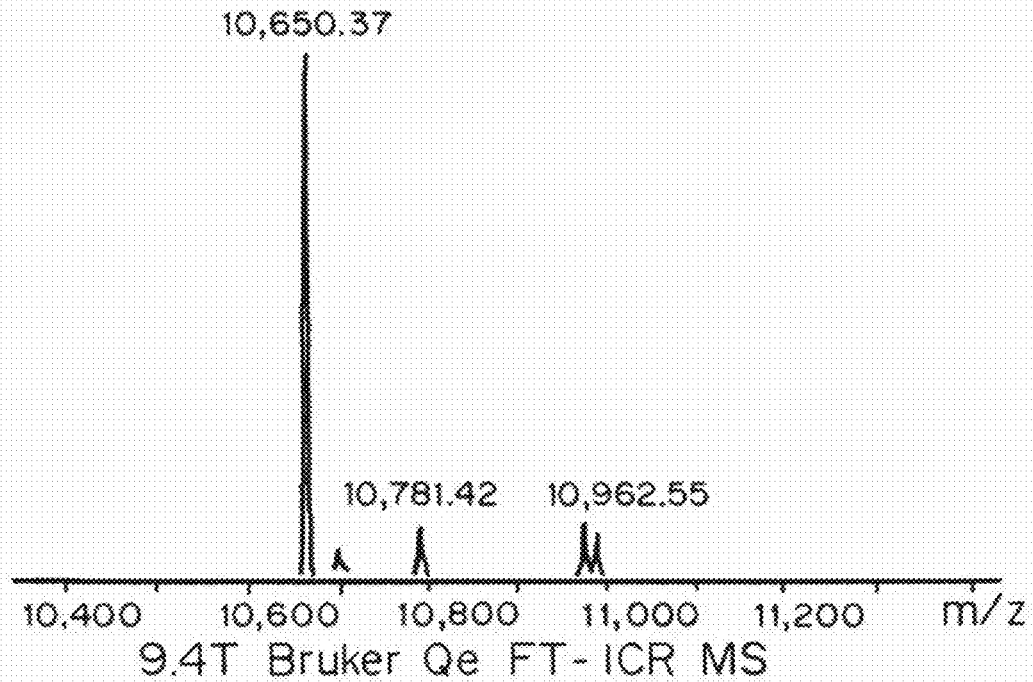
Figure 9B:
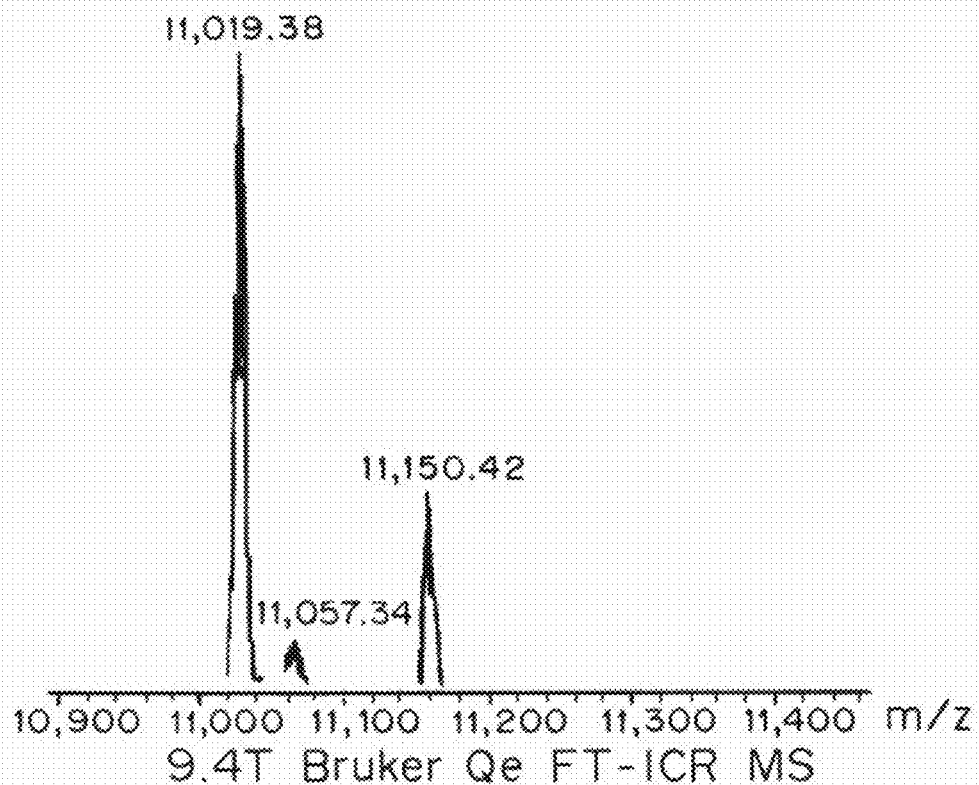

FIGS. 9A and 9B are spectrograms showing the results of Fourier transform ion cyclotron resonance (FT-ICR) mass spectrometry of Grx1$_{C11S/C14S}$ (calculated: 10,650 Da. found 10,651 Da) (FIG. 9A) and Grx1$_{C11am/C14S}$ calculated: 11,019 Da. found 11,019 Da) (FIG. 9B).

Figure 10:
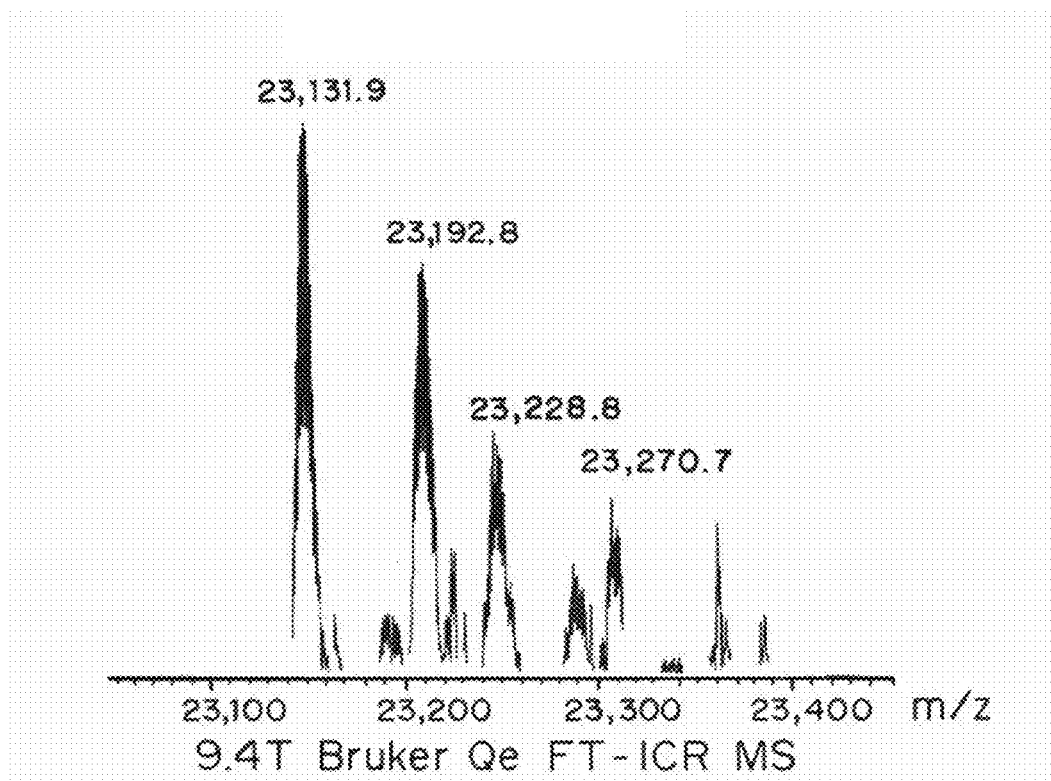

FIG. 10 is a spectrogram showing the results of Fourier transform ion cyclotron resonance (FT-ICR) mass spectrometry of GPx1am.

Figure 11A:
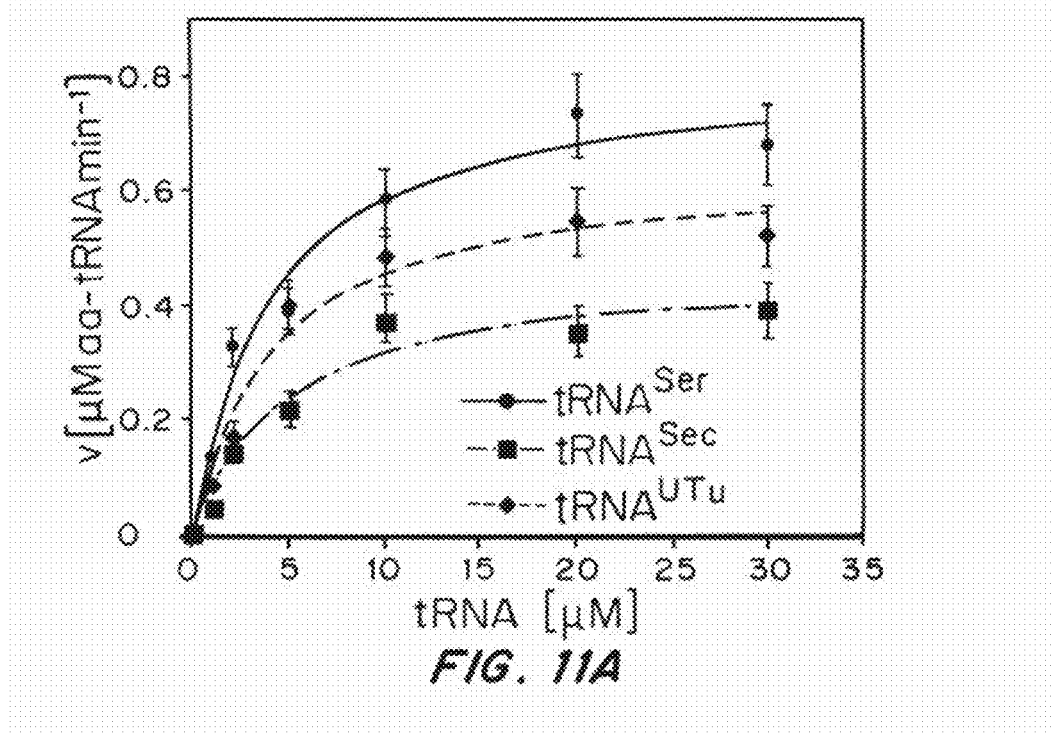
Figure 11B:
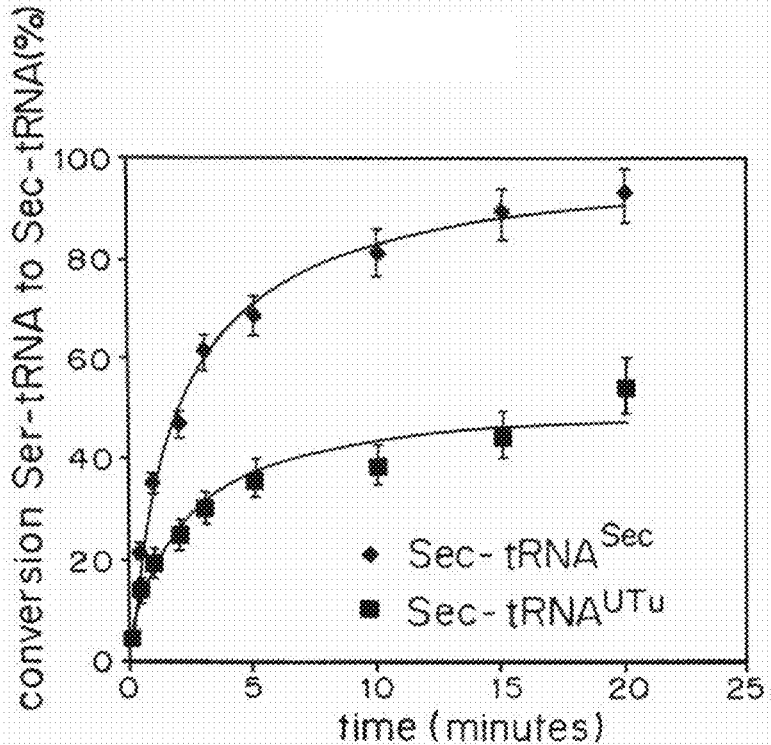

FIG. 11A is a line graph showing varying concentrations (1-30 μM) of tRNA$^{Ser}$ (-●-) tRNA$^{Sec}$ (-■-), and tRNA$^{UTu}$ (-♦-) in an assay for measuring kinetic parameter of each tRNA as a substrate for SerRS (v[μM aa-tRNAmin$^-$]). Kinetic parameters were determined by Michaelis & Menten plots of the initial aminoacylation velocity versus substrate concentration. FIG. 11B is a line graph showing in vitro conversion of tRNA$^{Sec}$ (-♦-) and tRNA$^{UTu}$ (-■-) (Ser-tRNA to Sec-tRNA %) by SelA as a function of time (min).

Figure 12:
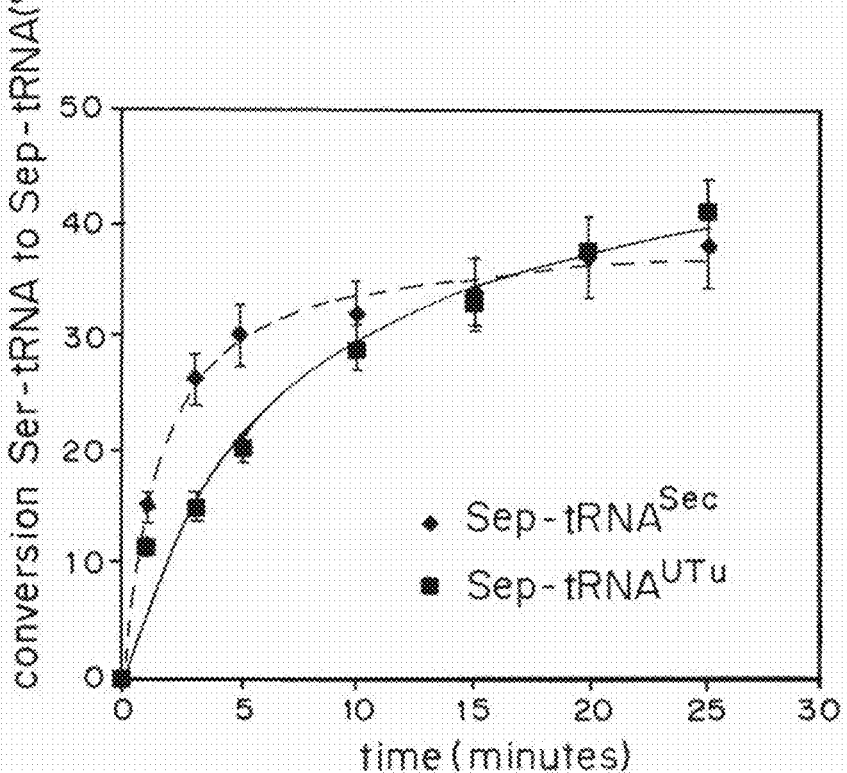

FIG. 12 is a line graph showing in vitro conversion of tRNA$^{Sec}$ (-♦-) and tRNA$^{UTu}$ (-■-) (Ser-tRNA to Sep-tRNA %) by PSTK as a function of time (min).

Figures 13A, 13B:
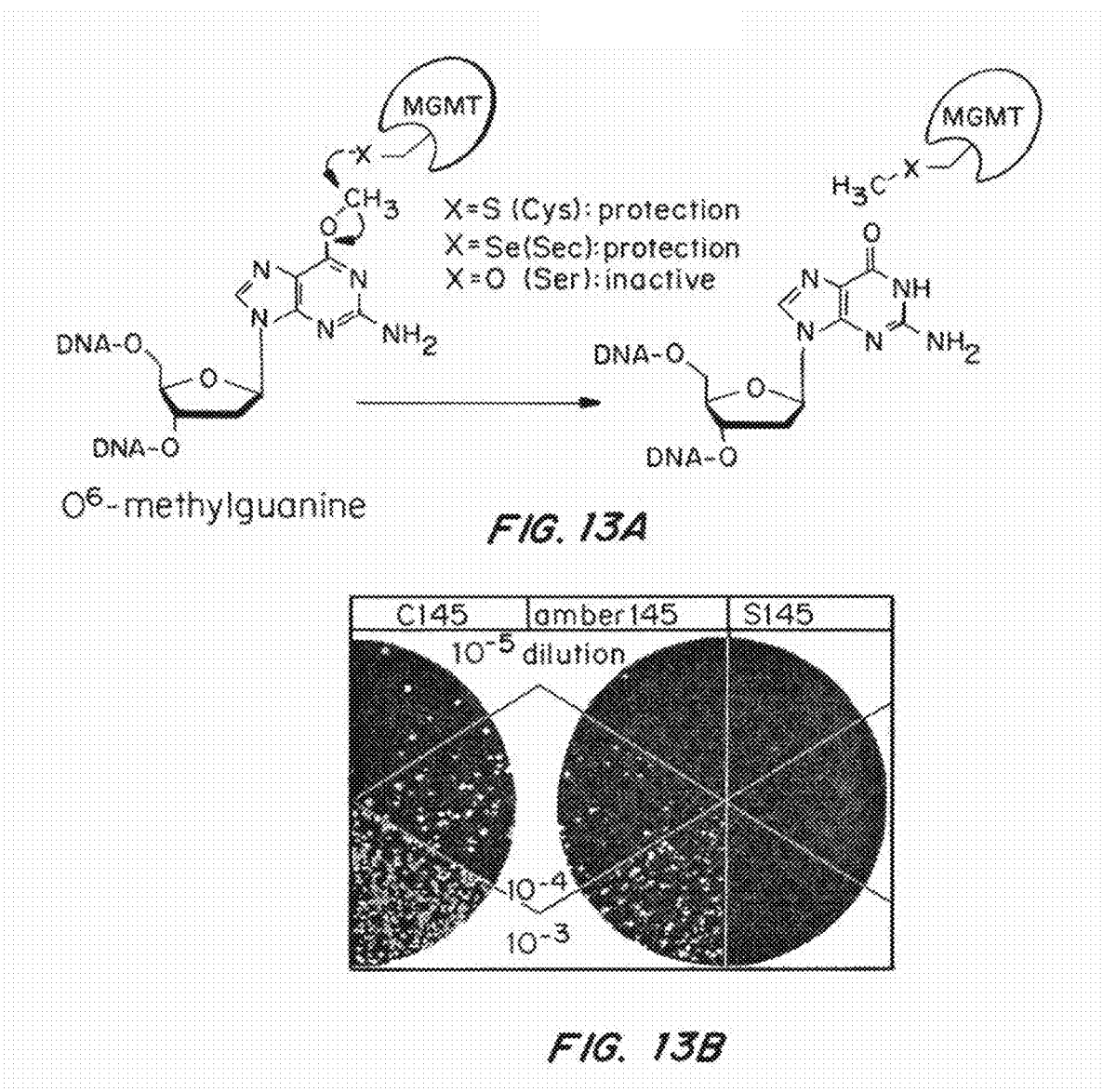

FIG. 13A is a structure diagram showing the activity of various O-6-methylguanine-DNA methyltransferase (MGMT) constructs on O6-methylguanine. FIG. 13B is an image showing the activity (in number of living colonies) of *E. coli* Δada Δotg-1 cells expressing either MGMT C145, amber145 (Sec/Ser) or S145 mutant proteins, and tRNA$^U$-$_{Tu}$amber, pulsed 3× with N-Methyl-N-nitroso-N'-nitroguanidine.

Figure 14:
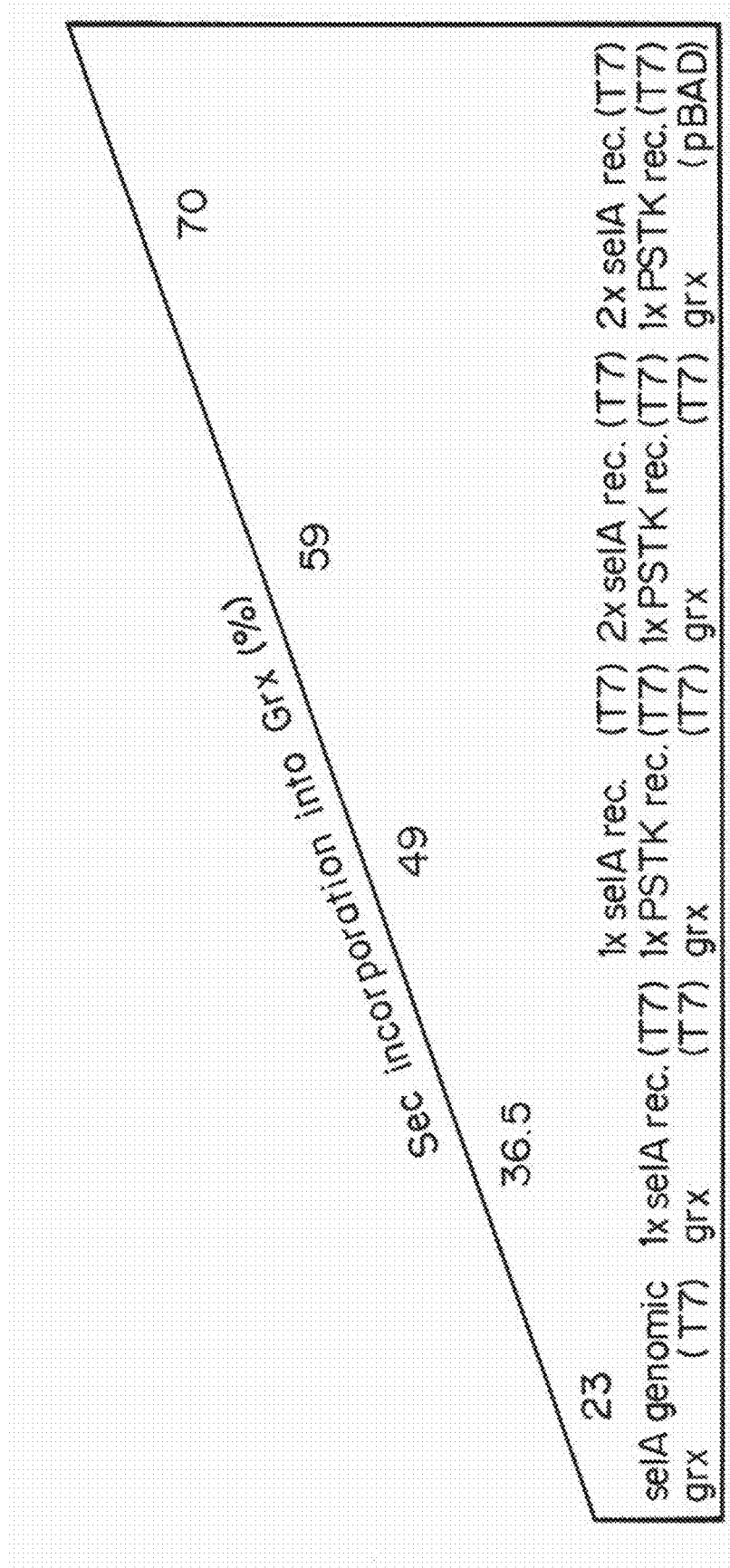

FIG. 14 is a diagram showing genomic factors in *E. coli* that increase Sec incorporation into the recombinantly expressed selenocysteine containing protein Grx (%).

Figure 15A:
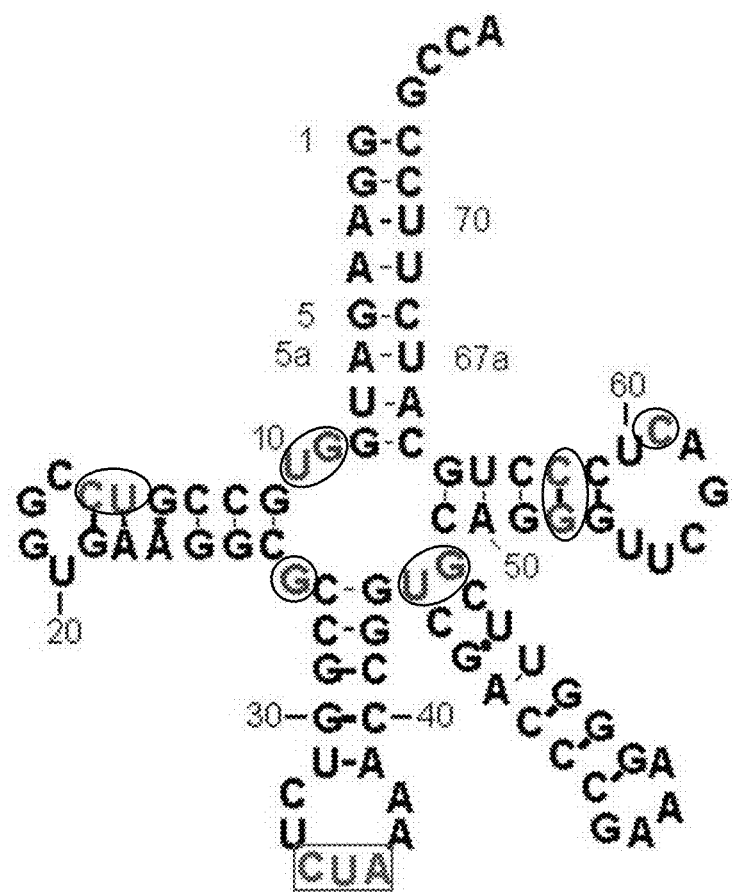
Figure 15B:
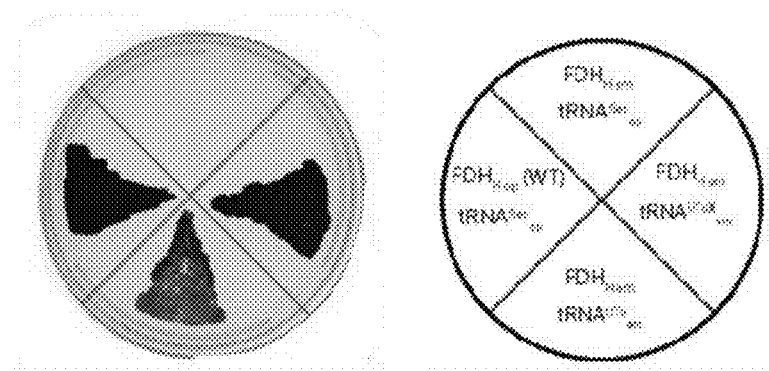
Figure 15C:
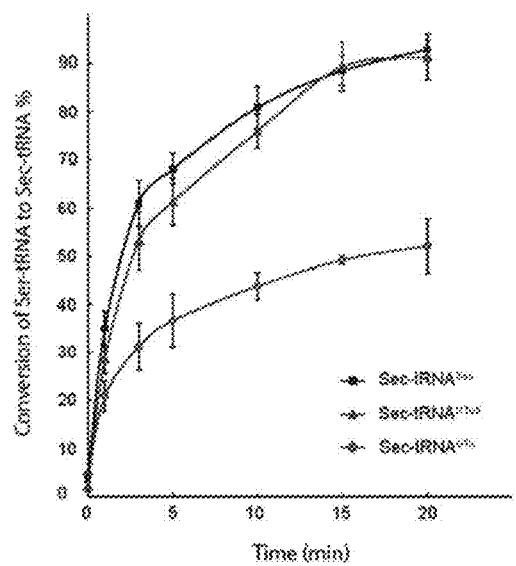

FIG. 15A is a depiction of the primary and secondary structures of a non-naturally occurring tRNA$^{UTuX}$ (SEQ ID NO:59). Nucleotides that were changed from the original tRNA$^{UTu}$ (SEQ ID NO:7) are circled and the amber anticodon is boxed. Specific mutations introduced between tRNA$^{UTu}$ and tRNA$^{UTuX}$ include U8G, G9U, and A27G in the core region; A14U and G15C in the D-arm; deletion of U21 in the D-loop; A52G and U62C in the T-arm; A59C in the T-loop; and the insertion of residues U44 and G48 in the variable arm. FIG. 15B is a photograph and associated schematic illustrating functional Sec insertion in FDH$_H$ by tRNA$^{UTuX}$. As illustrated in the schematic, *E. coli* ΔselA ΔselB ΔfdhF triple deletion strain was separately complemented with *E. coli* SelA, *M. jannaschii* PSTK alongside tRNA$^{Sec}_{op}$, *E. coli* SelB, and WT FDH$_{H140op}$; tRNA$^{UTu}_{am}$ and FDH$_{H140am}$; tRNA$^{UTuX}_{am}$ and FDH$_{H140am}$; and a negative control with tRNA$^{Sec}_{op}$, *E. coli* SelB, and FDH$_{H140am}$. FDH$_H$ activity was assessed by appearance of the purple-colored reduced BV. FIG. 15C is a graph showing in vitro conversion of Ser-tRNA$^{Sec}$, Ser-tRNA$^{UTu}$, and Ser-tRNA$^U$-$_{TuX}$ by SelA.

Figures 16A, 16B, 16C, 16D, 16E, 16F, 16G, 16H:
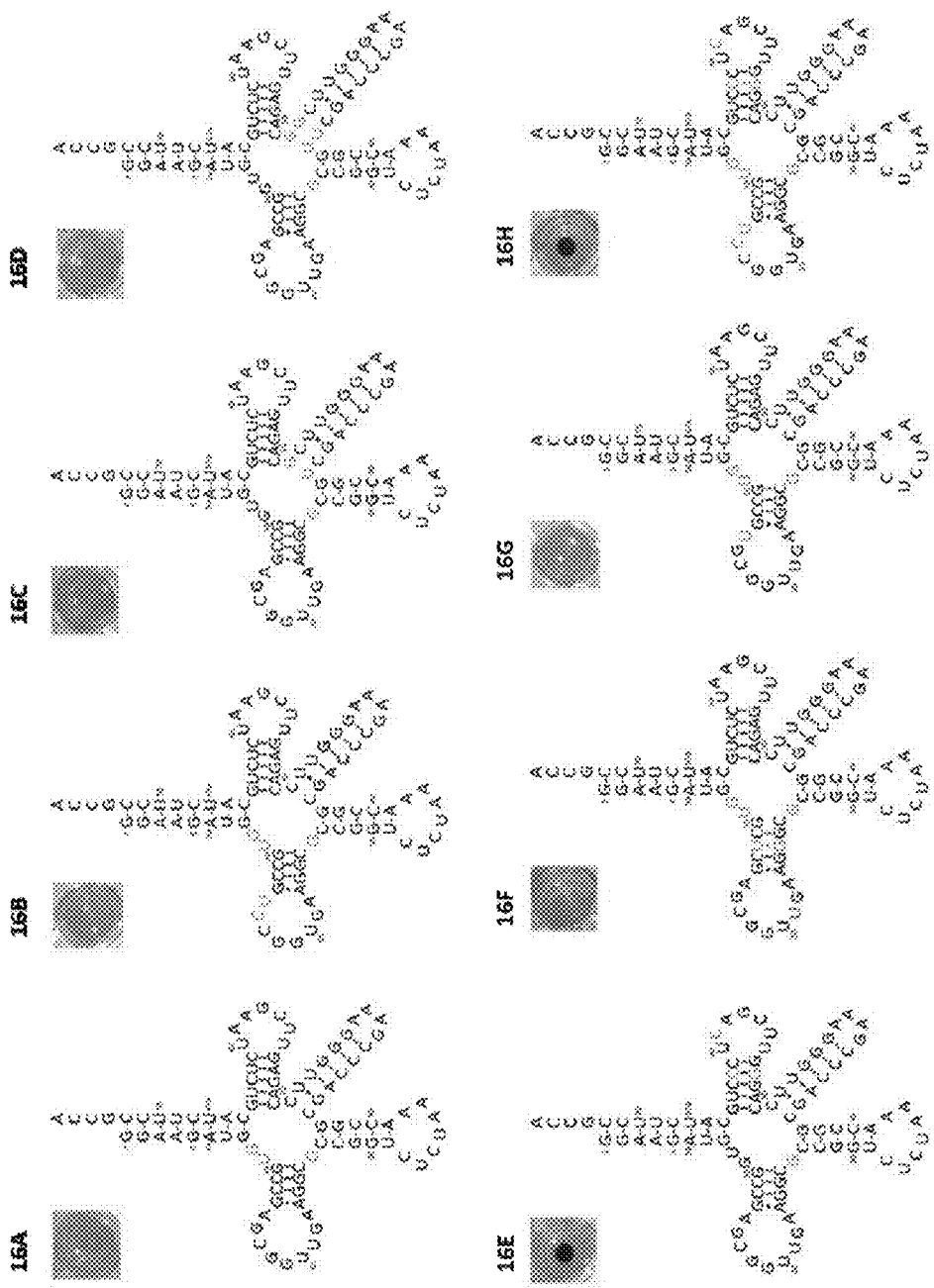
Figures 16I, 16J, 16K, 16L, 16M, 16N, 16O:
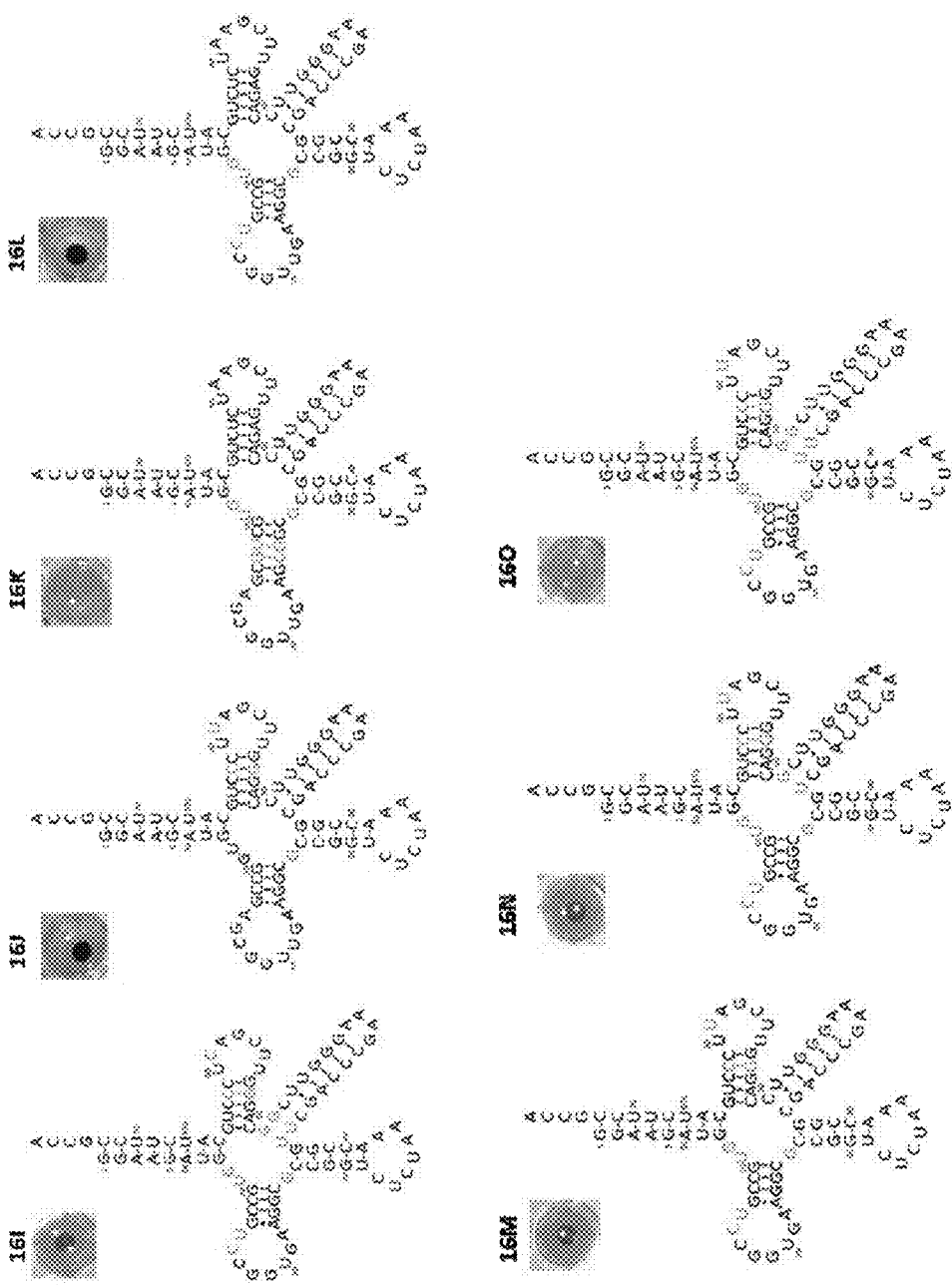
Figure 16Q:
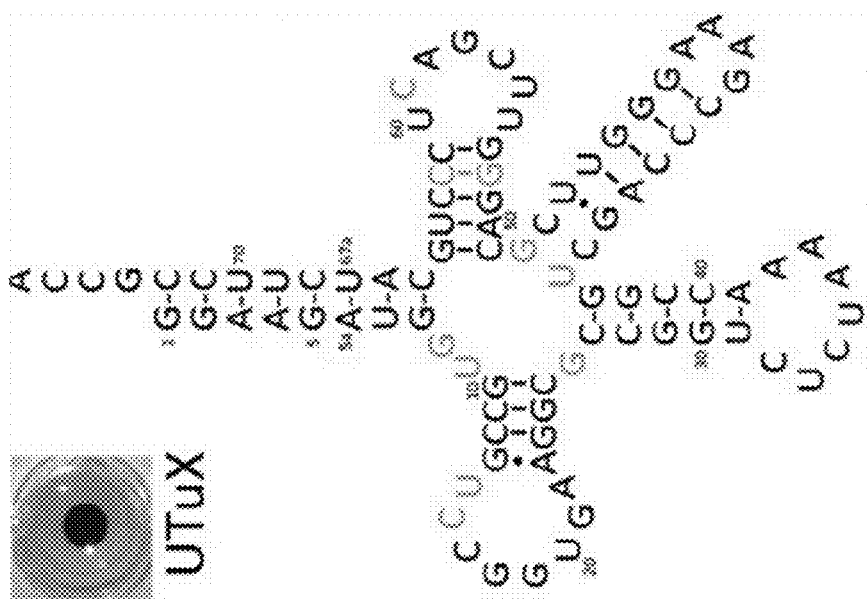
Figure 16P:
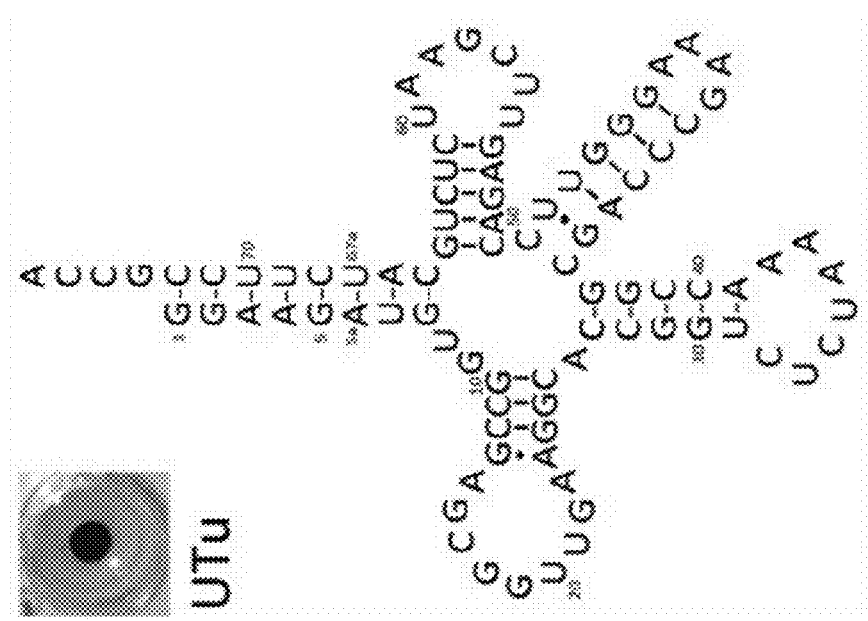

FIGS. 16A-16Q photographs showing the activity adjacent to a depiction of the primary and secondary structures of rationally designed tRNA$^{UTu}$ variants. For each of the sixteen variants shown: variant A (16A, SEQ ID NO:60), variant B (16B, SEQ ID NO:86), variant C (16C, SEQ ID NO:87), variant D (16D, SEQ ID NO:88), variant E (16E, SEQ ID NO:61), variant F (16F, SEQ ID NO:89), variant G (16G, SEQ ID NO:90), variant H (16H, SEQ ID NO:62), variant I (16I, SEQ ID NO:63), variant J (16J, SEQ ID NO:64), variant K (16K, SEQ ID NO:91), variant L (16L, SEQ ID NO:65), variant M (16M, SEQ ID NO:66), variant N (16N, SEQ ID NO:67), variant O (16O, SEQ ID NO:92), UTu (16P, SEQ ID NO:7), and UTuX (16Q, SEQ ID NO:59). Each variant as well as *E. coli* SelB and SelA was used to complement FDH$_{H140am}$ in strain MH5 *E. coli* (ΔselA ΔselB DfdhF). FDH$_H$ activity was assessed by appearance of the purple colored reduced BV, with the activity mediated by each variant shown adjacent to it.

Figure 17:
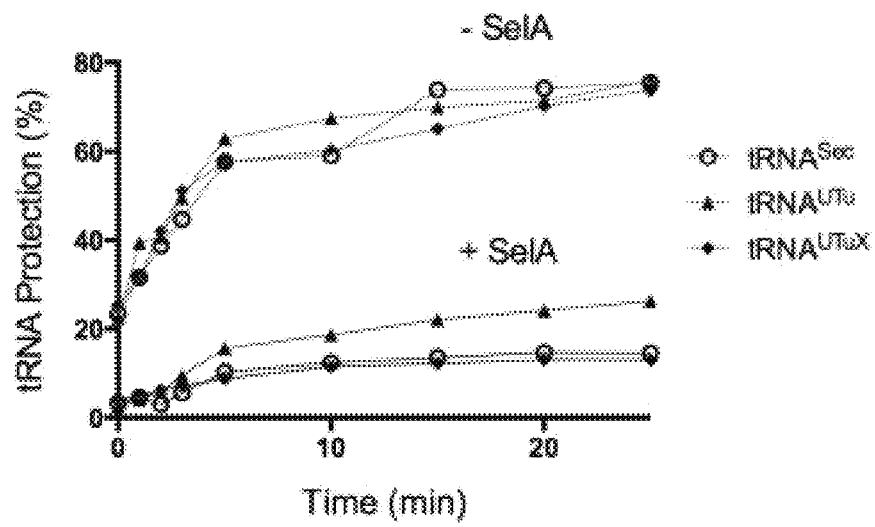

FIG. 17 is a line graph showing nuclease protection of Ser-tRNA variants by SelA. Ser-tRNA$^{Sec}$, Ser-tRNA$^{UTu}$ and Ser-tRNA$^{UTuX}$ samples were incubated in the presence or absence of excess SelA, followed by addition of nuclease P1, and monitored over time using thin layer chromatography (TLC) followed by autoradiography.

Figure 18A:
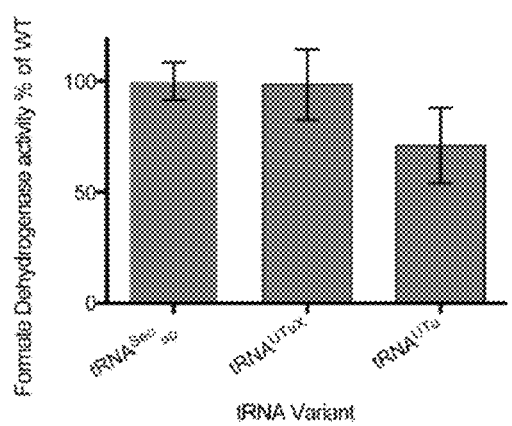
Figure 18B:
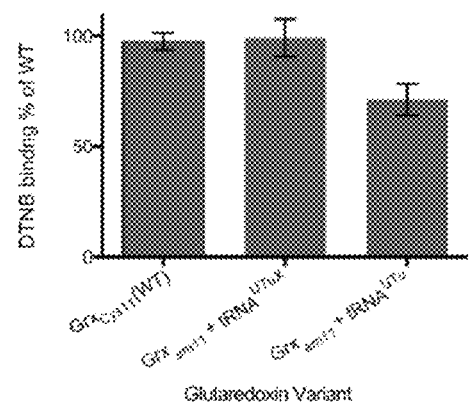

FIG. 18A is a bar graph showing Sec-dependent in vitro BV reduction of recombinant purified FDHH variants. 100 nM each of WT FDH$_{H140op}$ and FDH$_{H140am}$ produced with tRNA$^{UTu}$ and tRNA$^{UTuX}$ were assayed in the linear range of the reaction for 5 min. Relative specific activity of FDH$_H$ variants expressed using tRNA$^{Sec}_{op}$, tRNA$^{UTu}$, or tRNA$^{UTuX}$ were determined. FIG. 18B is a bar graphs showing Sec incorporation into recombinant *E. coli* Grx1 variants as determined spectrometrically by assaying DTNB (Ellman's reagent) binding.

FIG. 19A is a bar graph showing the activity of tRNA$^{UTu}_{am}$, tRNA$^{UTuX}_{am}$, and tRNA$^{SecUX}_{am}$-mediated FDH$_{H140am}$ translation in the absence of release factor 1 (while in the presence of RF2 and RF3). Cell-free translation of selenoprotein FDH$_H$ was mediated by different Sec-tRNA variants and cognate fdhF140 mutants under optimized conditions, and FDH$_{H140am}$ activity was monitored through reduction of BV at 578 nm. FIG. 19B is a bar graph showing translation of FDH$_H$ mutants with cognate tRNA variants tRNA$^{Sec}_{am}$, tRNA$^{Sec}_{op}$, tRNA$^{Sec}_{CGU}$, tRNA$^{Sec}_{GCC}$, tRNA$^{Sec}_{CCU}$, and tRNA$^{Sec}_{UCG}$ in the presence of SelB. Absence of activity was confirmed in a negative control reaction prepared with Ser-tRNA$^{Sec}_{am}$ in place of Sec-tRNA$^{Sec}_{am}$, and in a separate negative control prepared with plasmid encoding dihydrofolate reductase (DHFR) in place of fdhF$_{am}$.

Figure 20B:

FIG. 20A is plot showing quantitation of codon recoding with Sec. Activity for FDH$_H$ variants was independently repeated to address questions of precise values for variants FDH$_{H140CGA}$ and FDH$_{H140AGG}$. The relative yield of 64 FDH$_{H140}$NNN variants (WT FDH$_{H140}$UGA=1) is plotted versus specific activity (relative to wild-type FDH$_{H140}$UGA=100%). For activity, yield values, and standard deviations see Bröcker et al (Bröcker, et al., Angew. Chem. Int. Ed. Engl., 53, 319-23 (2014)). Different levels of specific activity observed for the 64 FDHH variants are the result of the partial incorporation of the respective canonical AAs (Bröcker, et al., Angew. Chem. Int. Ed. Engl., 53, 319-23 (2014)). FIG. 20B is a series of photographs showing the capacity of strains containing fdhF$_{140}$AGG and fdhF$_{140}$CGA codons coexpressed with cognate tRNA$^{Sec}$ to recode the indicated codon to Sec as evidenced by an in vivo BV reduction assay.

Figure 21:
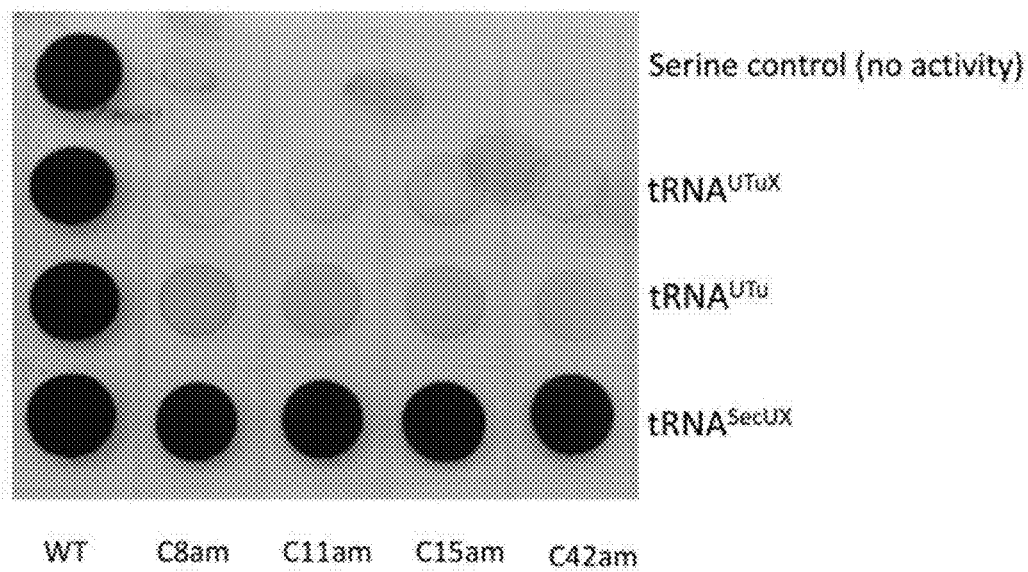

FIG. 21 is a photograph showing the results of an assay measuring selenocysteine insertion at [4Fe-4S] coordinating residues in E. coli FDH$_H$.

DETAILED DESCRIPTION OF THE INVENTION

I. Definitions

Transfer RNA or tRNA refers to a set of genetically encoded RNAs that act during protein synthesis as adaptor molecules, matching individual amino acids to their corresponding codon on a messenger RNA (mRNA). In higher eukaryotes such as mammals, there is at least one tRNA for each of the 20 naturally occurring amino acids. In eukaryotes, including mammals, tRNAs are encoded by families of genes that are 73 to 150 base pairs long. tRNAs assume a secondary structure with four base paired stems known as the cloverleaf structure. The tRNA contains a stem and an anticodon. The anticodon is complementary to the codon specifying the tRNA's corresponding amino acid. The anticodon is in the loop that is opposite of the stem containing the terminal nucleotides. The 3' end of a tRNA is aminoacylated by a tRNA synthetase so that an amino acid is attached to the 3'end of the tRNA. This amino acid is delivered to a growing polypeptide chain as the anticodon sequence of the tRNA reads a codon triplet in an mRNA.

As used herein "suppressor tRNA" refers to a tRNA that alters the reading of a messenger RNA (mRNA) in a given translation system. For example, a suppressor tRNA can read through a stop codon.

As used herein, an "anticodon" refers to a unit made up of any combination of 2, 3, 4, and 5 bases (G or A or U or C), typically three nucleotides, that correspond to the three bases of a codon on an mRNA. Each tRNA contains a specific anticodon triplet sequence that can base-pair to one or more codons for an amino acid or "stop codon." Known "stop codons" include, but are not limited to, the three codon bases, UAA known as ochre, UAG known as amber and UGA known as opal, that do not code for an amino acid but act as signals for the termination of protein synthesis. tRNAs do not decode stop codons naturally, but can and have been engineered to do so. Stop codons are usually recognized by enzymes (release factors) that cleave the polypeptide as opposed to encode an AA via a tRNA. Generally the anticodon loop consists of seven nucleotides. In the 5' to 3' direction the first two positions 32 and 33 precede the anticodon positions 34 to 36 followed by two nucleotides in positions 37 and 38 (Alberts, B., et al. in The Molecular Biology of the Cell, 4$^{th}$ ed, Garland Science, New York, N.Y. (2002)). The size and nucleotide composition of the anticodon is generally the same as the size of the codon with complementary nucleotide composition. A four base pair codon consists of four bases such as 5'-AUGC-3' and an anticodon for such a codon would complement the codon such that the tRNA contained 5'-GCAU-3' with the anticodon starting at position 34 of the tRNA. A 5 base codon 5'-CGGUA-3' codon is recognized by the 5'-UACCG-3' anticodon (Hohsaka T., et al. Nucleic Acids Res. 29:3646-3651 (2001)). The composition of any such anticodon for 2 (16=any possible combination of 4 nucleotides), 3 (64), 4 (256), and 5 (1024) base codons would follow the same logical composition. The "anticodon" typically starts at position 34 of a canonical tRNA, but may also reside in any position of the "anti-codon stem-loop" such that the resulting tRNA is complementary to the "stop codon" of equivalent and complementary base composition.

As used herein, "tRNA$^{Sec}$" refers to an unaminoacylated tRNA suitable for carrying selenocysteine. Typically the anticodon sequence of the tRNA$^{Sec}$ can recognize or hybridize with an mRNA codon specific for, or designed to encode, a selenocysteine amino acid, for example UGA. In E. coli, the endogenous tRNA$^{Sec}$ is encoded by the selC gene.

As used herein, "tRNA$^{Ser}$" refers to an unaminoacylated tRNA suitable for carrying serine. Typically the anticodon sequence of the tRNA$^{Ser}$ can recognize or hybridize with an mRNA codon specific for, or designed to encode, a serine amino acid, for example UCU, UCC, UCA, UCG, AGU, or AGC.

As used herein, "tRNA$^{UTu}$" refers to a non-naturally occurring, unaminoacylated tRNA$^{Sec}$ suitable for carrying selenocysteine. Typically the anticodon sequence of the tRNA$^{UTu}$ can recognize or hybridize with an mRNA codon specific for, or designed to encode, a selenocysteine amino acid.

As used herein, "Sec-tRNA$^{Sec}$" refers to aminoacylated tRNA$^{Sec}$ carrying a selenocysteine amino acid.

As used herein, "Ser-tRNA$^{Sec}$" refers to aminoacylated tRNA$^{Sec}$ carrying a serine amino acid.

As used herein, "Ser-tRNA$^{Ser}$" refers to aminoacylated tRNA$^{Sec}$ carrying a serine amino acid.

As used herein, "Sep-tRNA$^{Ser}$" refers to a phosphorylated Ser-tRNA$^{Sec}$.

As used herein, "EF-Tu" refers to Elongation Factor Thermo Unstable, a prokaryotic elongation factor mediates the entry of the aminoacyl-tRNA into a free site of the ribosome.

As used herein, "SerRS" refers to Seryl-tRNA synthetase (also known as Serine-tRNA ligase) which is a prokaryotic factor that catalyzes the attachment of serine to tRNA$^{Ser}$.

As used herein "SECIS" refers to a SElenoCysteine Insertion Sequence, is an RNA element around 60 nucleotides in length that adopts a stem-loop structure which directs the cell to translate UGA codons as selenocysteines. In bacteria the SECIS can be soon after the UGA codon it affects, while in archaea and eukaryotes, it can be in the 3' or 5' UTR of an mRNA, and can cause multiple UGA codons within the mRNA to code for selenocysteine.

As used herein "SelA" refers to selenocysteine synthase, a prokaryotic pyridoxal 5-phosphate-containing enzyme which catalyzes the conversion of Ser-tRNA$^{Sec}$ into a Sec-tRNA$^{Sec}$.

As used herein "SelB" refers to selenocysteine-specific elongation factor, a prokaryotic elongation factor for delivery of Sec-tRNA$^{Sec}$ to the ribosome.

As used herein "PSTK" refers to phosphoseryl-tRNA kinase (also known as O-phosphoseryl-tRNA$^{Sec}$ kinase and L-seryl-tRNA$^{Sec}$ kinase), a kinase that phosphorylates Ser-tRNA$^{Sec}$ to O-phosphoseryl-tRNA$^{Sec}$, an activated intermediate for selenocysteine biosynthesis.

As used herein "SepSecS" refers to Sep (O-phosphoserine) tRNA: Sec (selenocysteine) tRNA synthase (also known as O-phosphoseryl-tRNA(Sec) selenium transferase and Sep-tRNA:Sec-tRNA synthase), an eukaryotic and archaeal enzyme that converts O-phosphoseryl-tRNA$^{Sec}$ to selenocysteinyl-tRNA$^{Sec}$ in the presence of a selenium donor.

As used herein SepCysS refers to Sep-tRNA:Cys-tRNA synthase, an archaeal/eukaryotic enzyme that converts O-phosphoseryl-tRNA$^{Cys}$ (Sep-tRNA$^{Cys}$ into Cys-tRNA$^{Cys}$ in the presence of a sulfur donor.

As used herein "G-C content" (or guanine-cytosine content) refers to the percentage of nitrogenous bases on a nucleic acid molecule, or fragment, section, or region thereof, that are either guanine or cytosine.

Aminoacyl-tRNA Synthetases ("AARS") are enzymes that charge (acylate) tRNAs with amino acids. These charged aminoacyl-tRNAs then participate in mRNA translation and protein synthesis. The AARS show high specificity for charging a specific tRNA with the appropriate amino acid, for example, tRNA$^{Val}$ with valine by valyl-tRNA synthetase or tRNA$^{Trp}$ with tryptophan by tryptophanyl-tRNA synthetase. In general, there is at least one AARS for each of the twenty amino acids.

As used herein "translation system" refers to the components necessary to incorporate a naturally occurring amino acid into a growing polypeptide chain (protein). Components of a translation system can include, e.g., ribosomes, tRNAs, synthetases, mRNA and the like. The components described herein can be added to a translation system, in vivo or in vitro. A translation system can be either prokaryotic, e.g., an *E. coli* cell, or eukaryotic, e.g., a yeast, mammal, plant, or insect or cells thereof.

A "transgenic organism" as used herein, is any organism, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. Suitable transgenic organisms include, but are not limited to, bacteria, cyanobacteria, fungi, plants and animals. The nucleic acids described herein can be introduced into the host by methods known in the art, for example infection, transfection, transformation or transconjugation. Techniques for transferring DNA into such organisms are widely known and provided in references such as Sambrook, et al. (2000) Molecular Cloning: A Laboratory Manual, 3$^{rd}$ ed., vol. 1-3, Cold Spring Harbor Press, Plainview N.Y.

As used herein, the term "eukaryote" or "eukaryotic" refers to organisms or cells or tissues derived therefrom belonging to the phylogenetic domain Eukarya such as animals (e.g., mammals, insects, reptiles, and birds), ciliates, plants (e.g., monocots, dicots, and algae), fungi, yeasts, flagellates, microsporidia, and protists.

As used herein, the term "non-eukaryotic organism" refers to organisms including, but not limited to, organisms of the Eubacteria phylogenetic domain, such as *Escherichia coli*, *Thermus thermophilus*, and *Bacillus stearothermophilus*, or organisms of the Archaea phylogenetic domain such as, *Methanocaldococcus jannaschii*, *Methanothermobacter thermautotrophicus*, *Halobacterium* such as *Haloferax volcanii* and *Halobacterium* species NRC-1, *Archaeoglobus fulgidus*, *Pyrococcus furiosus*, *Pyrococcus horikoshii*, and *Aeuropyrum pernix*.

The term "construct" refers to a recombinant genetic molecule having one or more isolated polynucleotide sequences. Genetic constructs used for transgene expression in a host organism include in the 5'-3' direction, a promoter sequence; a sequence encoding a gene of interest; and a termination sequence. The construct may also include selectable marker gene(s) and other regulatory elements for expression.

The term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory regions and can include 5' and 3' ends.

The term "orthologous genes" or "orthologs" refer to genes that have a similar nucleic acid sequence because they were separated by a speciation event.

The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Cofactor", as used herein, refers to a substance, such as a metallic ion or a coenzyme that must be associated with an enzyme for the enzyme to function. Cofactors work by changing the shape of an enzyme or by actually participating in the enzymatic reaction.

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamnine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "isolated" is meant to describe a compound of interest (e.g., nucleic acids) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. Isolated nucleic acids are at least 60% free, preferably 75% free, and most preferably 90% free from other associated components.

The term "vector" refers to a replicon, such as a plasmid, phage, or cosmid, into which another DNA segment may be inserted so as to bring about the replication of the inserted segment. The vectors can be expression vectors.

The term "expression vector" refers to a vector that includes one or more expression control sequences The term "expression control sequence" refers to a DNA sequence that controls and regulates the transcription and/or translation of another DNA sequence. Control sequences that are suitable for prokaryotes, for example, include a promoter, optionally an operator sequence, a ribosome binding site, and the like. Eukaryotic cells are known to utilize promoters, polyadenylation signals, and enhancers.

"Transformed," "transgenic," "transfected" and "recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g., a bacterium or plant, which does not contain the heterologous nucleic acid molecule.

The term "endogenous" with regard to a nucleic acid refers to nucleic acids normally present in the host.

The term "heterologous" refers to elements occurring where they are not normally found. For example, a promoter may be linked to a heterologous nucleic acid sequence, e.g., a sequence that is not normally found operably linked to the promoter. When used herein to describe a promoter element, heterologous means a promoter element that differs from that normally found in the native promoter, either in sequence, species, or number. For example, a heterologous control element in a promoter sequence may be a control/regulatory element of a different promoter added to enhance promoter control, or an additional control element of the same promoter. The term "heterologous" thus can also encompass "exogenous" and "non-native" elements.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

The term "stringent hybridization conditions" as used herein mean that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared carrier DNA such as salmon sperm DNA, followed by washing the hybridization support in 0.1×SSC at approximately 65° C. Other hybridization and wash conditions are well known and are exemplified in Sambrook et al, Molecular Cloning: A Laboratory Manual, Third Edition, Cold Spring Harbor, N.Y. (2000).

As used herein, the term "low stringency" refers to conditions that permit a polynucleotide or polypeptide to bind to another substance with little or no sequence specificity.

As used herein, the term "purified" and like terms relate to the isolation of a molecule or compound in a form that is substantially free (at least 60% free, preferably 75% free, and most preferably 90% free) from other components normally associated with the molecule or compound in a native environment.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the terms "recoded organism" and "genomically recoded organism (GRO)" in the context of codons refer to an organism in which the genetic code of the organism has been altered such that a codon has been eliminated from the genetic code by reassignment to a synonymous or nonsynonymous codon.

Unless otherwise indicated, the disclosure encompasses conventional techniques of molecular biology, microbiology, cell biology and recombinant DNA, which are within the skill of the art. See, e.g., Sambrook and Russell, Molecular Cloning: A Laboratory Manual, 3rd edition (2001); Current Protocols In Molecular Biology [(F. M. Ausubel, et al. eds., (1987)]; Coligan, Dunn, Ploegh, Speicher and Wingfeld, eds. (1995) Current Protocols in Protein Science (John Wiley & Sons, Inc.); the series Methods in Enzymology (Academic Press, Inc.): PCR 2: A Practical Approach (M. J. MacPherson, B. D. Hames and G. R. Taylor eds. (1995)].

Unless otherwise noted, technical terms are used according to conventional usage. Definitions of common terms in molecular biology may be found in Lewin, Genes VII, published by Oxford University Press, 2000; Kendrew et al. (eds.), The Encyclopedia of Molecular Biology, published by Wiley-Interscience., 1999; and Robert A. Meyers (ed.), Molecular Biology and Biotechnology, a Comprehensive Desk Reference, published by VCH Publishers, Inc., 1995; Sambrook and Russell. (2001) Molecular Cloning: A Laboratory Manual 3rd. edition, Cold Spring Harbor Laboratory Press.

II. Compositions

A. tRNA

Non-naturally occurring tRNA$^{Sec}$ suitable for carrying selenocysteine and facilitating synthesis of selenopeptides without requiring a SECIS in the mRNA encoding the peptide are disclosed. Also disclosed are aminoacylated non-naturally occurring tRNA$^{Sec}$. Using the methods discussed in more detail below, the tRNA$^{Sec}$ disclosed herein are capable of being aminoacylated to form a Sec-tRNA$^{Sec}$ which can facilitate insertion of selenocysteine into nascent polypeptide chains. Typically, the non-naturally occurring tRNA$^{Sec}$ (1) can be recognized by SerRS and by EF-Tu, or variants thereof; and is characterized by one or more of the following elements: (2) when aminoacylated with serine the non-naturally occurring Ser-tRNA$^{Sec}$ can be converted to non-naturally occurring Sec-tRNA$^{Sec}$ by SelA, or variant thereof, (3) when aminoacylated with serine the non-naturally occurring Ser-tRNA$^{Sec}$ can be phosphorylated by PSTK or variant thereof, (4) when aminoacylated with phosphorylated serine the non-naturally occurring Sep-tRNA$^{Sec}$ can serve as a substrate for SepSecS or variant thereof; and combinations thereof. In some embodiments, the non-naturally occurring tRNA$^{Sec}$ is characterized by elements (1) and (2). In some embodiments, the non-naturally occurring tRNA$^{Sec}$ is characterized by elements (1), (3), and (4). In some embodiments, the non-naturally occurring tRNA$^{Sec}$ is characterized by elements (1), (2), (3), and (4). Typically, the non-naturally occurring Sec-tRNA$^{Sec}$ can be bound by EF-Tu. The Sec can be incorporated into a growing peptide chain at a codon of the mRNA that recognizes the anticodon of the tRNA$^{Sec}$. Preferably, EF-Tu does not bind Sep-tRNA$^{Sec}$. In some embodiments, EF-Tu is less efficient at incorporating Ser-tRNA$^{Sec}$ than Sec-tRNA$^{Sec}$ into the growing peptide chain.

Typically, the non-naturally occurring tRNA$^{Sec}$ do not require a SECIS element in an mRNA to be incorporated into a growing polypeptide chain during translation. Typically the anticodon of the non-naturally occurring tRNA$^{Sec}$ is recognized or hybridizes to a stop codon. Typically the non-naturally occurring tRNA$^{Sec}$ can facilitate incorporation of a Sec into a growing peptide chain without the activity of SelB.

1. Substrates for EF-Tu

EF-Tu is a prokaryotic elongation factor that mediates the entry of the aminoacyl-tRNA into a free site of the ribosome. Endogenous prokaryotic tRNAs, typically include an anti-determinant element, which prevents recognition of a SectRNA$^{Sec}$ by the elongation factor EF-Tu. In some embodiments, the disclosed tRNA can be a substrate for EF-Tu. Therefore, in some embodiments, the disclosed tRNA is a variant of an endogenous tRNA$^{Sec}$ that has been modified to inactivate the antideterminant element. The antideterminant element can be modified, mutated, or deleted so that tRNA is an acceptable substrate for EF-Tu. For example the antideterminant element in *E. coli* tRNA$^{Sec}$ is located in the 8th, 9th and 10th by in the acceptor branch of tRNA$^{Sec}$ (encoded by selC), corresponding to the last base pair in the amino acid acceptor stem and the two first pairs in the T-stem (Rudinger, et al., *EMBO J.*, 15(3):650-57 (1996), and can be referred to as C7•G66/G49•U65/C50•G64 according the numbering in Schon, et al., *Nucleic Acids Res.*, 17(18): 7159-7165 (1989). Accordingly, in some embodiments, the non-naturally occurring tRNA$^{Sec}$ is a naturally occurring tRNA$^{Sec}$ where the corresponding antideterminant sequence is mutated or deleted such that the non-naturally occurring tRNA$^{Sec}$ is a substrate for EF-Tu.

2. Substrates for PSTK

PSTK is a kinase in archaeal and eukaryotic systems that phosphorylates Ser-tRNA$^{Sec}$ to O-phosphoseryl-tRNA$^{Sec}$, an activated intermediate for selenocysteine biosynthesis. Accordingly, in some embodiments, once aminoacylated with serine, the non-naturally occurring tRNA can serve as a substrate for a PSTK, or variant thereof. The enzyme activity of PSTK is strictly tRNA$^{Sec}$-dependent. PSTK does not hydrolyze ATP in the absence of tRNA nor in the presence of Ser-tRNA$^{Ser}$. The binding of tRNA$^{Ser}$, however, promotes ATP hydrolysis (R. Lynn Sherrer, et al., *Nucleic Acids Res.*, 36(4): 1247-1259 (2008)). This indicates that tRNA$^{Sec}$ might play an essential role in positioning the Ser moiety for initiating phosphoryl transfer. Compared to aminoacyl-tRNA synthetases, PSTK has approximately 20-fold higher affinity toward its substrate, Ser-tRNA$^{Sec}$ (Km=40 nM) (R. Lynn Sherrer, et al., *Nucleic Acids Res.*, 36(4): 1247-1259 (2008)), which may compensate for the low abundance of tRNA$^{Sec}$ in vivo. The concentration of tRNA$^{Sec}$ in vivo is at least 10-fold lower than tRNA$^{Ser}$ in tRNA$^{Sec}$-rich tissues such as liver, kidney and testes in rat (Diamond, et al., *J. Biol. Chem.*, 268:14215-14223 (1993)).

The crystal structure of *Methanocaldococcus jannaschii* PSTK (MjPSTK) places archaeal PSTK identity elements (G2:C71 and the C3:G70) (Sherrer, et al., *Nucleic Acids Res*, 36:1871-1880 (2008)). within contact of the protein dimer interface. The second base pair in the acceptor stem is highly conserved as C2:G71 in eukaryotic tRNA$^{Sec}$, and mutation of G2:C71 to C2:G71 in archaeal tRNA$^{Sec}$ resulted in a Ser-tRNA$^{Sec}$ variant that is phosphorylated inefficiently (Sherrer, et al., *Nucleic Acids Res*, 36:1871-1880 (2008). The A5-U68 base pair in *Methanococcus maripaludis* tRNA$^{Ser}$ has some antideterminant properties for PSTK (Sherrer, et al., *NAR*, 36(6):1871-1880 (2008)). Moreover, the eukaryotic PSTK has been reported to recognize the unusual D-arm of tRNA$^{Sec}$ as the major identity element for phosphorylation (Wu and Gross *EMBO J.*, 13:241-248 (1994)). Accordingly, in some embodiments, the disclosed tRNAs include residues in the acceptor stem, the D-arm, or combinations thereof that are necessary for the tRNA to serve as a substrate for a PSTK.

3. Substrate for SepSecS

The conversion of phosphoseryl-tRNA$^{Sec}$ (Sep-tRNA$^{Sec}$) to selenocysteinyl-tRNA$^{Sec}$ (Sec-tRNA$^{Sec}$) is the last step of Sec biosynthesis in both archaea and eukaryotes, and it is catalyzed by tetratmeric O-phosphoseryl-tRNA:selenocysteinyl-tRNA synthase (SepSecS). It is believed that one SepSecS homodimer interacts with the sugar-phosphate backbone of both the acceptor-TΨC and the variable arms of tRNA$^{Sec}$, while the other homodimer interacts specifically with the tip of the acceptor arm through interaction between the conserved Arg398 and the discriminator base G73 of human tRNA$^{Sec}$.

The co-crystal structure of SepSecS and tRNA$^{Sec}$ also suggests that the 9 bp acceptor stem of tRNA$^{Sec}$ is probably important for recognition by the enzyme (Palioura, S, Sherrer, R L, Steitz, T A, Söll, D & Simonovic, M (2009) *Science* 325:321-325). According to structural analysis, the acceptor-T-variable arm elbow region of tRNA$^{Sec}$ (including bases G50, G51, C64, C65 in the human tRNA$^{Sec}$ that are recognized by SepSecS) may be critical for recognition by SepSecS. Accordingly, in some embodiments, the disclosed tRNAs include residues in the acceptor-TΨC, the variable arms of tRNA$^{Sec}$, the tip of the acceptor arm, or combinations thereof necessary for the tRNA to serve as a substrate for SepSecS. In some embodiments, the G50, G51, C64, C65 elements of human tRNA$^{Sec}$ are present in the non-naturally occurring tRNA$^{Sec}$.

The SepSecS enzyme itself can also be mutated to engineer enzyme variants that accept a substrate somewhat less ideal than naturally occurring tRNA$^{Sec}$. It is believed that His30, Arg33, Lys38 in SepSecS form key interactions with the protomer and G50, U51, C64 and C65 of the tRNA. Therefore, mutation of some of these residues could result in a SepSecS variant that is better able to recognize one of the non-naturally occurring tRNA$^{Sec}$. The formed Sec-tRNA$^{Sec}$ can be screened in the formate dehydrogenase-benzyl viologen assay [e.g., (Yuan, J, Palioura, S, Salazar, J C, Su, D, O'Donoghue, P, Hohn, M J, Cardoso, A M, Whitman, W B & Söll, D (2006), *Proc Natl Acad Sci USA* 103:18923-18927; Palioura, S, Sherrer, R L, Steitz, T A, Söll, D & Simonovic, M (2009) *Science* 325:321-325)]. Other assays include standard Wolfson assay [e.g., (Yuan, J, Palioura, S, Salazar, J C, Su, D, O'Donoghue, P, Hohn, M J, Cardoso, A M, Whitman, W B & Söll, D (2006) *Proc Natl Acad Sci USA* 103:18923-18927; Palioura, S, Sherrer, R L, Steitz, T A, Söll, D & Simonovic, M (2009) *Science* 325:321-325)], labeling with [75Se]selenite in the presence of selenophosphate synthase (SelD) [e.g., (Yuan, J, Palioura, S, Salazar, J C, Su, D, O'Donoghue, P, Hohn, M J, Cardoso, A M, Whitman, W B & Söll, D (2006) *Proc Natl Acad Sci USA* 103:18923-18927)], and using [14C] or [3H]serine in the initial charging reaction.

In some embodiments, a SepCysS is used instead of SepSecS. SepCysS is a key PLP-dependent enzyme in Cys-tRNA formation in methanogens. It converts Sep-tRNA$^{Cys}$ into Cys-tRNA$^{Cys}$ using thiophosphate as sulfur donor. The enzyme's crystal structure is established (Fukunaga, R & Yokoyama, S (2007) *Nat Struct Mol Biol* 14:272-279.) and its mechanism (Liu, Y., Dos Santos, P. C., Zhu, X., Orlando, R., Dean, D. R., Söll, D. and Yuan, J. (2012) *J. Biol. Chem.* 287, 5426-5433) is different from that of SepSecS (Palioura, S, Sherrer, R L, Steitz, T A, Söll, D & Simonovic, M (2009) *Science* 325:321-325.). The length of the acceptor stem of its tRNA substrates is not critical and acceptor helices between 7-9 bp are acceptable. Therefore, this enzyme's active site can be engineered to allow selenophosphate (instead of thiophosphate) to participate in the reaction.

Figure 2:
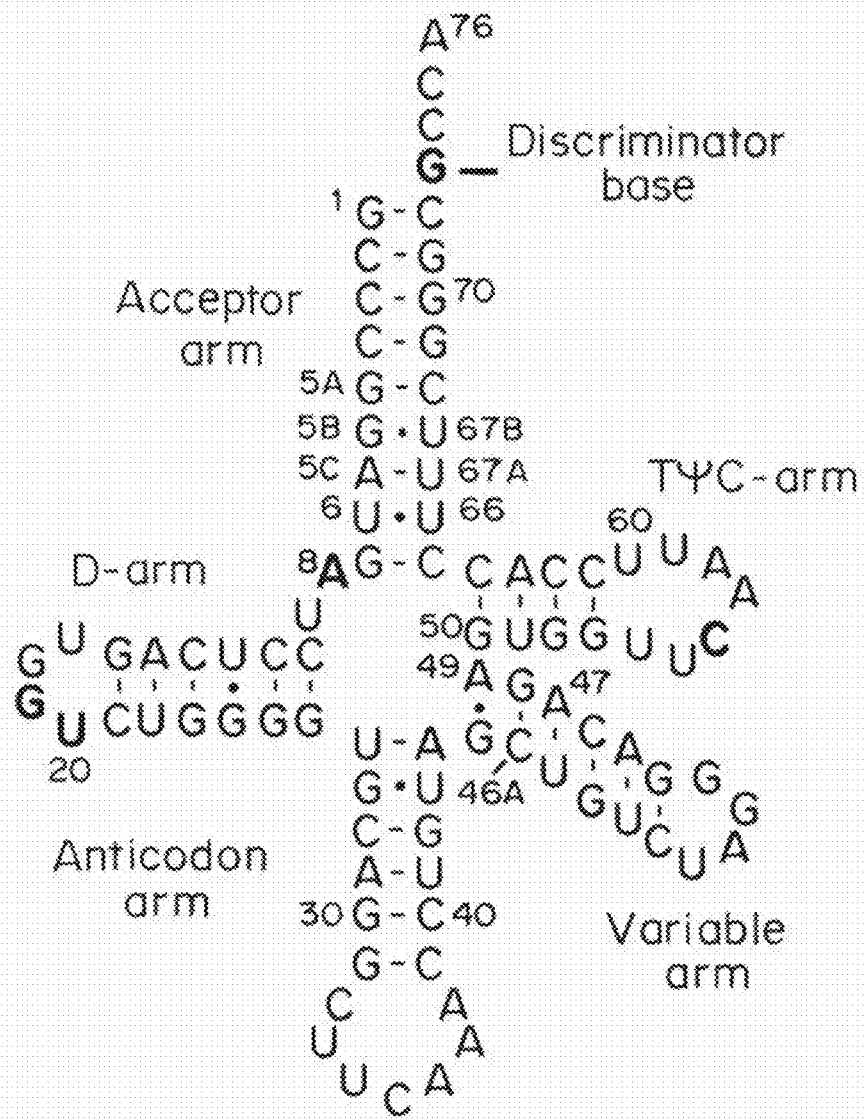
FIG. 2 is a depiction of the primary and secondary structures of human tRNA$^{Sec}$ (SEQ ID NO:3) adapted from Yuan, et al., *FEBS Lett*, 584(2):342-349 (2010).

4. Primary Structure tRNAs can be described according to their primary structure (i.e., the sequence from 5' to 3') as well as their secondary structure. The secondary structure of tRNA is typically referred to as a "cloverleaf", which assumes a 3D L-shaped tertiary structure through coaxial stacking of the helices. FIG. 2 illustrates a typical human tRNA$^{Sec}$, which includes an acceptor arm, a D-arm, an anticodon arm, a variable arm, and a TΨC-arm.

In some embodiments the non-naturally occurring tRNA$^{Sec}$ shares sequence identity or sequence homology with a naturally occurring tRNA, for example a naturally occurring tRNA$^{Sec}$, or a naturally occurring tRNA$^{Sec}$.

a. Variants of Naturally Occurring tRNA$^{Sec}$

The non-naturally occurring tRNA$^{Sec}$ disclosed herein can be a variant of a naturally occurring tRNA$^{Sec}$. The naturally occurring tRNA$^{Sec}$ can be from a prokaryote, including but not limited to E. coli, an archaea, including, but not limited to, M. maripaludis and M. jannaschii, or a eukaryote including, but not limited to human.

In some embodiments, the non-naturally occurring tRNA$^{Sec}$ is a variant of an E. coli tRNA$^{Sec}$, for example, (SEQ ID NO: 1)
GGAAGAUCGUCGUCUCCGGUGAGGCGGCUGGACUUCAAAUCCA

GUUGGGCCGCCAGCGGUCCCGGGCAGGUUCGACUCCUGUGAUC

Figure 3:
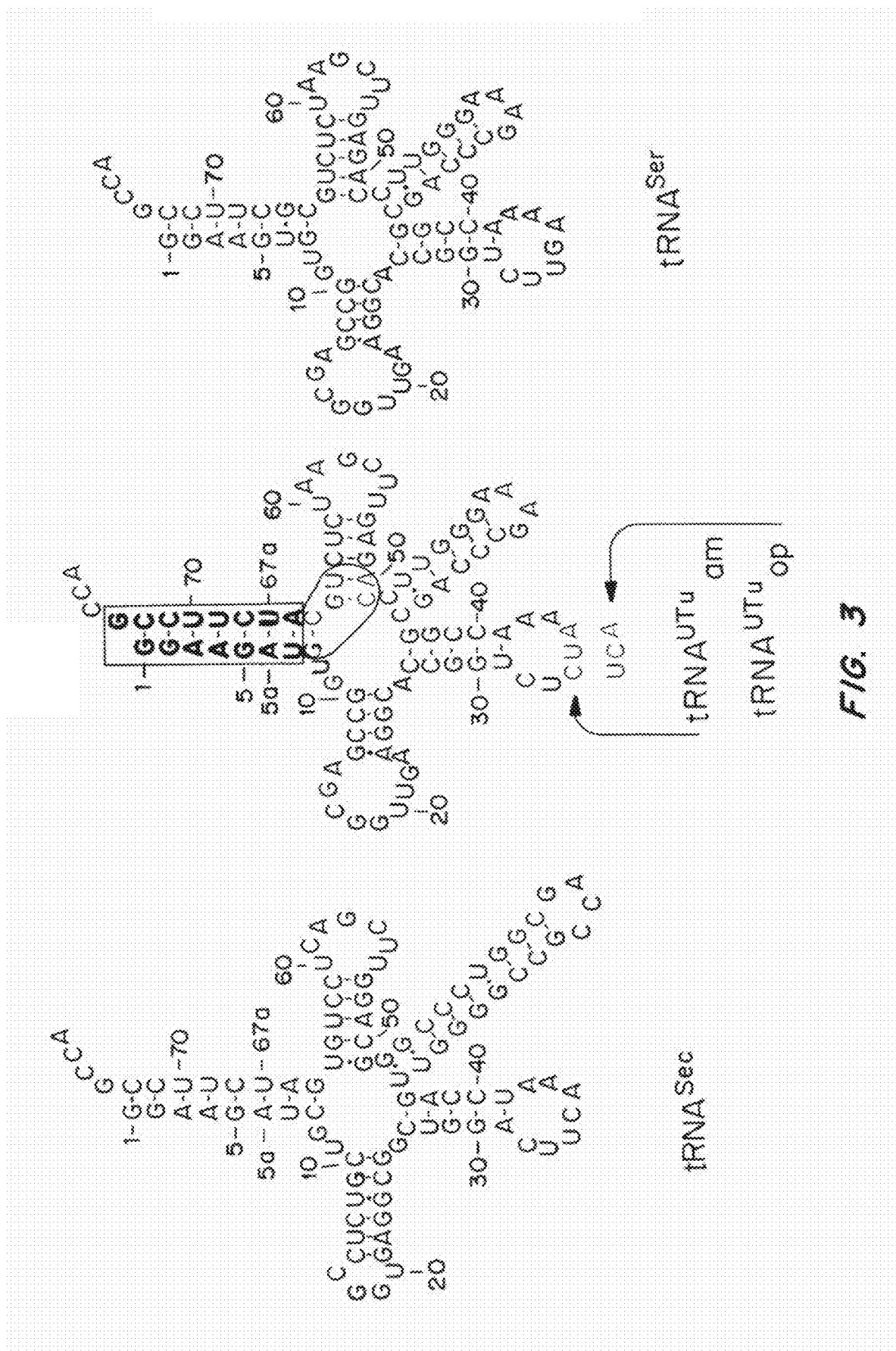
FIG. 3 is a depiction of the primary and secondary structures of E. coli tRNA$^{Sec}$ (left, SEQ ID NO:1), a non-naturally occurring tRNA$^{UTu}$ with an E. coli body (center, (tRNA$^{UTu}_{op}$, SEQ ID NO:6; tRNA$^{UTu}_{am}$, SEQ ID NO:7), and E. coli tRNA$^{Ser}$ (right. SEQ ID NO:4). E. coli tRNA$^{Ser}$ (right) serves as a major scaffold for tRNA$^{UTu}$ (center) with the exception of the acceptor stem that originates from E. coli tRNA$^{Sec}$ (boxed sequence elements). Major EF-Tu recognition elements were retained from tRNA$^{Ser}$ as well (circled sequence elements). Substitution of the amber anticodon CUA (tRNA$^{UTu}_{am}$) for the opal anti-codon UCA (tRNA$^{UTu}_{op}$) are depicted with arrows and labeling.

UUCCGCCA, which is depicted in FIG. 3

(left panel).

In some embodiments, the non-naturally occurring tRNA$^{Sec}$ is a variant of an M. maripaludis tRNA$^{Sec}$, for example, (SEQ ID NO: 2)
GGCACGGGGUGCUUAUCUUGGUAGAUGAGGGCGGACUUCAGAU

CCGUCGAGUUCCGUUGGAAUUCGGGGUUCGAUUCCCCCCUGCG

CCGCCA.

In some embodiments, the non-naturally occurring tRNA$^{Sec}$ is a variant of a human tRNA$^{Sec}$, for example, (SEQ ID NO: 3)
GCCCGGAUGAUCCUCAGUGGUCUGGGGUGCAGGCUUCAAACCU

GUAGCUGUCUAGGGACAGAGUGGUUCAAUUCCACCUUUCGGGC

GCCA, which is depicted in FIG. 2.

A non-naturally occurring tRNA$^{Sec}$ that is a variant of a naturally occurring tRNA$^{Sec}$ can have a nucleic acid sequence at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO:1, 2, or 3. Preferably the non-naturally occurring tRNA$^{Sec}$ that is a variant of a naturally occurring tRNA$^{Sec}$ is characterized by one or more of the following elements: (1) the non-naturally occurring tRNA$^{Sec}$ can be recognized by SerRS and by EF-Tu, or variants thereof (2) when aminoacylated with serine the non-naturally occurring Ser-tRNA$^{Sec}$ can be converted to non-naturally occurring Sec-tRNA$^{Sec}$ by SelA or variant thereof (3) when aminoacylated with serine the non-naturally occurring Ser-tRNA$^{Sec}$ can be phosphorylated by PSTK or variant thereof (4) when aminoacylated with phosphorylated serine the non-naturally occurring Sep-tRNA$^{Sec}$ can serve as a substrate for SepSecS or variant thereof.

b. Variants of Naturally Occurring tRNA$^{Ser}$

The non-naturally occurring tRNASec disclosed herein can be a variant of a naturally occurring tRNA$^{Ser}$. The naturally occurring tRNA$^{Ser}$ can be from a prokaryote, including but not limited to E. coli, an archaea, including, but not limited to, M. maripaludis and M. jannaschii, or a eukaryote including, but not limited to human.

In some embodiments, the non-naturally occurring tRNA$^{Sec}$ is a variant of an E. coli tRNA$^{Ser}$, for example, (SEQ ID NO: 4)
GGAAGUGUGGCCGAGCGGUUGAAGGCACCGGUCUUGAAAACCG

GCGACCCGAAAGGGUUCCAGAGUUCGAAUCUCUGCGCUUCCGCC

A, depicted in FIG. 3 (right panel).

In some embodiments, the non-naturally occurring tRNA$^{Sec}$ is a variant of an M. maripaludis tRNA$^{Ser}$, for example, (SEQ ID NO: 5)
GCAGAGGUGGUUGAGCUUGGCCAAAGGCGCCGGACUUGAAAUC

CGGUUCUCCACUGGGGAGCGGGGGUUCAAAUCCCUCCCUCUGCG

CCA.

A non-naturally occurring tRNA$^{Sec}$ that is a variant of a naturally occurring tRNA$^{Sec}$ can have a nucleic acid sequence at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more identical to SEQ ID NO:4 or 5. Preferably the non-naturally occurring tRNA$^{Sec}$ that is a variant of an E. coli tRNA$^{Ser}$ is characterized by one or more of the following elements: (1) the non-naturally occurring tRNA$^{Sec}$ can be recognized by SerRS and by EF-Tu, or variants thereof; (2) when aminoacylated with serine the non-naturally occurring Ser-tRNA$^{Sec}$ can be converted to non-naturally occurring Sec-tRNA$^{Sec}$ by SelA; (3) when aminoacylated with serine the non-naturally occurring Ser-tRNA$^{Sec}$ can be phosphorylated by PSTK or variant thereof; (4) when aminoacylated with phosphorylated serine the non-naturally occurring Sep-tRNA$^{Sec}$ can serve as a substrate for SepSecS or variant thereof.

c. Chimeric tRNA$^{Sec}$

The non-naturally occurring tRNA$^{Sec}$ disclosed herein can also be a chimeric tRNA including sequences from two or more naturally occurring tRNAs. Some embodiments, the non-naturally occurring tRNA includes sequences from a naturally occurring tRNA$^{Sec}$ and a naturally occurring tRNA$^{Ser}$. The chimeric tRNA can include nucleic acid sequences or features, for example an antideterminant element, from a prokaryote, including but not limited to E. coli, an archaea, including, but not limited to, M. maripaludis and M. jannaschii, or a eukaryote including, but not limited to, human.

i. E. coli Chimeras

Examples of non-naturally occurring tRNA$^{Sec}$ that are chimeric tRNAs including sequence elements from E. coli include, but are not limited to

GGAAGAUGUGGCCGAGCGGUUGAAGGCACCGGUCUUCAAAACC

GGCGACCCGAAAGGGUUCCAGAGUUCGAAUCUCUGCAUCUUCC

GCCA (SEQ ID NO: 6; *E. coli* tRNA$^{UTu}$-opal), as depicted in FIG. 3 (center panel);

GGAAGAUGUGGCCGAGCGGUUGAAGGCACCGGUCUCUAAAACC

GGCGACCCGAAAGGGUUCCAGAGUUCGAAUCUCUGCAUCUUCC

GCCA (SEQ ID NO: 7; *E. coli* tRNA$^{UTu}$-amber), as depicted in FIG. 3 (center panel);
and

GGAAGAUGUGGCCGAGCGGUUGAAGGCACCGGUCUUUAAAACC

GGCGACCCGAAAGGGUUCCAGAGUUCGAAUCUCUGCAUCUUCC

GCCA (SEQ ID NO: 8; *E. coli* tRNA$^{UTu}$-ochre).

Other examples of non-naturally occurring tRNA$^{Sec}$ that are chimeric tRNAs including sequence elements from *E. coli* include, but are not limited to

GGCACUGUGGCCGAGCGGUUGAAGGCACCGGUCUUCAAAACCG

GCGACCCGAAAGGGUUCCAGAGUUCGAAUCUCUGCGGUGCCGCC

Figures 4A, 4B:
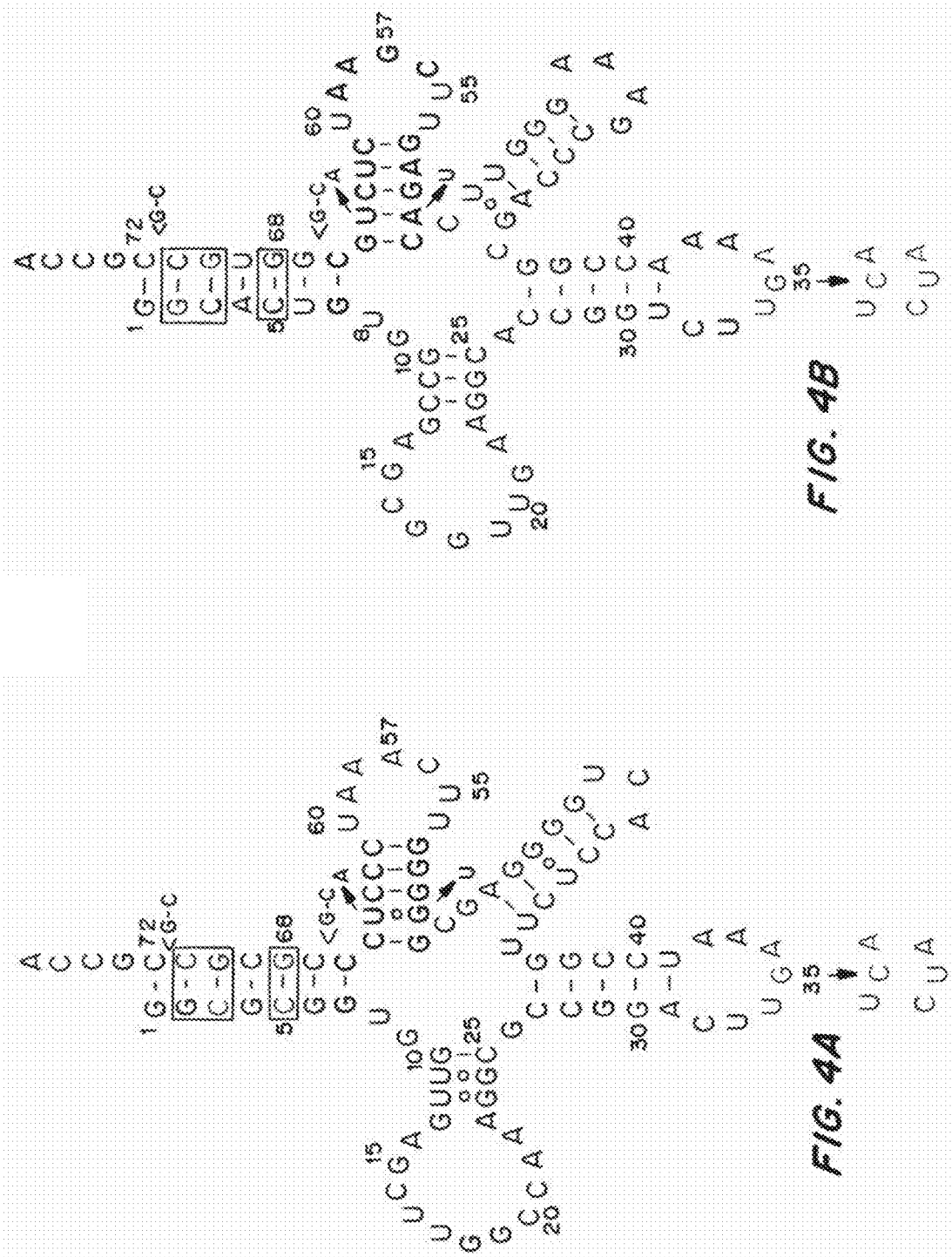
FIGS. 4A and 4B are depictions of the primary and secondary structures of a non-naturally occurring tRNA$^{UTu}$ with a body derived from M. maripaludis (FIG. 4A, tRNA$^{UTu}_{UCA}$; SEQ ID NO:57; tRNA$^{UTu}_{op}$, SEQ ID NO:33; tRNA$^{UTu}_{am}$, SEQ ID NO:34) and a non-naturally occurring tRNA$^{UTu}$ with a body derived from E. coli (FIG. 4B, tRNA$^{UTu}_{UCA}$; SEQ ID NO:58; tRNA$^{UTu}_{op}$, SEQ ID NO:9.

A (SEQ ID NO: 9; *E. coli* tRNA$^{UTu}$-opal), as depicted in FIG. 4B;

GGCACUGUGGCCGAGCGGUUGAAGGCACCGGUCUCUAAAACCG

GCGACCCGAAAGGGUUCCAGAGUUCGAAUCUCUGCGGUGCCGCC

A (SEQ ID NO: 10; *E. coli* tRNA$^{UTu}$-amber), as depicted in FIG. 4B;
and

GGCACUGUGGCCGAGCGGUUGAAGGCACCGGUCUUUAAAACCG

GCGACCCGAAAGGGUUCCAGAGUUCGAAUCUCUGCGGUGCCGCC

A (SEQ ID NO: 11; *E. coli* tRNA$^{UTu}$-ochre), which are non-naturally occurring chimeras of *E. coli* tRNA$^{Ser}$ with PSTK identity elements.

In some embodiments, the non-naturally occurring tRNA$^{Sec}$ is a variant of SEQ ID NO:9 such as

GGGCACUGUGGCCGAGCGGUUGAAGGCACCGGUCUUCAAAACC

GGCGACCCGAAAGGGUUCCAGAGUUCGAAUCUCUGCGGUGCCC

GCCA (SEQ ID NO: 12; *E. coli* tRNA$^{UTu}$-opalvariant 1);

GGCACUGGUGGCCGAGCGGUUGAAGGCACCGGUCUUCAAAACC

GGCGACCCGAAAGGGUUCCAGAGUUCGAAUCUCUGCCGGUGCC

GCCA (SEQ ID NO: 13; *E. coli* tRNA$^{UTu}$-opalvariant 2);

GGCACUGUGGCCGAGCGGUUGAAGGCACCGGUCUUCAAAACCG

GCGACCCGAAAGGGUUCCUGAGUUCGAAUCUCAGCGGUGCCGCC

A (SEQ ID NO: 14; *E. coli* tRNA$^{UTu}$-opalvariant 3);

GGGCACUGGUGGCCGAGCGGUUGAAGGCACCGGUCUUCAAAAC

CGGCGACCCGAAAGGGUUCCAGAGUUCGAAUCUCUGCCGGUGCC

CGCCA (SEQ ID NO: 15; *E. coli* tRNA$^{UTu}$-opalvariant 4);

GGGCACUGUGGCCGAGCGGUUGAAGGCACCGGUCUUCAAAACC

GGCGACCCGAAAGGGUUCCUGAGUUCGAAUCUCAGCGGUGCCC

GCCA (SEQ ID NO: 16; *E. coli* tRNA$^{UTu}$-opalvariant 5);

GGCACUGGUGGCCGAGCGGUUGAAGGCACCGGUCUUCAAAACC

GGCGACC CGAAAGGGUUCCUGAGUUCGAAUCUCAGCCGGUGCC

GCCA (SEQ ID NO: 17; *E. coli* tRNA$^{UTu}$-opalvariant 6);
or

GGGCACUGGUGGCCGAGCGGUUGAAGGCACCGGUCUUCAAAAC

CGGCGACCCGAAAGGGUUCCUGAGUUCGAAUCUCAGCCGGUGC

CGCCA (SEQ ID NO: 18; *E. coli* tRNA$^{UTu}$-opalvariant 7)

In some embodiments, the non-naturally occurring tRNA$^{Sec}$ is a variant of SEQ ID NO:10 such as

GGGCACUGUGGCCGAGCGGUUGAAGGCACCGGUCUCUAAAACC

GGCGACCCGAAAGGGUUCCAGAGUUCGAAUCUCUGCGGUGCCC

GCCA (SEQ ID NO: 19; *E. coli* tRNA$^{UTu}$-ambervariant 1);

GGCACUGGUGGCCGAGCGGUUGAAGGCACCGGUCUCUAAAACC

GGCGACCCGAAAGGGUUCCAGAGUUCGAAUCUCUGCCGGUGCC

GCCA (SEQ ID NO: 20; *E. coli* tRNA$^{UTu}$-ambervariant 2);

GGCACUGUGGCCGAGCGGUUGAAGGCACCGGUCUCUAAAACCG

GCGACCCGAAAGGGUUCCUGAGUUCGAAUCUCAGCGGUGCCGCC

A (SEQ ID NO: 21; *E. coli* tRNA$^{UTu}$-ambervariant 3);

GGGCACUGGUGGCCGAGCGGUUGAAGGCACCGGUCUCUAAAAC

CGGCGACCCGAAAGGGUUCCAGAGUUCGAAUCUCUGCCGGUGCC

CGCCA (SEQ ID NO: 22; *E. coli* tRNA$^{UTu}$-ambervariant 4);

-continued
GGGCACUGUGGCCGAGCGGUUGAAGGCACCGGUCUCUAAAACC

GGCGACCCGAAAGGGUUCCUGAGUUCGAAUCUCAGCGGUGCCC

GCCA (SEQ ID NO: 23; E. coli tRNA$^{UTu}$-ambervariant 5);

GGCACUGGUGGCCGAGCGGUUGAAGGCACCGGUCUCUAAAACC

GGCGACCCGAAAGGGUUCCUGAGUUCGAAUCUCAGCCGGUGCC

GCCA (SEQ ID NO: 24; E. coli tRNA$^{UTu}$-ambervariant 6);

GGGCACUGGUGGCCGAGCGGUUGAAGGCACCGGUCUCUAAAAC

CGGCGACCCGAAAGGGUUCCUGAGUUCGAAUCUCAGCCGGUGCC

CGCCA (SEQ ID NO: 25; E. coli tRNA$^{UTu}$-ambervariant 7);

In some embodiments, the non-naturally occurring tRNA$^{Sec}$ is a variant of SEQ ID NO:11 such as

GGGCACUGUGGCCGAGCGGUUGAAGGCACCGGUCUUUAAAACC

GGCGACCCGAAAGGGUUCCAGAGUUCGAAUCUCUGCGGUGCCC

GCCA (SEQ ID NO: 26; E. coli tRNA$^{UTu}$-ochrevariant 1);

GGCACUGGUGGCCGAGCGGUUGAAGGCACCGGUCUUUAAAACC

GGCGACCCGAAAGGGUUCCAGAGUUCGAAUCUCUGCCGGUGCC

GCCA (SEQ ID NO: 27; E. coli tRNA$^{UTu}$-ochrevariant 2);

GGCACUGUGGCCGAGCGGUUGAAGGCACCGGUCUUUAAAACCG

GCGACCCGAAAGGGUUCCUGAGUUCGAAUCUCAGCGGUGCCGCC

A (SEQ ID NO: 28; E. coli tRNA$^{UTu}$-ochrevariant 3);

GGGCACUGGUGGCCGAGCGGUUGAAGGCACCGGUCUUUAAAAC

CGGCGACCCGAAAGGGUUCCAGAGUUCGAAUCUCUGCGGUGCC

CGCCA (SEQ ID NO: 29; E. coli tRNA$^{UTu}$-ochrevariant 4);

GGGCACUGUGGCCGAGCGGUUGAAGGCACCGGUCUUUAAAACC

GGCGACCCGAAAGGGUUCCUGAGUUCGAAUCUCAGCGGUGCCC

GCCA (SEQ ID NO: 30; E. coli tRNA$^{UTu}$-ochrevariant 5);

-continued
GGCACUGGUGGCCGAGCGGUUGAAGGCACCGGUCUUUAAAACC

GGCGACCCGAAAGGGUUCCUGAGUUCGAAUCUCAGCCGGUGCC

GCCA (SEQ ID NO: 31; E. coli tRNA$^{UTu}$-ochrevariant 6);
or

GGGCACUGGUGGCCGAGCGGUUGAAGGCACCGGUCUUUAAAAC

CGGCGACCCGAAAGGGUUCCUGAGUUCGAAUCUCAGCCGGUGCC

CGCCA (SEQ ID NO: 32; E. coli tRNA$^{UTu}$-ochrevariant 7)

In some embodiments, the non-naturally occurring tRNA$^{Sec}$ is a variant of tRNA$^{UTu}$, for example, SEQ ID NO:7:

G$^1$GAAG$^5$A$^{5a}$UGUGG$^{10}$CCGAGCGGU$^{20}$UGAAGGCACCGG$^{30}$UCU$C$UAAAA

C$^{40}$CGGCGACCCGAAAGGGUUCCA$^{50}$GAGUUCGAAU$^{60}$CUCUGCAU$^{67a}$

CUU$^{70}$CCGCCA (SEQ ID NO: 7; E. coli tRNA$^{UTu}$-amber), or the opal or ochre equivalent thereof (e.g., SEQ ID NO:6 or 8). In some embodiments, the non-naturally occurring tRNA$^{Sec}$ has at least 80, 81, 82, 83, 84, 85, 86, 97, 88, 89, 90, 91, 92, 93, 94, 95, 96, 97, 97, 98, or 99% sequence identity to SEQ ID NO: 6, 7, or 8.

Modifications can include single and combined exchanges (i.e., substitutions), one or more insertions, one or more deletions, and combinations thereof, of nucleotides in various regions of the tRNA. Preferably the modifications alter the variant relative to tRNA$^{UTu}$ to (i) more closely resemble the features of tRNA$^{Sec}$ that contribute to binding of SelA than tRNA$^{UTu}$. The mechanism by which SelA discriminates between tRNA$^{Ser}$ and tRNA$^{Sec}$ is described in [Itoh, et al., *Science*, 340:75-78 (2013)]. Preferably the important tRNA$^{UTu}$ features that (ii) provide thermodynamic binding specificity for EF-Tu [Schrader, et al., *J. Mol. Biol.*, 386:1255-1264 (2009)], (iii) contribute to the incompatibility between tRNA$^{Sec}$ and EF-Tu [Rudinger, et al., *EMBO J.*, 15:650-657 (1996)], or the combination thereof are left intact. In preferred embodiments, the variant exhibits (i), (ii), (iii), or a combination thereof, most preferably (i), (ii), and (iii).

In some embodiments the variant includes one or more insertions deletions or substitutions at the underlined positions illustrated in SEQ ID NO:7 below, (SEQ ID NO: 7)
GGAAGAUGUGGCCGAGCGGUUGAAGGGCACCGGUCUCUAAAACC

GGCGACCCGAAAGGGUUCCAGAGUUCGAAUCUCUGCAUCUUCC

GCCA, or the equivalent position(s) in SEQ ID NO:6 or 8.

In preferred embodiments, the tRNA exhibits reduced misincorporation Ser in vivo, in vitro, or a combination thereof relative to SEQ ID NO:6, 7, or 8. Preferably, the tRNA exhibits better interaction with SelA (e.g., tighter binding), while retaining robust Ser-tRNA formation by SerRS.

An insertion(s) can occur between, immediately before, immediately after, or a combination thereof relative to the underlined positions in SEQ ID NO:7 above, or the equivalent position(s) in SEQ ID NO:6 or 8. A deletion can occur at, immediately before, immediately after, or a combination thereof relative to the underlined positions. A substitution can occur at any one or more of the underlined positions. For example, in some embodiments, (i) nucleotide positions 9 and/or 10 remain unchanged or are substituted; (ii) nucleotides 15 and/or 16 remain unchanged or are substituted; (iii) nucleotide 20 remains unchanged or is deleted; (iv) one or both of nucleotides 25 and 26 remain unchanged, one or both of nucleotides 25 and 26 are substituted, a nucleotide is inserted between nucleotides 25 and 26, or a combination thereof; (v) nucleotide 28 remains unchanged or is substituted; (vi) one or two nucleotides are inserted between nucleotides 45 and 46; (vii) one or two nucleotides are inserted between nucleotides 61 and 62; (viii) nucleotide 65 remains the same or is substituted; (ix) nucleotide 72 remains the same or is substituted; (x) nucleotide 75 remains the same or is substituted.

Nucleotide positions within a tRNA sequence can also be identified based the nucleotide numbering established in Sprinzl, et al., *Nucleic Acids Research*, 26(1):148-153 (1998). As illustrated in text, figures, and sequences provide herein, this numbering system coordinates the relative locations of nucleotides and base pairs between two or more tRNA that may differ in the total number of nucleotides due to insertions and/or deletions. Thus nucleotides in any of the disclosed tRNA can be characterized based the nucleotide numbering from the terminal 5' nucleotide, or the nucleotide (s) at the base position(s) identified according to the Sprinzl numbering system. For example, mutations relative to tRNA$^{UTu}$ (SEQ ID NO:6, 7, or 8) can be at, for example, positions U8, G9, and A27 in the core region; A14 and G15 in the D-arm; U21 in the D-loop; A52 and U62 in the T-arm; A59 in the T-loop; and U44 and G48 in the variable arm.

Thus, in some embodiments, the variants includes the backbone of SEQ ID NO:6, 7, or 8, with one or more substitutions, deletions, or insertions at one or more of A14 and G15 in the D-arm; deletion of U21 in the D-loop; A52 and U62 in the T-arm; A59 in the T-loop; and residues 44 and 48 in the variable arm relative to tRNA$^{UTu}$ (SEQ ID NO:6, 7, or 8).

In some embodiments, the variant has substitutions at U8, G9, and A27 in the core region; substitutions at A14 and G15 in the D-arm; deletion of U21 in the D-loop; substitutions at A52 and U62 in the T-arm; a substitution at A59 in the T-loop; and the insertion of residues 44 and 48 in the variable arm relative to tRNA$^{UTu}$ (SEQ ID NO:6, 7, or 8).

More specifically, mutations relative to tRNA$^{UTu}$ (SEQ ID NO:6, 7, or 8) can be, for example, U8G, G9U, and A27G in the core region; A14U and G15C in the D-arm; deletion of U21 in the D-loop; A52G and U62C in the T-arm; A59C in the T-loop; and the insertion of residues U44 and G48 in the variable arm.

tRNA elements important for selenocysteine insertion, are illustrated with reference tRNA$^{UTu}$ in FIG. 3. In this figure, the acceptor stem of the tRNA is highlighted as originating from tRNA$^{Sec}$, and is important for recognition by the enzyme SelA. The circled region in FIG. 3 originates from tRNA$^{Ser}$, and is important both for recognition by the enzyme EF-Tu and for its lack of recognition by the enzyme SelB. Thus in some embodiments, the tRNA (e.g., the aminoacylated tRNA) is recognized by selA and EF-Tu, and optionally is not recognized by selB.

In tRNA$^{SecUX}_{am}$, described in Thyer, et al., *J. Am. Chem. Soc.*, 137:46-49 (2015) (SEQ ID NO:93), the circled region of FIG. 3 was mutated in tRNA$^{Sec}$ (e.g., SEQ ID NO:1) to enable recognition by EF-Tu. The EF-Tu recognition region is very similar between tRNA$^{UTu}$ and tRNA$^{SecUX}$; residues G7, U64, G65, and C66 are shared between the two. Residues 50 and 49 are different between tRNA$^{SecUX}$ and tRNA$^{UTu}$, however in both cases they form base pairs with residues U64 and G65, respectively.

Exemplary variants are provided below. The position(s) of modifications relative to SEQ ID NO:7 (amber), 6 (opal) or 8 (ochre), respectively, are bolded and underlined. The anti-codon is in italics. tRNA positional markers (e.g., 1, 5, 5a, 10, 20, 30, 40, 50, 60, 67a, 70 according to the numbering of Sprinzl, et al., *Nucleic Acids Research*, 26(1):148-153 (1998)) are provided in superscript and are not part of the tRNA sequence.

Amber Variants

UTuX
G$^1$GAAG$^5$A$^{5a}$UGGUG$^{10}$CCGUCCGGU$^{20}$GAAGGCGCCGG$^{30}$UCU*CUA*A

AAC$^{40}$CGGUCGACCCGAAAGGGUUCGCA$^{50}$GGGUUCGACU$^{60}$CCCU

GCAU$^{67a}$CUCCCGCCA (SEQ ID NO: 59; E. coli scaffold, tRNA$^{UTuX}$-amber)

Variant A
G$^1$GAAG$^5$A$^{5a}$UGGUG$^{10}$CCGAGCGGU$^{20}$UGAAGGCGCCGG$^{30}$UCU*CUA*

AAAC$^{40}$CGGCGACCCGAAAGGGUUCCA$^{50}$GAGUUCGAAU$^{60}$CUCUGC

AU$^{67a}$CUU$^{70}$CCGCCA (SEQ ID NO: 60; E. coli scaffold, tRNA$^{variant\ A}$-amber)

Variant E
G$^1$GAAG$^5$A$^{5a}$UGUG$^{10}$GCCGAGCGGU$^{20}$UGAAGGCGCCGG$^{30}$UCU*CUA*A

AAC$^{40}$CGGCGACCCGAAAGGGUUCCA$^{50}$GGGUUCGACU$^{60}$CCCUGCA

U$^{67a}$CUCCCGCCA (SEQ ID NO: 61; E. coli scaffold, tRNA$^{variant\ E}$-amber)

Variant H
G$^1$GAAG$^5$A$^{5a}$UGGUG$^{10}$CCGUCCGGU$^{20}$GAAGGCGCCGG$^{30}$UCU*CUA*A

AAC$^{40}$CGGCGACCCGAAAGGGUUCCA$^{50}$GGGUUCGACU$^{60}$CCCUGCA

U$^{67a}$CUU$^{70}$CCGCCA (SEQ ID NO: 62; E. coli scaffold, tRNA$^{variant\ H}$-amber)

Variant I
G$^1$GAAG$^5$A$^{5a}$UGGUG$^{10}$CCGUCCGGU$^{20}$GAAGGCGCCGG$^{30}$UCU*CUA*A

AAC$^{40}$CGGUUCGACCCGAAAGGGUUCGGCA$^{50}$GGGUUCGACU$^{60}$CC

CUGCAU$^{67a}$CUU$^{70}$CCGCCA (SEQ ID NO: 63; E. coli scaffold, tRNA$^{variant\ I}$-amber)

Variant J
G$^1$GAAG$^5$A$^{5a}$UGUG$^{10}$GCCGAGCGGU$^{20}$UGAAGGCGCCGG$^{30}$UCU*CUA*A

AAC$^{40}$CGGCGACCCGAAAGGGUUCCA$^{50}$GGGUUCGAUU$^{60}$CCCUGCA

U$^{67a}$CUU$^{70}$CCGCCA (SEQ ID NO: 64; E. coli scaffold, tRNA$^{variant\ J}$-amber)

Variant L
G$^1$GAAG$^5$A$^{5a}$UGGUG$^{10}$CCGUCCGGU$^{20}$UGAAGGCGCCGG$^{30}$UCU*CUA*

AAAC$^{40}$CGGCGACCCGAAAGGGUUCCA$^{50}$GAGUUCGAAU$^{60}$CUCUGC

AU$^{67a}$CUU$^{70}$CCGCCA (SEQ ID NO: 65; E. coli scaffold, tRNA$^{variant\ L}$-amber)

Variant M
$G^1GAAG^{5a}A^{5a}UG\underline{GU}G^{10}CCG\underline{UC}CGGU^{20}GAAGGC\underline{G}CCGG^{30}UCU\mathit{C}UAA$
$AAC^{40}CGGCGACCCGAAAGGGUUCCA^{50}G\underline{G}GUUCGA\underline{UU}^{60}C\underline{C}CUGCA$
$U^{67a}CUU^{70}CCGCCA$ (SEQ ID NO: 66; E. coli scaffold, tRNA$^{variant\ M}$-amber)

Variant N
$G^1GAAG^{5a}A^{5a}UG\underline{GU}G^{10}CCG\underline{UC}CGGU^{20}GAAGGC\underline{G}CCGG^{30}UCU\mathit{C}UAA$
$AAC^{40}CGG\underline{U}CGACCCGAAAGGGUUC\underline{G}CA^{50}G\underline{G}GUUCGA\underline{UU}^{60}C\underline{C}CU$
$GCAU^{67a}CUU^{70}CCGCCA$ (SEQ ID NO: 67; E. coli scaffold, tRNA$^{variant\ N}$-amber)

Opal Variants

UTuX
$G^1GAAG^{5a}A^{5a}UG\underline{GU}G^{10}CCG\underline{UC}CGGU^{20}GAAGGC\underline{G}CCGG^{30}UCU\mathit{U}CAA$
$AAC^{40}CGG\underline{U}CGACCCGAAAGGGUUC\underline{G}CA^{50}G\underline{G}GUUCGA\underline{CU}^{60}C\underline{C}CU$
$GCAU^{67a}CUU^{70}CCGCCA$ (SEQ ID NO: 68; E. coli scaffold, tRNA$^{UTuX}$-opal)

Variant A
$G^1GAAG^{5a}A^{5a}UG\underline{GU}G^{10}CCGAGCGGU^{20}UGAAGGC\underline{G}CCGG^{30}UCU\mathit{U}CA$
$AAAC^{40}CGGCGACCCGAAAGGGUUCCA^{50}GAGUUCGAAU^{60}CUCUGC$
$AU^{67a}CUU^{70}CCGCCA$ (SEQ ID NO: 69; E. coli scaffold, tRNA$^{variant\ A}$-opal)

Variant E
$G^1GAAG^{5a}A^{5a}UGUG^{10}GCCGAGCGGU^{20}UGAAGGC\underline{G}CCGG^{30}UCU\mathit{U}CAA$
$AAC^{40}CGGCGACCCGAAAGGGUUCCA^{50}G\underline{G}GUUCGA\underline{CU}^{60}C\underline{C}CUGCA$
$U^{67a}CUU^{70}CCGCCA$ (SEQ ID NO: 70; E. coli scaffold, tRNA$^{variant\ E}$-opal)

Variant H
$G^1GAAG^{5a}A^{5a}UG\underline{GU}G^{10}CCG\underline{UC}CGGU^{20}GAAGGC\underline{G}CCGG^{30}UCU\mathit{U}CAA$
$AAC^{40}CGGCGACCCGAAAGGGUUCCA^{50}G\underline{G}GUUCGA\underline{CU}^{60}C\underline{C}CUGCA$
$U^{67a}CUU^{70}CCGCCA$ (SEQ ID NO: 71; E. coli scaffold, tRNA$^{variant\ H}$-opal)

Variant I
$G^1GAAG^{5a}A^{5a}UG\underline{GU}G^{10}CCG\underline{UC}CGGU^{20}GAAGGC\underline{G}CCGG^{30}UCU\mathit{U}CAA$
$AAC^{40}CGG\underline{UU}CGACCCGAAAGGGUUC\underline{GG}CA^{50}G\underline{G}GUUCGA\underline{CU}^{60}CC$
$CUGCAU^{67a}CUU^{70}CCGCCA$ (SEQ ID NO: 72; E. coli scaffold, tRNA$^{variant\ I}$-opal)

Variant J
$G^1GAAG^{5a}A^{5a}UGUG^{10}GCCGAGCGGU^{20}UGAAGGC\underline{G}CCGG^{30}UCU\mathit{U}CAA$
$AAC^{40}CGGCGACCCGAAAGGGUUCCA^{50}G\underline{G}GUUCGA\underline{UU}^{60}C\underline{C}CUGCA$
$U^{67a}CUU^{70}CCGCCA$ (SEQ ID NO: 73; E. coli scaffold, tRNA$^{variant\ J}$-opal)

Variant L
$G^1GAAG^{5a}A^{5a}UG\underline{GU}G^{10}CCG\underline{UC}CGGU^{20}UGAAGGC\underline{G}CCGG^{30}UCU\mathit{U}CA$
$AAAC^{40}CGGCGACCCGAAAGGGUUCCA^{50}GAGUUCGAAU^{60}CUCUGC$
$AU^{67a}CUU^{70}CCGCCA$ (SEQ ID NO: 74; E. coli scaffold, tRNA$^{variant\ L}$-opal)

Variant M
$G^1GAAG^{5a}A^{5a}UG\underline{GU}G^{10}CCG\underline{UC}CGGU^{20}GAAGGC\underline{G}CCGG^{30}UCU\mathit{U}CAA$
$AAC^{40}CGGCGACCCGAAAGGGUUCCA^{50}G\underline{G}GUUCGA\underline{UU}^{60}C\underline{C}CUGCA$
$U^{67a}CUU^{70}CCGCCA$ (SEQ ID NO: 75; E. coli scaffold, tRNA$^{variant\ M}$-opal)

Variant N
$G^1GAAG^{5a}A^{5a}UG\underline{GU}G^{10}CCG\underline{UC}CGGU^{20}GAAGGC\underline{G}CCGG^{30}UCU\mathit{U}CAA$
$AAC^{40}CGG\underline{U}CGACCCGAAAGGGUUC\underline{G}CA^{50}G\underline{G}GUUCGA\underline{UU}^{60}C\underline{C}CU$
$GCAU^{67a}CUCCCGCCA$ (SEQ ID NO: 76; E. coli scaffold, tRNA$^{variant\ N}$-opal)

Ochre Variants

UTuX
$G^1GAAG^{5a}A^{5a}UG\underline{GU}G^{10}CCG\underline{UC}CGGU^{20}GAAGGC\underline{G}CCGG^{30}UCU\mathit{UU}AA$
$AAC^{40}CGG\underline{U}CGACCCGAAAGGGUUC\underline{G}CA^{50}G\underline{G}GUUCGA\underline{CU}^{60}C\underline{C}CU$
$GCAU^{67a}CUU^{70}CCGCCA$ (SEQ ID NO: 77; E. coli scaffold, tRNA$^{UTuX}$-ochre)

Variant A
$G^1GAAG^{5a}A^{5a}UG\underline{GU}G^{10}CCGAGCGGU^{20}UGAAGGC\underline{G}CCGG^{30}UCU\mathit{UU}A$
$AAAC^{40}CGGCGACCCGAAAGGGUUCCA^{50}GAGUUCGAAU^{60}CUCUGC$
$AU^{67a}CUU^{70}CCGCCA$ (SEQ ID NO: 78; E. coli scaffold, tRNA$^{variant\ A}$-ochre)

Variant E
$G^1GAAG^{5a}A^{5a}UGUG^{10}GCCGAGCGGU^{20}UGAAGGC\underline{G}CCGG^{30}UCU\mathit{UU}A$
$AAAC^{40}CGGCGACCCGAAAGGGUUCCA^{50}G\underline{G}GUUCGA\underline{CU}^{60}C\underline{C}CUGC$
$AU^{67a}CUU^{70}CCGCCA$ (SEQ ID NO: 79; E. coli scaffold, tRNA$^{variant\ E}$-ochre)

Variant H
$G^1GAAG^{5a}A^{5a}UG\underline{GU}G^{10}CCG\underline{UC}CGGU^{20}GAAGGC\underline{G}CCGG^{30}UCU\mathit{UU}AA$
$AAC^{40}CGGCGACCCGAAAGGGUUCCA^{50}G\underline{G}GUUCGA\underline{CU}^{60}C\underline{C}CUGCA$
$U^{67a}CUU^{70}CCGCCA$ (SEQ ID NO: 80; E. coli scaffold, tRNA$^{variant\ H}$-ochre)

Variant I
$G^1GAAG^{5a}A^{5a}UG\underline{GU}G^{10}CCG\underline{UC}CGGU^{20}GAAGGC\underline{G}CCGG^{30}UCU\mathit{UU}AA$
$AAC^{40}CGG\underline{UU}CGACCCGAAAGGGUUC\underline{GG}CA^{50}G\underline{G}GUUCGA\underline{CU}^{60}CC$
$CUGCAU^{67a}CUU^{70}CCGCCA$ (SEQ ID NO: 81; E. coli scaffold, tRNA$^{variant\ I}$-ochre)

Variant J
$G^1GAAG^{5a}A^{5a}UGUG^{10}GCCGAGCGGU^{20}UGAAGGC\underline{G}CCGG^{30}UCU\mathit{UU}A$
$AAAC^{40}CGGCGACCCGAAAGGGUUCCA^{50}G\underline{G}GUUCGA\underline{UU}^{60}C\underline{C}CUGC$
$AU^{67a}CUU^{70}CCGCCA$ (SEQ ID NO: 82; E. coli scaffold, tRNA$^{variant\ J}$-ochre)

Variant L
G¹GAAG⁵A⁵ᵃUGGUG¹⁰CCGUCCGGU²⁰UGAAGGCGCCGG³⁰UCUUUA

AAAC⁴⁰CGGCGACCCGAAAGGGUUCCA⁵⁰GAGUUCGAAU⁶⁰CUCUGC

AU⁶⁷ᵃCUU⁷⁰CCGCCA (SEQ ID NO: 83; E. coli scaffold, tRNA^(variant L)-ochre)

Variant M
G¹GAAG⁵A⁵ᵃUGGUG¹⁰CCGUCCGGU²⁰GAAGGCGCCGG³⁰UCUUUAA

AAC⁴⁰CGGCGACCCGAAAGGGUUCCA⁵⁰GGGUUCGAUU⁶⁰CCCUGCA

U⁶⁷ᵃCUU⁷⁰CCGCCA (SEQ ID NO: 84; E. coli scaffold, tRNA^(variant M)-ochre)

Variant N
G¹GAAG⁵A⁵ᵃUGGUG¹⁰CCGUCCGGU²⁰GAAGGCGCCGG³⁰UCUUUAA

AAC⁴⁰CGGUCGACCCGAAAGGGUUCGCA⁵⁰GGGUUCGAUU⁶⁰CCCU

GCAU⁶⁷ᵃCUCCCGCCA (SEQ ID NO: 85; E. coli scaffold, tRNA^(variant N)-ochre)

A non-naturally occurring tRNA^Sec that is a chimeric E. coli tRNA can have a nucleic acid sequence at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more identical to SEQ ID NO:6, 7, 8, 9, 10, 11, 12, 13, 14, 15, 16, 17, 18, 19, 20, 21, 22, 23, 24, 25, 26, 27, 28, 29, 30, 31, 32, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, or 92. Preferably the non-naturally occurring tRNA^Sec that is a chimeric E. coli tRNA^Sec is characterized by one or more of the following elements: (1) the non-naturally occurring tRNA^Sec can be recognized by SerRS and by EF-Tu, or variants thereof; (2) when aminoacylated with serine the non-naturally occurring Ser-tRNA^Sec can be converted to non-naturally occurring Sec-tRNA^Sec by SelA or variant thereof; (3) when aminoacylated with serine the non-naturally occurring Ser-tRNA^Sec can be phosphorylated by PSTK or variant thereof; (4) when aminoacylated with phosphorylated serine the non-naturally occurring Sep-tRNA^Sec can serve as a substrate for SepSecS or variant thereof.

ii. M. maripaludis Chimeras

Examples of non-naturally occurring tRNA^Sec that are chimeric tRNAs including sequences elements from M. maripaludis include, but are not limited to,

GGCGCGGUGGUUGAGCUUGGCCAAAGGCGCCGGACUUCAAAUC

CGGUUCUCCACUGGGGAGCGGGGGUUCAAAUCCCUCCCGCGCCG

CCA (SEQ ID NO: 33; M. maripaludis tRNA^UTu-opal), as depicted in FIG. 4A;

GGCGCGGUGGUUGAGCUUGGCCAAAGGCGCCGGACUCUAAAUC

CGGUUCUCCACUGGGGAGCGGGGGUUCAAAUCCCUCCCGCGCCG

CCA (SEQ ID NO: 34; M. maripaludis tRNA^UTu-amber), as depicted in FIG. 4A;

GGCGCGGUGGUUGAGCUUGGCCAAAGGCGCCGGACUUUAAAUC

CGGUUCUCCACUGGGGAGCGGGGGUUCAAAUCCCUCCCGCCG

CCA (SEQ ID NO: 35; M. maripaludis tRNA^UTu-ochre).

In some embodiments, the non-naturally occurring tRNA^Sec is a variant of SEQ ID NO:33 such as

GGGCGCGGUGGUUGAGCUUGGCCAAAGGCGCCGGACUUCAAAU

CCGGUUCUCCACUGGGGAGCGGGGGUUCAAAUCCCUCCCGCGCC

CGCCA (SEQ ID NO: 36; M. maripaludis tRNA^UTu-opal-variant 1);

GGCGCGGGUGGUUGAGCUUGGCCAAAGGCGCCGGACUUCAAAU

CCGGUUCUCCACUGGGGAGCGGGGGUUCAAAUCCCUCCCGCGC

CGCCA (SEQ ID NO: 37; M. maripaludis tRNA^UTu-opal-variant 2);

GGCGCGGUGGUUGAGCUUGGCCAAAGGCGCCGGACUUCAAAUC

CGGUUCUCCACUGGGGAGCGUGGGUUCAAAUCCCACCCGCGCCG

CCA (SEQ ID NO: 38; M. maripaludis tRNA^UTu-opal-variant 3);

GGGCGCGGGUGGUUGAGCUUGGCCAAAGGCGCCGGACUUCAAA

UCCGGUUCUCCACUGGGGAGCGGGGGUUCAAAUCCCUCCCCGCG

CCCGCCA (SEQ ID NO: 39; M. maripaludis tRNA^UTu-opal-variant 4);

GGGCGCGGUGGUUGAGCUUGGCCAAAGGCGCCGGACUUCAAAU

CCGGUUCUCCACUGGGGAGCGUGGGUUCAAAUCCCACCCGCGCC

CGCCA (SEQ ID NO: 40; M. maripaludis tRNA^UTu-opal-variant 5);

GGCGCGGGUGGUUGAGCUUGGCCAAAGGCGCCGGACUUCAAAU

CCGGUUCUCCACUGGGGAGCGUGGGUUCAAAUCCCACCCGCGC

CGCCA (SEQ ID NO: 41; M. maripaludis tRNA^UTu-opal-variant 6);
or

GGGCGCGGGUGGUUGAGCUUGGCCAAAGGCGCCGGACUUCAAA

UCCGGUUCUCCACUGGGGAGCGUGGGUUCAAAUCCCACCCCGCG

CCCGCCA (SEQ ID NO: 42; M. maripaludis tRNA^UTu-opal-variant 7).

In some embodiments, the non-naturally occurring tRNA^Sec is a variant of SEQ ID NO:34 such as

GGGCGCGGUGGUUGAGCUUGGCCAAAGGCGCCGGACUCUAAAU

CCGGUUCUCCACUGGGGAGCGGGGGUUCAAAUCCCUCCCGCGCC

CGCCA (SEQ ID NO: 43; M. maripaludis tRNA^UTu-amber-variant 1);

```
GGCGCGGGUGGUUGAGCUUGGCCAAAGGCGCCGGACUCUAAAU

CCGGUUCUCCACUGGGGAGCGGGGGUUCAAAUCCCUCCCCGCGC

CGCCA (SEQ ID NO: 44; M. maripaludis tRNA^UTu-ambervariant 2);

GGCGCGGUGGUUGAGCUUGGCCAAAGGCGCCGGACUCUAAAUC

CGGUUCUCCACUGGGGAGCGUGGGUUCAAAUCCCACCCGCCG

CCA (SEQ ID NO: 45; M. maripaludis tRNA^UTu-ambervariant 3);

GGGCGCGGGUGGUUGAGCUUGGCCAAAGGCGCCGGACUCUAAA

UCCGGUUCUCCACUGGGGAGCGGGGGUUCAAAUCCCUCCCCGCG

CCCGCCA (SEQ ID NO: 46; M. maripaludis tRNA^UTuamber-variant 4);

GGGCGCGGUGGUUGAGCUUGGCCAAAGGCGCCGGACUCUAAAU

CCGGUUCUCCACUGGGGAGCGUGGGUUCAAAUCCCACCCGCGCC

CGCCA (SEQ ID NO: 47; M. maripaludis tRNA^UTuamber-variant 5);

GGCGCGGGUGGUUGAGCUUGGCCAAAGGCGCCGGACUCUAAAU

CCGGUUCUCCACUGGGGAGCGUGGGUUCAAAUCCCACCCCGCGC

CGCCA (SEQ ID NO: 48; M. maripaludis tRNA^UTuamber-variant 6);
or

GGGCGCGGGUGGUUGAGCUUGGCCAAAGGCGCCGGACUCUAAA

UCCGGUUCUCCACUGGGGAGCGUGGGUUCAAAUCCCACCCCGCG

CCCGCCA (SEQ ID NO: 49; M. maripaludis tRNA^UTuamber-variant 7).
```

In some embodiments, the non-naturally occurring tRNA^Sec is a variant of SEQ ID NO:35 such as

```
GGGCGCGGUGGUUGAGCUUGGCCAAAGGCGCCGGACUUUAAAU

CCGGUUCUCCACUGGGGAGCGGGGGUUCAAAUCCCUCCCGCCG

CGCCA (SEQ ID NO: 50; M. maripaludis tRNA^UTu-ochrevariant 1);

GGCGCGGGUGGUUGAGCUUGGCCAAAGGCGCCGGACUUUAAAU

CCGGUUCUCCACUGGGGAGCGGGGGUUCAAAUCCCUCCCCGCGC

CGCCA (SEQ ID NO: 51; M. maripaludis tRNA^UTu-ochrevariant 2);

GGCGCGGUGGUUGAGCUUGGCCAAAGGCGCCGGACUUUAAAUC

CGGUUCUCCACUGGGGAGCGUGGGUUCAAAUCCCACCCGCGCCG

CCA (SEQ ID NO: 52; M. maripaludis tRNA^UTu-ochrevariant 3);

GGGCGCGGGUGGUUGAGCUUGGCCAAAGGCGCCGGACUUUAAA

UCCGGUUCUCCACUGGGGAGCGGGGGUUCAAAUCCCUCCCCGCG

CCCGCCA (SEQ ID NO: 53; M. maripaludis tRNA^UTuochre-variant 4);

GGGCGCGGUGGUUGAGCUUGGCCAAAGGCGCCGGACUUUAAAU

CCGGUUCUCCACUGGGGAGCGUGGGUUCAAAUCCCACCCGCGCC

CGCCA (SEQ ID NO: 54; M. maripaludis tRNA^UTuochre-variant 5);

GGCGCGGGUGGUUGAGCUUGGCCAAAGGCGCCGGACUUUAAAU

CCGGUUCUCCACUGGGGAGCGUGGGUUCAAAUCCCACCCCGCGC

CGCCA (SEQ ID NO: 55; M. maripaludis tRNA^UTuochre-variant 6);
or

GGGCGCGGGUGGUUGAGCUUGGCCAAAGGCGCCGGACUUUAAA

UCCGGUUCUCCACUGGGGAGCGUGGGUUCAAAUCCCACCCCGCG

CCCGCCA (SEQ ID NO: 56; M. maripaludis tRNA^UTuochre-variant 7).
```

A non-naturally occurring tRNA^Sec that is a chimeric M. maripaludis tRNA can have a nucleic acid sequence at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more identical to SEQ ID NO:33, 34, 35, 36, 37, 38, 39, 40, 41, 42, 43, 44, 45, 46, 47, 48, 49, 50, 51, 52, 53, 54, 55, or 56. Preferably the non-naturally occurring tRNA^Sec that is a chimeric M. maripaludis tRNA^Sec is characterized by one or more of the following elements: (1) the non-naturally occurring tRNA^Sec can be recognized by SerRS and by EF-Tu, or variants thereof; (2) when aminoacylated with serine the non-naturally occurring Ser-tRNA^Sec can be converted to non-naturally occurring Sec-tRNA^Sec by SelA or variant thereof; (3) when aminoacylated with serine the non-naturally occurring Ser-tRNA^Sec can be phosphorylated by PSTK or variant thereof (4) when aminoacylated with phosphorylated serine the non-naturally occurring Sep-tRNA^Sec can serve as a substrate for SepSecS or variant thereof.

5. Secondary Structure

The tRNAs disclosed herein typically include an acceptor arm, a D-arm, an anticodon arm, a variable arm, and a TΨC-arm, as described in more detail below.

a. Acceptor Arm

The non-naturally occurring tRNA^Sec disclosed herein includes an acceptor arm. The acceptor arm is the end of a tRNA molecule to which an amino acid becomes bound. It contains both the 5' and 3' ends of the tRNA. The 3'-terminal sequence of cytidine-cytidine-adenosine (CCA) overhangs the end, and the terminal A is the site of 'acceptance' of the amino acid.

The acceptor stem refers to the 5' and 3' sequences to the acceptor arm that form duplex RNA. The acceptor stem can be separate from the CCA overhang by one or more nucleotides, for example one or more guanine. In some embodiments, one or more nucleotides that separate the acceptor stem and the overhang are referred to as the discriminator base(s). For some tRNAs, the discriminator base preceding the CCA sequence at the 3' end is important for aminoacylation. The discriminator base can influence the stability of the base pair of the acceptor arm onto which it is stacked which can affect the energetic cost of opening the base pair and modulate the structure of the tRNA near the site of aminoacylation. For some aminoacyl-tRNA synthetases and other proteins that interact with tRNA, these factors could be important for specific recognition and/or formation of the transition state during catalysis (Lee et al., PNAS, 90(15): 7149-52 (1993)). In some embodiments, the acceptor stem and the CCA sequence are separated by a single guanine discriminator base.

The acceptor stem of the non-naturally occurring tRNA$^{Sec}$ disclosed herein typically include 4 to 12, preferably 5 to 11, more preferably 6 to 10, most preferably 7 to 9 base pairs of duplex RNA. In some embodiments, the acceptor stem is 7, 8, or 9 base pairs of duplex RNA.

The acceptor stem can be high in G-C content. For example, in some embodiments, the G-C content is 50%, 60%, 70%, 75%, 80%, 85%, 90%, 95%, or 100% of the nucleotides of the acceptor stem.

The 5' and 3' sequences of the tRNA that form the acceptor stem typically form a RNA duplex by Waston-Crick base pairing. The 5' and 3' sequences of the tRNA that form the acceptor stem are typically substantially complementary. Preferably, the 5' and 3' sequences of the tRNA that form the acceptor stem bind to or hybridize to each other under conditions of high stringency and specificity. In some embodiments, 5' sequence of the tRNA that forms the acceptor stem is 50%, 60%, 70%, 80%, 85%, 90%, 95%, or more complementary to the 3' sequence of the tRNA that forms the acceptor stem. In some embodiments the 5' and 3' sequences of the tRNA that form the acceptor stem are 100% complementary.

b. D-Arm

The non-naturally occurring tRNA$^{Sec}$ disclosed herein include a D-arm. The D-arm is typically composed of a D stem of duplex RNA and a D loop of non-duplex RNA. The D stem refers to the two segments of the tRNA primary sequence in the D-arm that form duplex RNA. The D stem of the non-naturally occurring tRNA$^{Sec}$ typically include 2 to 8, preferably 3 to 7, more preferably 4 to 6, base pairs of duplex RNA. In some embodiments, the D stem is 4, 5, or 6 base pairs of duplex RNA.

The D stem can be high in G-C content. For example, in some embodiments, the G-C content is 50%, 60%, 70%, 75%, 80%, 85%, 90%, 95%, or 100% of the nucleotides of the D stem.

The two segments of the tRNA that form the D stem typically form a RNA duplex by Waston-Crick base pairing. The two segments of the tRNA that form the D stem are typically substantially complementary. Preferably, the 5' and 3' sequences of the tRNA that form the acceptor stem bind to or hybridize to each other under conditions of high stringency and specificity. In some embodiments, 5' segment of the tRNA that forms the D stem is between 25% and 50% complementary to the 3' segment of the tRNA that forms the D stem. In some embodiments the 5' segment of the tRNA that forms the D stem is 50%, 60%, 70%, 80%, 85%, 90%, 95%, or more complementary to the 3' sequence of the tRNA that forms the D stem. In some embodiments the 5' and 3' sequences of the tRNA that form the D stem are 100% complementary.

The D loop refers to the part of the D-arm that does not form duplex RNA. The D loop's main function is that of recognition. The D loop can contain the base dihydrouracil. It is widely believed that it will act as a recognition site for aminoacyl-tRNA synthetase, which is an enzyme involved in the aminoacylation of the tRNA molecule. The D-loop can have between 3 and 15 nucleotides inclusive, preferably between 4 and 12 nucleotides inclusive. In some embodiments the D-loop has 4, 5, 6, 7, 8, 9, 10, 11, or 12 nucleotides.

c. Anticodon Arm

The non-naturally occurring tRNA$^{Sec}$ disclosed herein include an anticodon arm. The anticodon arm is typically composed of an anticodon stem of duplex RNA and an anticodon loop of non-duplex RNA. The anticodon stem refers to the two segments of the tRNA primary sequence in the anticodon arm that form duplex RNA. The anticodon stem of the non-naturally occurring tRNA$^{Sec}$ disclosed herein typically include 2 to 8, preferably 3 to 7, more preferably 4 to 6, base pairs of duplex RNA. In some embodiments, the anticodon stem is 4, 5, or 6 base pairs of duplex RNA.

The anticodon stem can be high in G-C content. For example, in some embodiments, the G-C content is 50%, 60%, 70%, 75%, 80%, 85%, 90%, 95%, or 100% of the nucleotides of the anticodon stem.

The two segments of the tRNA that form the anticodon stem typically form a RNA duplex by Waston-Crick base pairing. The two segments of the tRNA that form the anticodon stem are typically substantially complementary. Preferably, the 5' and 3' sequences of the tRNA that form the anticodon stem bind to or hybridize to each other under conditions of high stringency and specificity. In some embodiments the 5' segment of the tRNA that forms the anticodon stem is 50%, 60%, 70%, 80%, 85%, 90%, 95%, or more complementary to the 3' sequence of the tRNA that forms the anticodon stem. In some embodiments the 5' and 3' sequences of the tRNA that form the anticodon stem are 100% complementary.

The anticodon loop refers to the part of the anticodon-arm that does not form duplex RNA. The anticodon loop's main function is to present the anticodon sequence which can hybridize to the target codon in the mRNA sequence of interest. The anticodon sequence can be any three nucleotide sequence that binds by complementary base pairing to the target codon sequence in the mRNA of interest. In some embodiments, the anticodon pairs specifically with only one codon. Some anticodon sequences can pair with more than one codon (i.e., wobble base pairing). In some embodiments, the first nucleotide of the anticodon is inosine or pseudouridine, which can hydrogen bond to more than one base in the corresponding codon position.

In some embodiments, the anticodon hybridizes to a "stop" codon such as UAA, UAG, or UGA, preferably UAG (amber) or UGA (opal). Accordingly, in some embodiments the sequence of the anticodon is UUA, CUA, UCA, preferably CUA (amber) or UCA (opal) (in the 5' to 3' direction). The anticodon loop can have between 5 and 11 nucleotides inclusive, preferably about 7 nucleotides. In some embodiments the anticodon-loop has 5, 7, or 9 nucleotides. Typically, the three nucleotide anticodon sequence is flanked by an equal number of nucleotides both 5' and 3' of the anticodon sequence within the anticodon loop.

Although in some embodiments, the anti-codon is one that recognizes a stop codon, all other possible anti-codons (e.g., those that recognize an amino acid codon) are also specifically disclosed for all tRNA disclosed herein, including but not limited to SEQ ID NOS:1-92. Thus, in some embodiments, a non-naturally occurring tRNA includes the sequence of any one of SEQ ID NO:1-92, or a variant there with at least 80% sequence identity, wherein the anti-codon is substituted with an alternative anti-codon.

d. Variable Arm

The non-naturally occurring tRNA$^{Sec}$ disclosed herein includes a variable arm. The variable arm is typically composed of a variable stem of duplex RNA and a variable loop of non-duplex RNA. The variable stem refers to the two segments of the tRNA primary sequence in the variable arm that form duplex RNA. The variable stem of the non-naturally occurring tRNA$^{Sec}$ typically includes 2 to 8, preferably 3 to 7, more preferably 4 to 6, base pairs of duplex RNA. In some embodiments, the variable stem is 4, 5, or 6 base pairs of duplex RNA. In some embodiments the variable stem has 9, 10, 11, or more base pairs of duplex RNA.

The variable stem can be high in G-C content. For example, in some embodiments, the G-C content is 50%, 60%, 70%, 75%, 80%, 85%, 90%, 95%, or 100% of the nucleotides of the variable stem.

The two segments of the tRNA that form the variable stem typically form a RNA duplex by Waston-Crick base pairing. The two segments of the tRNA that form the anticodon stem are typically substantially complementary. Preferably, the 5' and 3' sequences of the tRNA that form the variable stem bind to or hybridize to each other under conditions of high stringency and specificity. In some embodiments the 5' segment of the tRNA that forms the variable stem is 50%, 60%, 70%, 80%, 85%, 90%, 95%, or more complementary to the 3' sequence of the tRNA that forms the variable stem. In some embodiments the 5' and 3' sequences of the tRNA that form the variable stem are 100% complementary.

The variable loop refers to the part of the variable-arm that does not form duplex RNA. The variable loop can have between 3 and 7 nucleotides inclusive, preferably between 4 and 6 nucleotides inclusive. In some embodiments the variable loop has 3, 4, 5, 6, or 7 nucleotides.

e. TΨC-Arm

The non-naturally occurring tRNA$^{Sec}$ disclosed herein includes a TΨC-arm (also referred to herein as a T-arm). The T-arm is the region on the tRNA molecule that acts as a recognition site for the ribosome, and allows a tRNA-ribosome complex to form during the process of protein biosynthesis. The T-arm is typically composed of a T stem of duplex RNA and a T loop of non-duplex RNA. The T stem refers to the two segments of the tRNA primary sequence in the T-arm that form duplex RNA. The T stem of the non-naturally occurring tRNA$^{Sec}$ typically includes 2 to 8, preferably 3 to 7, more preferably 4 to 6, base pairs of duplex RNA. In some embodiments, the T stem is 3, 4, or 5 base pairs of duplex RNA.

The T stem can be high in G-C content. For example, in some embodiments, the G-C content is 50%, 60%, 70%, 75%, 80%, 85%, 90%, 95%, or 100% of the nucleotides of the T stem.

The two segments of the tRNA that form the T stem typically form a RNA duplex by Waston-Crick base pairing. The two segments of the tRNA that form the T stem are typically substantially complementary. Preferably, the 5' and 3' sequences of the tRNA that form the acceptor stem bind to or hybridize to each other under conditions of high stringency and specificity. In some embodiments, 5' segment of the tRNA that forms the T stem is equal to or greater than 50% complementary to the 3' segment of the tRNA that forms the T stem. In some embodiments the 5' segment of the tRNA that forms the T stem is 50%, 60%, 70%, 80%, 85%, 90%, 95%, or more complementary to the 3' sequence of the tRNA that forms the T stem. In some embodiments the 5' and 3' sequences of the tRNA that form the T stem are 100% complementary.

The T loop refers to the part of the T-arm that does not form duplex RNA. In some embodiments the T-loop includes thymidine, pseudouridine, residues, or combinations thereof. The T-loop can have between 3 and 15 nucleotides inclusive, preferably between 4 and 12 nucleotides inclusive. In some embodiments the D-loop has 4, 5, 6, 7, 8, 9, 10, 11, or 12 nucleotides.

f. Linker Nucleotides

The five arms of the tRNA can be linked directly, or can be separated by one or more linker or spacer nucleotides to ensure the tRNA assumes the proper secondary structure. For example, the acceptor arm and the D-arm can separated by 0, 1, 2, 3, or more nucleotides; the D-arm and the anticodon arm can be separated by 0, 1, 2, 3, or more nucleotides; the anticodon arm and the variable arm can be separated by 0, 1, 2, 3, or more nucleotides; the variable arm and the T-arm can be separated by 0, 1, 2, 3, or more nucleotides; and the T-arm and the acceptor arm can be separated by 0, 1, 2, 3, or more nucleotides.

B. mRNA and Polypeptides of Interest

As discussed in more detail below, the non-naturally occurring tRNA$^{Sec}$ disclosed herein can be used in combination with an mRNA to manufacture selenocysteine containing polypeptides and proteins. The mRNA does not require, and preferably does not include, a SECIS element. The mRNA, which encodes a polypeptide of interest, includes one or more codons that is recognized by the anticodon of the Sec-tRNA$^{Sec}$, referred to herein as an "tRNA$^{Sec}$ recognition codon," such that tRNA catalyzes the attachment of a selenocysteine amino acid to the growing polypeptide chain during translation.

For example, if the tRNA$^{Sec}$ recognition codon is a stop codon, such as UGA, the mRNA will contain at least one UGA codon where a selenocysteine will be added to the growing polypeptide chain during translation. The tRNA$^{Sec}$ recognition codon can be added to or inserted into any mRNA to add a codon encoding selenocysteine at any desired location in the amino acid sequence. The tRNA$^{Sec}$ recognition codon can be substituted for any existing codon in the mRNA sequence so that any one or more amino acids from a reference polypeptide sequence is substituted with selenocysteine during translation. For example, as discussed in more detail below, in some embodiments, one or more codons encoding cysteine in a reference sequence are substituted with a tRNA$^{Sec}$ recognition sequence so that the one or more cysteines are replaced with selenocysteine during translation.

Various types of mutagenesis can be used to modify the sequence of a nucleic acid encoding the mRNA of interest to generate the tRNA$^{Sec}$ recognition codon. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, and mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis and double-strand break repair.

In some embodiments, the coding sequence, excluding the tRNA$^{Sec}$ recognition site as discussed above, is further altered for optimal expression (also referred to herein as "codon optimized") in an expression system of interest.

Methods for modifying coding sequences to achieve optimal expression are known in the art.

C. Isolated Nucleic Acid Molecules

Non-naturally occurring tRNA$^{Sec}$ and nucleic acids encoding non-naturally occurring tRNA$^{Sec}$ are disclosed. Also disclosed are mRNAs, cDNAs and other nucleic acids encoding proteins of interest that are engineered such that a tRNA$^{Sec}$, such as the non-naturally occurring tRNA$^{Sec}$ disclosed herein, "reads" at least one codon of the mRNA during translation of the protein encoded by the mRNA. As used herein, "isolated nucleic acid" refers to a nucleic acid that is separated from other nucleic acid molecules that are present in a genome, including nucleic acids that normally flank one or both sides of the nucleic acid in the genome. The term "isolated" as used herein with respect to nucleic acids also includes the combination with any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule or an RNA molecule, provided one of the nucleic acid sequences normally found immediately flanking that DNA molecule in a naturally-occurring genome is removed or absent. Thus, an isolated nucleic acid includes, without limitation, a DNA molecule or RNA molecule that exists as a separate molecule independent of other sequences (e.g., a chemically synthesized nucleic acid, or a cDNA, or RNA, or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule or RNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

Nucleic acids encoding the tRNA$^{Sec}$ and mRNA disclosed herein may be optimized for expression in the expression host of choice. In the case of nucleic acids encoding expressed polypeptides, codons may be substituted with alternative codons encoding the same amino acid to account for differences in codon usage between the organism from which the nucleic acid sequence is derived and the expression host. In this manner, the nucleic acids may be synthesized using expression host-preferred codons.

Nucleic acids can be in sense or antisense orientation, or can be complementary to a reference sequence, for example, a sequence encoding the disclosed tRNA$^{Sec}$ and mRNA. Nucleic acids can be DNA, RNA, nucleic acid analogs, or combinations thereof. Nucleic acid analogs can be modified at the base moiety, sugar moiety, or phosphate backbone. Such modification can improve, for example, stability, hybridization, or solubility of the nucleic acid. Modifications at the base moiety can include deoxyuridine for deoxythymidine, and 5-methyl-2'-deoxycytidine or 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) Antisense Nucleic Acid Drug Dev. 7:187-195; and Hyrup et al. (1996) Bioorgan. Med. Chem. 4:5-23. In addition, the deoxyphosphate backbone can be replaced with, for example, a phosphorothioate or phosphorodithioate backbone, a phosphoroamidite, or an alkyl phosphotriester backbone.

D. Methods for Producing Isolated Nucleic Acid Molecules

Isolated non-naturally occurring tRNA$^{Sec}$, nucleic acids encoding non-naturally occurring tRNA$^{Sec}$, and nucleic acids encoding polypeptides manufactured using the non-naturally occurring tRNA$^{Sec}$, are disclosed. Isolated nucleic acid molecules can be produced by standard techniques, including, without limitation, common molecular cloning and chemical nucleic acid synthesis techniques. For example, polymerase chain reaction (PCR) techniques can be used to obtain an isolated nucleic acid encoding a non-naturally occurring tRNA$^{Sec}$. PCR is a technique in which target nucleic acids are enzymatically amplified. Typically, sequence information from the ends of the region of interest or beyond can be employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995.

When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292-1293.

Isolated nucleic acids can be chemically synthesized, either as a single nucleic acid molecule or as a series of oligonucleotides (e.g., using phosphoramidite technology for automated DNA synthesis in the 3' to 5' direction). For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase can be used to extend the oligonucleotides, resulting in a single, double-stranded nucleic acid molecule per oligonucleotide pair, which then can be ligated into a vector. Isolated nucleic acids can also obtained by mutagenesis. Nucleic acids can be mutated using standard techniques, including oligonucleotide-directed mutagenesis and/or site-directed mutagenesis through PCR. See, *Short Protocols in Molecular Biology*. Chapter 8, Green Publishing Associates and John Wiley & Sons, edited by Ausubel et al, 1992. Examples of nucleic acid amino acid positions relative to a reference sequence that can be modified include those described herein.

E. Vectors and Host Cells

Vectors encoding non-naturally occurring tRNA$^{Sec}$ and polypeptides manufactured using the non-naturally occurring tRNA$^{Sec}$ are also provided. Nucleic acids, such as those described above, can be inserted into vectors for expression in cells. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. Operably linked means the disclosed sequences are incorporated into a genetic construct so that expression control sequences effectively control expression of a sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II).

A "promoter" as used herein is a DNA regulatory region capable of initiating transcription of a gene of interest. Some promoters are "constitutive," and direct transcription in the absence of regulatory influences. Some promoters are "tissue specific," and initiate transcription exclusively or selectively in one or a few tissue types. Some promoters are "inducible," and achieve gene transcription under the influence of an inducer. Induction can occur, e.g., as the result of a physiologic response, a response to outside signals, or as the result of artificial manipulation. Some promoters respond to the presence of tetracycline; "rtTA" is a reverse tetracycline controlled transactivator. Such promoters are well known to those of skill in the art.

To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Likewise, although tRNA$^{Sec}$ sequences do not encode a protein, control sequence can be operably linked to a sequence encoding a tRNA$^{Sec}$, to control expression of the tRNA$^{Sec}$ in a host cell. Methods of recombinant expression of tRNA from vectors is known in the art, see for example, Ponchon and Dardel, *Nature Methods*, 4(7):571-6 (2007); Masson and Miller, J. H., Gene, 47:179-183 (1986); Meinnel, et al., *Nucleic Acids Res.*, 16:8095-6 (1988); Tisné, et al., *RNA*, 6:1403-1412 (2000).

F. Host Cells

Host cell including the nucleic acids disclosed herein are also provided. Prokaryotes useful as host cells include, but are not limited to, gram negative or gram positive organisms such as *E. coli* or Bacilli. In a prokaryotic host cell, a polypeptide may include an N-terminal methionine residue to facilitate expression of the recombinant polypeptide in the prokaryotic host cell. The N-terminal Met may be cleaved from the expressed recombinant polypeptide. Promoter sequences commonly used for recombinant prokaryotic host cell expression vectors include lactamase and the lactose promoter system.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and a DNA sequence are inserted into the pBR322 vector. Other commercially available vectors include, for example, T7 expression vectors from Invitrogen, pET vectors from Novagen and pALTER® vectors and PinPoint® vectors from Promega Corporation.

In a prokaryotic host cell, a polypeptide may include an N-terminal methionine residue to facilitate expression of the recombinant polypeptide in the prokaryotic host cell. The N-terminal Met may be cleaved from the expressed recombinant polypeptide. Promoter sequences commonly used for recombinant prokaryotic host cell expression vectors include lactamase and the lactose promoter system.

In some embodiments, the host cells are *E. coli*. The *E. coli* strain can be a selA, selB, selC, deletion strain, or combinations thereof. For example, the *E. coli* can be a selA, selB, and selC deletion strain, or a selB and selC deletion strain. Examples of suitable *E. coli* strains include, but are not limited to, MI-IS and MH6.

Yeasts useful as host cells include, but are not limited to, those from the genus *Saccharomyces, Pichia, K. Actinomycetes* and *Kluyveromyces*. Yeast vectors will often contain an origin of replication sequence, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., J. Biol. Chem. 255:2073, (1980)) or other glycolytic enzymes (Holland et al., Biochem. 17:4900, (1978)) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Fleer et al., Gene, 107:285-195 (1991), in Li, et al., *Lett Appl Microbiol.* 40(5):347-52 (2005), Jansen, et al., *Gene* 344:43-51 (2005) and Daly and Hearn, *J. Mol. Recognit.* 18(2):119-38 (2005). Other suitable promoters and vectors for yeast and yeast transformation protocols are well known in the art.

In some embodiments, the host cells are eukaryotic cells. For example, mammalian and insect host cell culture systems well known in the art can also be employed to express non-naturally occurring tRNA$^{Sec}$ and mRNA for producing proteins or polypeptides containing selenocysteine. Commonly used promoter sequences and enhancer sequences are derived from Polyoma virus, Adenovirus 2, Simian Virus 40 (SV40), and human cytomegalovirus. DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are well known in the art.

Mammalian or insect host cell culture systems well known in the art can also be employed to express ribosomes (or a ribosomal rRNA thereof), tRNAs, synthetases or a combination thereof for producing proteins or polypeptides containing one or more dipeptides, non-standard-, non-natural-, or non-α-amino acids. Commonly used promoter sequences and enhancer sequences are derived from Polyoma virus, Adenovirus 2, Simian Virus 40 (SV40), and human cytomegalovirus. DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are well known in the art.

The host organism can be a genomically recoded organism "GRO." Typically, the GRO is a bacterial strain, for example, an $E.$ $coli$ bacterial strain, wherein a codon has been replaced by a synonymous codon. Because there are 64 possible 3-base codons, but only 20 canonical amino acids (plus stop codons), some amino acids are coded for by 2, 3, 4, or 6 different codons (referred to herein as "synonymous codons"). In a GRO, most or all of the iterations of a particular codon are replaced with a synonymous codon. The precursor strain of the GRO is recoded such that at a least one codon is completely absent from the genome. Removal of a codon from the precursor GRO allows reintroduction of the deleted codon in, for example, a heterologous mRNA of interest. As discussed in more detail below, the reintroduced codon is typically dedicated to a non-standard amino acid, which in the presence of the appropriate translation machinery, can be incorporated in the nascent peptide chain during translation of the mRNA.

Different organisms often show particular preferences for one of the several codons that encode the same amino acid, and some codons are considered rare or infrequent. Preferably, the replaced codon is one that is rare or infrequent in the genome. The replaced codon can be one that codes for an amino acid (i.e., a sense codon) or a translation termination codon (i.e., a stop codon). GRO that are suitable for use as host or parental strains for the disclosed systems and methods are known in the art, or can be constructed using known methods. See, for example, Isaacs, et al., $Science,$ 333, 348-53 (2011), Lajoie, et al., $Science$ 342, 357-60 (2013), Lajoie, et al., $Science,$ 342, 361-363 (2013).

Preferably, the replaced codon is one that codes for a rare stop codon. In a particular embodiment, the GRO is one in which all instances of the UAG (TAG) codon have been removed and replaced by another stop codon (e.g., TAA, TGA), and preferably wherein release factor 1 (RF1; terminates translation at UAG and UAA) has also been deleted, eliminating translational termination at UAG codons (Lajoie, et al., $Science$ 342, 357-60 (2013)). In a particular embodiment, the host or precursor GRO is C321.Δ A [321 UAG→UAA conversions and deletion of prfA (encodes RF1)] (genome sequence at GenBank accession CP006698). This GRO allows the reintroduction of UAG codons in a heterologous mRNA, along with orthogonal translation machinery (i.e., aminoacyl-tRNA synthetases (aaRSs) and tRNAs as discussed in more detail below), to permit efficient and site specific incorporation of non-standard amino acids into protein encoded by the recoded gene of interest. That is, UAG has been transformed from a nonsense codon (terminates translation) to a sense codon (incorporates amino acid of choice), provided the appropriate translation machinery is present. UAG is a preferred codon for recoding because it is the rarest codon in $Escherichia$ $coli$ MG1655 (321 known instances) and a rich collection of translation machinery capable of incorporating non-standard amino acids has been developed for UAG (Liu and Schultz, $Annu.$ $Rev.$ $Biochem.,$ 79:413-44 (2010)).

Stop codons include TAG (UAG), TAA (UAA), and TGA (UGA). Although recoding to UAG (TAG) is discussed in more detail above, it will be appreciated that either of the other stop codons (or any sense codon) can be recoded using the same strategy. Accordingly, in some embodiments, a sense codon is reassigned, e.g., AGG or AGA to CGG, CGA, CGC, or CGG (arginine), e.g., as the principles can be extended to any set of synonymous or even non-synonymous codons, that are coding or non-coding. Similarly, the cognate translation machinery can be removed/mutated/deleted to remove natural codon function (UAG--RF1, UGA-RF2). The orthogonal translation system, particularly the antisense codon of the tRNA, can be designed to match the reassigned codon.

GRO can have two, three, or more codons replaced with a synonymous or non-synonymous codon. Such GRO allow for reintroduction of the two, three, or more deleted codons in one or more recoded genes of interest, each dedicated to a different non-standard amino acid. Such GRO can be used in combination with the appropriate orthogonal translation machinery to produce polypeptides having two, three, or more different non-standard amino acids.

III. Methods for Manufacturing Proteins Containing Selenocysteine

A. Expression of Selenocysteine Containing Polypeptides

Generally, the canonical amino acids are charged onto their respective tRNA by their cognate aminoacyl-tRNA synthetase. The aminoacyl-tRNA is then delivered by EF-Tu to the ribosome (FIG. 1A). In contrast, the endogenous Sec pathway requires several biosynthetic steps. First, tRNA$^{Sec}$ is misacylated to Ser-tRNA$^{Sec}$ by SerRS. While in bacteria Ser-tRNA$^{Sec}$ is directly converted by SelA to Sec-tRNA$^{Sec}$, archaea and eukaryotes employ an additional phosphorylation step by PSTK to form Sep-tRNA$^{Sec}$, which is then converted by SepSecS to the final product Sec-tRNA$^{Sec}$ FIG. 1B. Sec-tRNA$^{Sec}$ is bound by elongation factor SelB and delivered to the ribosome. However, reassignment of the opal codon UGA to a Sec codon is only achieved if SelB also binds to the mRNA SECIS hairpin structure.

The compositions disclosed herein can be used to prepare polypeptides including one or more selenocysteine residues from mRNA that does not contain an SECIS element. The tRNA$^{Sec}$ disclosed herein is recognized by SerRS and misacylated to form the intermediate Ser-tRNA$^{Sec}$. Next the Ser-tRNA$^{Sec}$ is converted to Sec-tRNA$^{Sec}$ by SelA in prokaryotic system or hybrid systems, or PSTK and SepSecS in archaeal, eukaryotic, or hybrid systems. Finally, the Sec-tRNA$^{Sec}$ is delivered to the ribosome by EF-Tu, where the anticodon of the Sec-tRNA$^{Sec}$ recognizes the codon engineered to encode a Sec amino acid, and transfers the Sec onto the growing polypeptide chain. Accordingly, the non-naturally occurring tRNA$^{Sec}$ disclosed herein are typically recognized by SerRS, or a variant thereof, and when aminoacylated with serine the Ser-tRNA can (1) be a substrate for SelA or a variant thereof or (2) be a substrate for PSTK and when aminoacylated with phosphorylated serine the Sep-tRNA can serve as a substrate for SepSecS or a variant thereof, and (3) when aminoacylated, the non-naturally occurring Sec-tRNA$^{Sec}$ is recognized by EF-Tu.

As discussed in more detail below, recombinant proteins including selenocysteine can be prepared using in vitro transcription/translation or in vivo expression systems. The system can be of prokaryotic, eukaryotic, or archaeal origin or combinations thereof. For example, the system can be hybrid system including selenocysteine biogenesis and translation factors from prokaryotic, eukaryotic, archaeal origin, or combinations thereof. In some embodiments, the system is an in vivo prokaryotic expression including an *E. coli* strain in which the endogenous genes encoding selB, selC, or selA, selB, selC are deleted or mutated to reduce or eliminate expression of endogenous SelA, SelB, SelC or combinations thereof. The selB, selC, or selA, selB, selC mutant strains can be engineered to express a non-naturally occurring tRNA$^{Sec}$, as well as a PSTK and a SepSecS. In some embodiments recombinant SelA is expressed. The PSTK or SepSecS can of eukaryotic or archaeal origin, or a variant thereof. For example, in one embodiment, the PSTK is a *M. maripaludis* PSTK and the SepSecS is a *M. jannaschii* SepSecS. In some embodiments, SelA, PSTK and SepSecS are all expressed in the expression system.

In some embodiments selenocysteine biogenesis and translation factors are mutated to improve their specificity or activity for the non-naturally occurring tRNA$^{Sec}$. In the recombinant tRNA$^{Sec}$ biosynthetic pathway disclosed herein non-naturally occurring tRNA$^{Sec}$ is first misacylated to Ser-tRNA$^{Sec}$ by SerRS, and subsequently converted to Sec-tRNA$^{Sec}$ by SelA, or PSTK and SepSecS, or combinations thereof. Accordingly, if the SelA, or PSTK and SepSecS, enzymes are not 100% efficient at converting Ser-tRNA$^{Sec}$ to Sec-tRNA$^{Sec}$, the system may incorporate Sec or Ser at the desired position. Additionally, in some embodiments, recognition of the non-naturally occurring Sec-tRNA$^{Sec}$ by EF-Tu, is less efficient than EF-Tu recognition of other naturally occurring aminoacyl-tRNAs. Mutating the EF-Tu, SerRS, SelA, PSTK, SepSecS, or combinations thereof can improve the efficiency or recognition of the enzyme for the non-naturally occurring tRNA$^{Sec}$, the non-naturally occurring Sec-tRNA$^{Sec}$, or various intermediates thereof. Accordingly, in some embodiment, the EF-Tu, SerRS, SelA, PSTK, SepSecS, or combinations thereof are variants of a naturally occurring protein.

It is understood that if the tRNA$^{Sec}$ recognition codon of the mRNA of interest is one of the three mRNA stop codons (UAG, UAA, or UGA) translation of some of the mRNA of interest will terminate at each of the tRNA$^{Sec}$ recognition codons, resulting in a heterogeneous mixture of full-length and truncated proteins. Therefore, in some embodiments, the selenocysteine containing protein is expressed in a system that has been modified or mutated to reduce or eliminate expression of one or more translation release factors. A release factor is a protein that allows for the termination of translation by recognizing the termination codon or stop codon in an mRNA sequence. Prokaryotic release factors include RF1, RF2 and RF3; and eukaryotic release factors include eRF1 and eRF3.

Deletion of one or more release factors may result in "read-through" of the intended stop codon. Accordingly, some of recombinant proteins expressed in a system with one or more release factors may include one or more additional amino acids at the C-terminal end of the protein.

The protein of interest can be purified from the truncated proteins and other contaminants using standard methods of protein purification as discussed in more detail below.

1) In Vitro Transcription/Translation

In one embodiment, the genes encoding a non-naturally occurring tRNA$^{Sec}$, mRNA encoding the protein of interest, mRNA encoding EF-Tu, SerRS, SelA, PSTK, SepSecS, or combinations thereof are synthesized in vitro prior to or along with transcription and translation of the protein of interest. The synthesis of protein from a DNA sequence in vitro takes two steps. The first is transcription of an RNA copy and the second is the translation of a protein.

In vitro protein synthesis does not depend on having a polyadenylated RNA, but if having a poly(A) tail is essential for some other purpose a vector may be used that has a stretch of about 100 A residues incorporated into the polylinker region. That way, the poly(A) tail is "built in" by the synthetic method.

Eukaryotic ribosomes read RNAs more efficiently if they have a 5' methyl guanosine cap. RNA caps can be incorporated by initiation of transcription using a capped base analogue, or adding a cap in a separate in vitro reaction post-transcriptionally.

The use of in vitro translation systems can have advantages over in vivo gene expression when the over-expressed product is toxic to the host cell, when the product is insoluble or forms inclusion bodies, or when the protein undergoes rapid proteolytic degradation by intracellular proteases. Various approaches to in vitro protein synthesis are known in the art and include translation of purified RNA, as well as "linked" and "coupled" transcription:translation. In vitro translation systems can be eukaryotic or prokaryotic cell-free systems.

Combined transcription/translation systems are available, in which both phage RNA polymerases (such as T7 or SP6) and eukaryotic ribosomes are present. One example of a kit is the TNT® system from Promega Corporation.

Other suitable in vitro transcription/translation systems include, but are not limited to, the rabbit reticulocyte system, the *E. coli* S-30 transcription-translation system, and the wheat germ based translational system.

2) In Vivo Methods Transcription/Translation a. Extrachromosomal Expression

Host cells can be genetically engineered (e.g., transformed, transduced or transfected) with the vectors encoding non-naturally occurring tRNA$^{Sec}$ and a nucleic acid encoding the protein of interest, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (From et al., *Proc. Natl. Acad. Sci. USA* 82, 5824 (1985), infection by viral vectors, high velocity ballistic penetration by small particles with the nucleic acid either within the matrix of small beads or particles, or on the surface (Klein et al., *Nature* 327, 70-73 (1987)). Methods of expressing recombinant proteins in various recombinant expression systems including bacteria, yeast, insect, and mammalian cells are known in the art, see for example *Current Protocols in Protein Science* (Print ISSN: 1934-3655 Online ISSN: 1934-3663, Last updated January 2012).

Kits are commercially available for the purification of plasmids from bacteria, (see, e.g., GFX™ Micro Plasmid Prep Kit from GE Healthcare; Strataprep® Plasmid Miniprep Kit and StrataPrep® EF Plasmid Midiprep Kit from Stratagene; GenElute™ HP Plasmid Midiprep and Maxiprep Kits from Sigma-Aldrich, and, Qiagen plasmid prep kits and QIAfilter™ kits from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems.

Useful prokaryotic and eukaryotic systems for expressing and producing polypeptides are well known in the art include, for example, *Escherichia coli* strains such as BL-21, and cultured mammalian cells such as CHO cells.

In eukaryotic host cells, a number of viral-based expression systems can be utilized to express non-naturally occurring tRNA$^{Sec}$ and mRNA for producing proteins or polypeptides containing selenocysteine. Viral based expression systems are well known in the art and include, but are not limited to, baculoviral, SV40, retroviral, or vaccinia based viral vectors.

Mammalian cell lines that stably express tRNA and proteins can be produced using expression vectors with appropriate control elements and a selectable marker. For example, the eukaryotic expression vectors pCR3.1 (Invitrogen Life Technologies) and p91023(B) (see Wong et al. (1985) *Science* 228:810-815) are suitable for expression of recombinant proteins in, for example, Chinese hamster ovary (CHO) cells, COS-1 cells, human embryonic kidney 293 cells, NIH3T3 cells, BHK21 cells, MDCK cells, and human vascular endothelial cells (HUVEC). Additional suitable expression systems include the GS Gene Expression System™ available through Lonza Group Ltd.

Following introduction of an expression vector by electroporation, lipofection, calcium phosphate, or calcium chloride co-precipitation, DEAE dextran, or other suitable transfection method, stable cell lines can be selected (e.g., by metabolic selection, or antibiotic resistance to G418, kanamycin, or hygromycin or by metabolic selection using the Glutamine Synthetase-NS0 system). The transfected cells can be cultured such that the polypeptide of interest is expressed, and the polypeptide can be recovered from, for example, the cell culture supernatant or from lysed cells.

b. Expression by Genomic Integration

Methods of engineering a microorganism or cell line to incorporate a nucleic acid sequence into its genome are known in the art. For example, cloning vectors expressing a transposase and containing a nucleic acid sequence of interest between inverted repeats transposable by the transposase can be used to clone the stably insert the gene of interest into a bacterial genome (Barry, *Gene,* 71:75-84 (1980)). Stably insertion can be obtained using elements derived from transposons including, but not limited to Tn7 (Drahos, et al., *Bio/Tech.* 4:439-444 (1986)), Tn9 (Joseph-Liauzun, et al., *Gene,* 85:83-89 (1989)), Tn10 (Way, et al., *Gene,* 32:369-379 (1984)), and Tn5 (Berg, In *Mobile DNA*. (Berg, et al., Ed.), pp. 185-210 and 879-926. Washington, D.C. (1989)). Additional methods for inserting heterologous nucleic acid sequences in *E. coli* and other gram-negative bacteria include use of specialized lambda phage cloning vectors that can exist stably in the lysogenic state (Silhavy, et al., Experiments with gene fusions, Cold Spring Harbor Laboratory, Cold Spring Harbor, N.Y. (1984)), homologous recombination (Raibaud, et al., *Gene,* 29:231-241 (1984)), and transposition (Grinter, et al., *Gene,* 21:133-143 (1983), and Herrero, et al., *J. Bacteriology,* 172(11):6557-6567 (1990)).

Methods of engineering other microorganisms or cell lines to incorporate a nucleic acid sequence into its genome are also known in the art. Nucleic acids that are delivered to cells which are to be integrated into the host cell genome can contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can become integrated into the host genome. Techniques for integration of genetic material into a host genome are also known and include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

For example, cloning vectors expressing a transposase and containing a nucleic acid sequence of interest between inverted repeats transposable by the transposase can be used to clone the stably insert the gene of interest into a bacterial genome (Barry, *Gene,* 71:75-84 (1980)). Stably insertion can be obtained using elements derived from transposons including, but not limited to Tn7 (Drahos, et al., *Bio/Tech.* 4:439-444 (1986)), Tn9 (Joseph-Liauzun, et al., *Gene,* 85:83-89 (1989)), Tn10 (Way, et al., *Gene,* 32:369-379 (1984)), and Tn5 (Berg, In *Mobile DNA*. (Berg, et al., Ed.), pp. 185-210 and 879-926. Washington, D.C. (1989)). Additional methods for inserting heterologous nucleic acid sequences in *E. coli* and other gram-negative bacteria include use of specialized lambda phage cloning vectors that can exist stably in the lysogenic state (Silhavy, et al., Experiments with gene fusions, Cold Spring Harbor Laboratory, Cold Spring Harbor, N.Y. (1984)), homologous recombination (Raibaud, et al., *Gene,* 29:231-241 (1984)), and transposition (Grinter, et al., *Gene,* 21:133-143 (1983), and Herrero, et al., *J. Bacteriology,* 172(11):6557-6567 (1990)).

Integrative plasmids can be used to incorporate nucleic acid sequences into yeast chromosomes. See for example, Taxis and Knop, *Bio/Tech.,* 40(1):73-78 (2006), and Hoslot and Gaillardin, *Molecular Biology and Genetic Engineering of Yeasts*. CRC Press, Inc. Boca Raton, Fla. (1992). Methods of incorporating nucleic acid sequence into the genomes of mammalian lines are also well known in the art using, for example, engineered retroviruses such lentiviruses.

B. Purification of Selenocysteine Containing Polypeptides

Selenocysteine containing polypeptides can be isolated using, for example, chromatographic methods such as affinity chromatography, ion exchange chromatography, hydrophobic interaction chromatography, DEAE ion exchange, gel filtration, and hydroxylapatite chromatography. In some embodiments, selenocysteine containing polypeptides can be engineered to contain an additional domain containing amino acid sequence that allows the polypeptides to be captured onto an affinity matrix. For example, an Fc-containing polypeptide in a cell culture supernatant or a cytoplasmic extract can be isolated using a protein A column. In addition, a tag such as c-myc, hemagglutinin, polyhistidine, or Flag™ (Kodak) can be used to aid polypeptide purification. Such tags can be inserted anywhere within the polypeptide, including at either the carboxyl or amino terminus. Other fusions that can be useful include enzymes that aid in the detection of the polypeptide, such as alkaline phosphatase. Immunoaffinity chromatography also can be used to purify selenocysteine containing polypeptides. Selenocysteine containing polypeptides can additionally be engineered to contain a secretory signal (if there is not a secretory signal already present) that causes the protein to be secreted by the cells in which it is produced. The secreted proteins can then conveniently be isolated from the cell media.

In some embodiments, selenocysteine containing polypeptides are isolated using activated thiol SEPHAROSE®, for example, Activated Thiol SEPHAROSE® 4B. As discussed above, in the recombinant tRNA$^{Sec}$ biosynthetic pathway disclosed herein non-naturally occurring tRNA$^{Sec}$ is first misacylated to a non-naturally occurring Ser-tRNA$^{Sec}$ by SerRS, and subsequently converted to Sec-tRNA$^{Sec}$ by SelA, or PSTK and SepSecS, or combinations thereof. Accordingly, if the SelA, or PSTK and SepSecS, enzymes are not 100% efficient at converting Ser-tRNA$^{Sec}$ to Sec-tRNA$^{Sec}$, the system may incorporate Sec or Ser at the desired position, leading to a heterogeneous mixture of proteins. Activated thiol SEPHAROSE® can be incorporated into the protein purification process to purify Sec containing proteins from the Ser containing contaminants.

IV. Methods of Using Selenocysteine Containing Polypeptide

The compositions and methods disclosed herein can be used to manufacture polypeptides and proteins with one or more selenocysteine residues. In some embodiments, the mRNA encodes a polypeptide that is a naturally occurring selenocysteine containing polypeptide. In some embodiments, the mRNA encodes a polypeptide that is not a naturally occurring selenocysteine containing polypeptide. A nucleic acid sequence can include a codon that is recognized by the anticodon of a tRNA$^{Sec}$ disclosed herein, for example a nucleic acid encoding a naturally occurring selenocysteine containing protein, or can be modified to include a codon recognized by the anticodon of a tRNA$^{Sec}$. The nucleic acid sequence encoding the polypeptide can also be codon optimized for expression in the desired recombinant expression system. The nucleic acid can be expressed from a vector or incorporated into the genome of the desired expression system.

A. Recombinant Selenocysteine Containing Peptides—Naturally Occurring

The disclosed compositions and methods can be used for recombinant expression of naturally occurring selenocysteine containing peptides, or variants thereof. Selenoproteins exist in all major forms of life, including, eukaryotes, bacteria and archaea. Accordingly, in some embodiments, the mRNA of interest is an mRNA encoding a selenocysteine containing peptide from an eukaryote, a bacteria, or an archaea. The human genome encodes at least 25 naturally occurring selenocysteine containing peptides (Kryukov, et al, *Science*, 300:1439-1443 (2003)). Therefore, in some embodiments the mRNA encodes a iodothyronine deiodinase such as DIO1, DIO2, DIO3; a glutathione peroxidase such as GPX1, GPX2, GPX3, GPX4, or GPX6; a selenoprotein such as SelH, SelI, SelK, SelM, SelN, SelO, SelP, SelR, SelS, SelT, SelV, SelW, or Sel15; selenophosphate synthetase 2 (SPS2); or a thioredoxin reductase such as TXNRD1, TXNRD2, or TXNRD3.

Conditions to be Treated

In some embodiments, recombinant selenocysteine containing polypeptides prepared according to the claimed methods are administered to a subject in an effective amount to treat a disease, or one or more symptoms thereof. As discussed in Riaz and Mehmood, *JPMI*, 26(02):120-133 (2012) and Tapiero, et al., *Biomedicine & Pharmacotherapy* 57:134-144 (2003), many health effects of low selenium are thought to be due to lack of one or more specific selenocysteine containing proteins. For example, reduction or loss of one or more selenocysteine containing protein in a subject can be associated with increased oxidative stress in the subject. Accordingly, a recombinant selenocysteine containing protein can be administered to subject in an effective amount to increase antioxidant activity, or reduce oxidative stress in the subject. In some embodiments, the recombinant selenocysteine containing protein can be used to treat or prevent an age-related disorder, asthma, diabetes, an infectious disease, a cardiovascular disorder, a cancer, male infertility, pre-eclampsia, a gastrointestinal disorder, thyroid metabolism, or another diseases or condition associated with reduced levels or activity of selenocysteine containing proteins.

B. Recombinant Selenocysteine Containing Peptides—Non-Naturally Occurring

The disclosed compositions and methods can also be used for producing by recombinant expression a selenocysteine containing polypeptide variant of any polypeptide that does not naturally contain selenocysteine.

1. Insertion of Selenocysteine

One or more selenocysteines can be added to the beginning, end, and/or inserted into a polypeptide that does not typically have a selenocysteine. Adding one or more selenocysteines can change the biochemical and functional properties of the protein, for example, change the redox potential of the protein, increase the half-life of the protein, increase the stability or resistance to degradation, increase the activity of the protein (such as enzymatic activity), alter the pharmacokinetics of the protein, alter the binding affinity (such as the binding affinity of an antibody to antigen or ligand to receptor), change the folding properties of the protein, induce new epitopes onto the protein, or tag the protein for purification.

In some embodiments, the one or more selenocysteines changes the biochemical properties of the protein so it can be easily purified after recombinant expression. In some embodiments, selenocysteine can be added to a protein and used as a purification tag. For example, activated thiol SEPHAROSE®, or an equivalent thereof, can be incorporated into the protein purification process to purify Sec containing proteins from contaminants.

2. Substitution with Selenocysteine

In some embodiments, selenocysteine is substitute for one or more naturally occurring cysteines.

Reversible oxidation of thiols to disulfides or sulfenic acid residues controls biological functions in at least three general ways, by chemically altering active site cysteines, by altering macromolecular interactions, and by regulating activity through modification of allosteric Cys (reviewed in Jones, *Am. J. Physiol.*, 295(4):C849-868 (2008)). Half of all enzyme activities are sensitive to either oxidation, reaction with electrophiles, or interaction with metal ions. Enzymes with active-site Cys include caspases, kinases, phosphatases, and proteases. Cys is also a component of active sites of iron-sulfur clusters of electron transfer proteins and a element of zinc fingers in transcription factors and zinc-binding domains of metallothioneins. Cys residues are also conserved in structural proteins such as actin and docking proteins such as 14-3-3. Oxidation of Cys residues in αIIbβ3 integrin controls platelet activation. Cys-rich regions are present in plasma membrane receptors and ion channels, including the NMDA receptors, EGF receptor, and others. Thus reversible oxidation of active site thiols can provide a common and central "on-off" mechanism for control of cell functions.

β-Actin contains a conserved Cys, which results in reversible binding of proteins, S-GS-ylation, and crosslinking of actin filaments upon oxidation. Oxidation functions in glucocorticoid receptor translocation into nuclei, and oxidation controls export of yeast AP-1 (Yap-1) from nuclei. Disulfide crosslinks control fluidity of mucus. Such changes in protein structure and interaction due to reversible oxidation can provide a central mechanism for specificity in redox signaling. In addition to containing active site and/or structural thiols, many proteins contain Cys which regulate activity by an allosteric mechanism. This type of regulation can provide a "rheostat" rather than an "on-off" switch, thereby providing a means to throttle processes by GS-ylation or S-nitrosylation.

Many naturally occurring selenoproteins with known functions are oxidoreductases which contain catalytic redox-active Sec (Jacob C, et al., *Angew. Chem. Int. Ed. Engl.,* 42:4742-4758 (2003)). Variants of the naturally occurring selenoprotein in which the Sec residues are replaced with Cys residues are typically 100-1,000 times less active (Johansson L, et al, *Biochim. Biophys. Acta.,* 1726:1-13 (2005)). Furthermore, analogs of naturally occurring proteins where one or more Cys residues are replaced with Sec can generate analogs that retain the folding of the native peptides, are more potent, and have the same or greater biological activity (Raffa, *Life Sci.,* 87(15-16):451-6 (2010)).

Therefore, in some embodiments, the disclosed compositions and methods are used to manufacture recombinant variants or analogs where one or more naturally occurring Cys residues, for example Cys residues in the active site of an enzyme, are replaced with Sec residues. The methods and compositions can be used to generate analogs that retain a folding of the protein similar or the same as the native peptides, but are more potent while having the same or greater biological activity. Substituting one or more naturally occurring Cys residues with a Sec can increase the activity of the protein by 2, 5, 10, 100, 250, 500, 1,000 or more-fold over the activity of the protein that does not contain the Sec residue(s). Accordingly, the analogs can be used in therapeutic or research applications at a lower dosage, less frequently, with reduced toxicity, or combinations thereof relative to the naturally occurring protein.

In some embodiments, the disclosed compositions and methods can be used to prepare recombinant polypeptides where one or more cysteines that contributes to the formation of a disulfide bond in the protein is replaced with selenocysteine. Therefore, recombinant proteins having one or more Sec-Sec (diselenide) or Cys-Sec (selenocysteine-cysteine) bonds are disclosed.

A disulfide bond is a covalent bond, usually derived by the coupling of two thiol groups. Disulfide bonds in proteins are formed between the thiol groups of cysteine residues. A disulfide bond can stabilize the folded form of a protein in several ways. For example a disulfide bond can hold two portions of the protein together, favoring a folded topology and contributing to the formation and stability of secondary and tertiary structures. A disulfide bond can also form the center of a hydrophobic core in a folded protein, i.e., local hydrophobic residues may condense around the disulfide bond and onto each other through hydrophobic interactions. In some cases the hydrophobic core is an enzyme's active site, and the disulfide bond is necessary for enzymatic efficiency or activity.

A diselenide bond, which is formed between two selenocysteine residues, or a selenocysteine-cysteine bond between a selenocysteine and cysteine can impart similar structural and functional characteristics to the protein as a disulfide bond. Diselenide and selenocysteine-cysteine bonds are infrequent in nature, but have been reported to be in the active site of some enzymes, for example the selenocysteine protein SelL (Shchedrina, et al., *PNAS,* 104(35): 13919-13924 (2007)). Diselenide bonds have very low redox potential, but in some cases can be reduced by thioredoxin.

Therefore, in some embodiments, the disclosed compositions and methods are used to manufacture recombinant variants where one or more naturally occurring disulfide bonds are replaced with a diselenide or a selenocysteine-cysteine bond.

Replacing disulfide bonds with diselenide or selenocysteine-cysteine bonds can be used to reduce the redox potential of the bond, increase the half-life of the protein, increase the activity of the protein, alter the pharmacokinetics of the protein, for example, increase or decrease the association or dissociation constant, alter the folding and unfolding properties of the protein, or combinations thereof. For example, substituting one or more naturally occurring Cys residues with a Sec can increase the activity of the protein by 2, 5, 10, 100, 250, 500, 1,000 or more-fold over the activity of the protein that does not contain the Sec residue(s). Accordingly, the analogs can be used in therapeutic or research applications at a lower dosage, less frequently, with reduced toxicity, or combinations thereof relative to the naturally occurring protein.

Exemplary proteins where a naturally occurring Cys can be replaced with Sec according to the compositions and methods disclosed herein include, but are not limited to, caspases, kinases, phosphatases, proteases, transcription factors, metallothioneins, structural proteins such as actin and docking proteins such as 14-3-3, integrins such as αIIbβ3, plasma membrane receptors, ion channels, including the NMDA receptors, EGF receptor, and others.

The disclosed compositions and methods can be particularly useful for preparing recombinant antibodies, antigen binding fragments thereof, fusion proteins including a least one antibody domain (i.e., Ig fusion proteins) with altered properties, and receptor such as T cell receptors or receptor fragments including the binding domains. Antibodies contain inter-chain disulfide bonds which link the heavy and light chains, disulfide bonds that link two heavy chains, and disulfide bonds that link the two hinge regions. Antibodies also have disulfide bonds within the chains themselves (referred to as intra-chain disulfide bonds). The disclosed compositions and methods can be used to prepare recombinant antibodies where one or more disulfide bonds are replaced with diselenide bonds. The one or more of the inter-chain disulfide bonds which link the heavy and light chains, the disulfide bonds that link two heavy chains, the disulfide bonds that link the two hinge regions, the intra-chain disulfide bonds, or combinations thereof can be replaced with diselenide bonds.

Disulfide bonds in antibodies are important for assembly, stability and dimerization of the antibody. For example, disulfide bonds play a critical role in the stabilization of the immunoglobulin β-sandwich. Under reducing conditions, such as those characteristic of recombinant protein expression systems, disulfide bonds do not normally form and as a result most antibodies expressed in that compartment are misfolded or inactive (Seo, et al., *Protein Sci.,* 18(2): 259-267 (2009)). Furthermore, stability and homogeneity of therapeutic antibodies are important for safety and efficacy of therapeutic antibodies (McAuley, et al, *Protein Sci.,* 17(1): 95-106 (2008)). Undesired biochemical, structural, and conformational forms, such as those generated when disulfide bonds are reduced, can lead to loss of efficacy and risk of adverse side effects.

Replacing one or more of the disulfide bonds of an antibody with diselenide or selenocysteine-cysteine bonds according to the disclosed compositions and methods can improve the yield, purity, or combinations thereof, of recombinantly produced antibodies. Replacing one or more of the disulfide bonds of an antibody with diselenide or selenocysteine-cysteine bonds according to the disclosed compositions and methods can also improve stability, increase efficacy, increase half-life, reduce toxicity, alter the pharmacokinetics of the antibody, for example, increase or decrease the association or dissociation constant, or combinations thereof of antibodies, such as therapeutic antibodies.

The antibodies can be xenogeneic, allogeneic, syngeneic, or modified forms thereof, such as humanized, single chain or chimeric antibodies. Antibodies may also be anti-idiotypic antibodies specific for a idiotype of the desired antigen. The term "antibody" is also meant to include both intact molecules as well as fragments thereof that include the antigen-binding site and are capable of binding to a desired epitope. These include Fab and F(ab')$_2$ fragments which lack the Fc fragment of an intact antibody, and therefore clear more rapidly from the circulation, and may have less non-specific tissue binding than an intact antibody (Wahl et al., *J. Nuc. Med.* 24:316-325 (1983)). Also included are Fv fragments (Hochman, J. et al., *Biochemistry,* 12:1130-1135 (1973); Sharon, J. et al., *Biochemistry,* 15:1591-1594 (1976)). These various fragments can be produced using conventional techniques such as protease cleavage or chemical cleavage (see, e.g., Rousseaux et al., *Meth. Enzymol.,* 121:663-69 (1986)).

Antibody "formats" and methods of making recombinant antibodies are known in the art and reviewed in Laffly and Sodoyer, *Hum Antibodies,* 14(1-2):33-35 (2005). Methods of expressing and purifying antibodies from a recombinant expression system are known in the art, see for example, Knappik and Brundiers, "Recombinant Antibody Expression and Purification," *The Protein Protocols Handbook,* Third Edition Edited by: J. M. Walker© Humana Press, a Part of Springer Science+Business Media, LLC (2009).

Therapeutic antibodies that could benefit from replacement of one or more disulfide bonds with a diselenide or selenocysteine-cysteine bond are known in the art and include, but are not limited to, those discussed in Reichert, *Mabs,* 3(1): 76-99 (2011), for example, AIN-457, bapineuzumab, brentuximab vedotin, briakinumab, dalotuzumab, epratuzumab, farletuzumab, girentuximab (WX-G250), naptumomab estafenatox, necitumumab, obinutuzumab, otelixizumab, pagibaximab, pertuzumab, ramucirumab, REGN88, reslizumab, solanezumab, Tlh, teplizumab, trastuzumab emtansine, tremelimumab, vedolizumab, zalutumumab and zanolimumab.

Other therapeutic antibodies that could benefit from replacement of one or more disulfide bonds with a diselenide bond include antibodies approved for use, in clinical trials, or in development for clinical use which include, but are not limited to, rituximab (Rituxan®, IDEC/Genentech/Roche) (see for example U.S. Pat. No. 5,736,137), a chimeric anti-CD20 antibody approved to treat Non-Hodgkin's lymphoma; HuMax-CD20, an anti-CD20 currently being developed by Genmab, an anti-CD20 antibody described in U.S. Pat. No. 5,500,362, AME-133 (Applied Molecular Evolution), hA20 (Immunomedics, Inc.), HumaLYM (Intracel), and PRO70769 (PCT/US2003/040426, entitled "Immunoglobulin Variants and Uses Thereof"), trastuzumab (Herceptin®, Genentech) (see for example U.S. Pat. No. 5,677,171), a humanized anti-Her2/neu antibody approved to treat breast cancer; pertuzumab (rhuMab-2C4, Omnitarge), currently being developed by Genentech; an anti-Her2 antibody described in U.S. Pat. No. 4,753,894; cetuximab (Erbitux®, Imclone) (U.S. Pat. No. 4,943,533; PCT WO 96/40210), a chimeric anti-EGFR antibody in clinical trials for a variety of cancers; ABX-EGF (U.S. Pat. No. 6,235,883), currently being developed by Abgenix-Immunex-Amgen; HuMax-EGFr (U.S. Ser. No. 10/172,317), currently being developed by Genmab; 425, EMD55900, EMD62000, and EMD72000 (Merck KGaA) (U.S. Pat. No. 5,558,864; Murthy et al. 1987, Arch Biochem Biophys. 252(2):549-60; Rodeck et al., 1987, J Cell Biochem. 35(4):315-20; Kettleborough et al., 1991, Protein Eng. 4(7):773-83); 1CR62 (Institute of Cancer Research) (PCT WO 95/20045; Modjtahedi et al., 1993, J. Cell Biophys. 1993, 22(1-3):129-46; Modjtahedi et al., 1993, Br J Cancer. 1993, 67(2):247-53; Modjtahedi et al, 1996, Br J Cancer, 73(2):228-35; Modjtahedi et al, 2003, Int J Cancer, 105(2):273-80); TheraCIM hR3 (YM Biosciences, Canada and Centro de Immunologia Molecular, Cuba (U.S. Pat. No. 5,891,996; U.S. Pat. No. 6,506,883; Mateo et al, 1997, Immunotechnology, 3(1):71-81); mAb-806 (Ludwig Institute for Cancer Research, Memorial Sloan-Kettering) (Jungbluth et al. 2003, Proc Natl Acad Sci USA. 100(2): 639-44); KSB-102 (KS Biomedix); MRI-1 (IVAX, National Cancer Institute) (PCT WO 0162931A2); and SC100 (Scancell) (PCT WO 01/88138); alemtuzumab (Campath®, Millenium), a humanized mAb currently approved for treatment of B-cell chronic lymphocytic leukemia; muromonab-CD3 (Orthoclone OKT3®), an anti-CD3 antibody developed by Ortho Biotech/Johnson & Johnson, ibritumomab tiuxetan (Zevalin®), an anti-CD20 antibody developed by IDEC/Schering AG, gemtuzumab ozogamicin (Mylotarg®), an anti-CD33 (p67 protein) antibody developed by Celltech/Wyeth, alefacept (Amcvive®), anti-LFA-3 Fc fusion developed by Biogen), abciximab (ReoPro®), developed by Centocor/Lilly, basiliximab (Simulect®), developed by Novartis, palivizumab (Synagis®), developed by Medimmune, infliximab (Remicade®), an anti-TNFalpha antibody developed by Centocor, adalimumab (Humira®), an anti-TNFalpha antibody developed by Abbott, Humicade®, an anti-TNFalpha antibody developed by Celltech, golimumab (CNTO-148), a fully human TNF antibody developed by Centocor, etanercept (Enbrel®), an p75 TNF receptor Fc fusion developed by Immunex/Amgen, Ienercept, an p55TNF receptor Fc fusion previously developed by Roche, ABX-CBL, an anti-CD 147 antibody being developed by Abgenix, ABX-IL8, an anti-IL8 antibody being developed by Abgenix, ABX-MA1, an anti-MUC18 antibody being developed by Abgenix, Pemtumomab (R1549,90Y-muH-MFG1), an anti-MUC1 in development by Antisoma, Therex (R1550), an anti-MUC1 antibody being developed by Antisoma, AngioMab (AS1405), being developed by Antisoma, HuBC-1, being developed by Antisoma, Thioplatin (AS1407) being developed by Antisoma, Antegrene (natalizumab), an anti-alpha-4-beta-1 (VLA-4) and alpha-4- beta-7 antibody being developed by Biogen, VLA-1 mAb, an anti-VLA-1 integrin antibody being developed by Biogen, LTBR mAb, an anti-lymphotoxin beta receptor (LTBR) antibody being developed by Biogen, CAT-152, an anti-TGF-.beta.2 antibody being developed by Cambridge Antibody Technology, ABT 874 (J695), an anti-IL-12 p40 antibody being developed by Abbott, CAT-192, an anti-TGF.beta.1 antibody being developed by Cambridge Antibody Technology and Genzyme, CAT-213, an anti-Eotaxinl antibody being developed by Cambridge Antibody Technology, LyntphoStat-B® an anti-Blys antibody being developed by Cambridge Antibody Technology and Human Genome Sciences Inc., TRAIL-R1mAb, an anti-TRAIL-R1 antibody being developed by Cambridge Antibody Technology and Human Genome Sciences, Inc. Avastin® bevacizumab, rhuMAb-VEGF), an anti-VEGF antibody being developed by Genentech, an anti-HER receptor family antibody being developed by Genentech, Anti-Tissue Factor (ATF), an anti-Tissue Factor antibody being developed by Genentech. Xolair® (Omalizurnab), an anti-IgE antibody being developed by Genentech, Raptiva® (Efalizumab), an anti-CD11a antibody being developed by Genentech and Xoma, MLN-02 Antibody (formerly LDP-02), being developed by Genentech and Millenium Pharmaceuticals, HuMax CD4, an anti-CD4 antibody being developed by Genmab, HuMax-IL15, an anti-IL15 antibody being developed by Genmab and Amgen, HuMax-Inflam, being developed by Genmab and Medarex, HuMax-Cancer, an anti-Heparanase I antibody being developed by Genmab and Medarex and Oxford GcoSciences, HuMax-Lymphoma, being developed by Genmab and Amgen, HuMax-TAC, being developed by Genmab, IDEC-131, and anti-CD40L antibody being developed by IDEC Pharmaceuticals, IDEC-151 (Clenoliximab), an anti-CD4 antibody being developed by IDEC Pharmaceuticals, IDEC-114, an anti-CD80 antibody being developed by IDFC Pharmaceuticals, IDEC-152, an anti-CD23 being developed by IDEC Pharmaceuticals, anti-macrophage migration factor (MIF) antibodies being developed by IDEC Pharmaceuticals, BEC2, an anti-idiotypic antibody being developed by Imclone, IMC-1C11, an anti-KDR antibody being developed by Imclone, DC101, an anti-flk-1 antibody being developed by Imclone, anti-VE cadherin antibodies being developed by Imclone, CEA-Cide® (labetuzumab), an anti-carcinoembryonic antigen (CEA) antibody being developed by Immunomedics, LymphoCide® (Epratuzumab), an anti-CD22 antibody being developed by Immunomedics, AFP-Cide, being developed by Immunomedics, MyelomaCide, being developed by Immunomedics, LkoCide, being developed by Immunomedics, ProstaCide, being developed by Immunomedics, MDX-010, an anti-CTLA4 antibody being developed by Medarex, MDX-060, an anti-CD30 antibody being developed by Medarex, MDX-070 being developed by Medarex, MDX-018 being developed by Medarex, Osidem® (IDM-0, and anti-Her2 antibody being developed by Medarex and Immuno-Designed Molecules, HuMaxe-CD4, an anti-CD4 antibody being developed by Medarex and Genmab, HuMax-IL15, an anti-IL15 antibody being developed by Medarex and Genmab, CNTO 148, an anti-TNFα antibody being developed by Medarex and Centocor/J&J. CNTO 1275, an anti-cytokine antibody being developed by Centocor/J&J, MOR101 and MOR102, anti-intercellular adhesion molecule-1 (ICAM-1) (CD54) antibodies being developed by MorphoSys, MOR201, an anti-fibroblast growth factor receptor 3 (FGFR-3) antibody being developed by MorphoSys, Nuvion® (visilizumab), an anti-CD3 antibody being developed by Protein Design Labs, HuZAFO, an anti-gamma interferon antibody being developed by Protein Design Labs, Anti-α5β1 Integrin, being developed by Protein Design Labs, anti-IL-12, being developed by Protein Design Labs, ING-1, an anti-Ep-CAM antibody being developed by Xoma, Xolair® (Omalizumab) a humanized anti-IgE antibody developed by Genentech and Novartis, and MLN01, an anti-Beta2 integrin antibody being developed by Xoma. In another embodiment, the therapeutics include KRN330 (Kirin); huA 33 antibody (A33, Ludwig Institute for Cancer Research); CNTO 95 (alpha V integrins, Centocor); MEDI-522 (alpha V133 integrin, Medimmune); volociximab (αVβ1 integrin, Biogen/PDL); Human mAb 216 (B cell glycosolated epitope, NCI); BiTE MT103 (bispecific CD19×CD3, Medimmune); 4G7×H22 (Bispecific Bcell× FcgammaR1, Meclarex/Merck KGa); rM28 (Bispecific CD28×MAPG, U.S. Patent No. EP1444268); MDX447 (EMD 82633) (Bispecific CD64×EGFR, Medarex); Catumaxomab (removah) (Bispecific EpCAM×anti-CD3, Trion/Fres); Ertumaxomab (bispecific HER2/CD3, Fresenius Biotech); oregovomab (OvaRex) (CA-125, ViRexx); Rencarex® (WX G250) (carbonic anhydrase IX, Wilex); CNTO 888 (CCL2, Centocor); TRC105 (CD105 (endoglin), Tracon); BMS-663513 (CD137 agonist, Brystol Myers Squibb); MDX-1342 (CD19, Medarex); Siplizumab (MEDI-507) (CD2, Medimmune); Ofatumumab (Humax-CD20) (CD20, Genmab); Rituximab (Rituxan) (CD20, Genentech); THIOMAB (Genentech); veltuzumab (hA20) (CD20, Immunomedics); Epratuzumab (CD22, Amgen); lumiliximab (IDEC 152) (CD23, Biogen); muromonab-CD3 (CD3, Ortho); HuM291 (CD3 fc receptor, PDL Biopharma); HeFi-1, CD30, NCI); MDX-060 (CD30, Medarex); MDX-1401 (CD30, Medarex); SGN-30 (CD30, Seattle Genetics); SGN-33 (Lintuzumab) (CD33, Seattle Genetics); Zanolimumab (HuMax-CD4) (CD4, Genmab); HCD 122 (CD40, Novartis); SGN-40 (CD40, Seattle Genetics); Campathlh (Alemtuzumab) (CD52, Genzyme); MDX-1411 (CD70, Medarex); hLL1 (EPB-I) (CD74.38, Immunomedics); Galiximab (IDEC-144) (CD80, Biogen); MT293 (TRC093/D93) (cleaved collagen, Tracon); HuLuc63 (CS1, PDL Pharma); ipilimumab (MDX-010) (CTLA4, Brystol Myers Squibb); Tremelimumab (Ticilimumab, CP-675,2) (CTLA4, Pfizer); 1-IGS-ETR1 (Mapatumumab) (DR4TRAIL-R1 agonist, Human Genome Science/Glaxo Smith Kline); AMG-655 (DR5, Amgen); Apomab (DR5, Genentech); CS-1008 (DR5, Daiichi Sankyo); HGS-ETR2 (lexatumumab) (DR5TRAIL-R2 agonist, HGS); Cetuximab (Erbitux) (EGFR, Imclone); IMC-11F8, (EGFR, Imclone); Nimotuzumab (EGFR, YM Bio); Panitumumab (Vectabix) (EGFR, Amgen); Zalutumumab (HuMaxEGFr) (EGFR, Genmab); CDX-110 (EGFRvIII, AVANT Immunotherapeutics); adecatumumab (MT201) (Epcam, Merck); edrecolomab (Panorex, 17-1A) (Epcam Glaxo/Centocor); MORAb-003 (folate receptor a, Morphotech); KW-2871 (ganglioside GD3, Kyowa); MORAb-009 (GP-9, Morphotech); CDX-1307 (MDX-1307) (hCGb, Celldex); Trastuzumab (Herceptin) (HER2, Celldex); Pertuzumab (rhuMAb 2C4) (HER2 (DI), Genentech); apolizumab (HLA-DR beta chain, PDL Pharma); AMG-479 (IGF-1R, Amgen); anti-IGF-1R R1507 (IGF1-R, Roche); CP 751871 (IGF 1-R, Pfizer); IMC-A12 (IGF1-R, Imclone); B1111022 Biogen); Mik-beta-1 (IL-2Rb (CD122), Hoffman LaRoche); CNTO 328 (IL6, Centocor); Anti-MR (1-7F9) (Killer cell Ig-like Receptor (MR), Novo); Hu3S193 (Lewis (y), Wyeth, Ludwig Institute of Cancer Research); hCBE-11 (LTβR, Biogen); HuHMFG1 (MUC1, Antisoma/NCI); RAV 12 (N-linked carbohydrate epitope, Raven); CAL (parathyroid hormone-related protein (PTH-rP), University of California); CT-011 (PD1, CtireTech); MDX-1106 (ono-4538) (PDL Nileclarox/Ono); MAb CT-011 (PD1, Curetech); IMC-3G3 (PDGFRa, Imclone); bavituximab (phosphatidyl-serine, Peregrine); huJ591 (PSMA, Cornell Research Foundation); muJ591 (PSMA, Cornell Research Foundation); GC1008 (TGFb (pan) inhibitor (IgG4), Genzyme); Infliximab (Remicade) (TNFα, Centocor); A27.15 (transferrin receptor, Salk Institute, INSERN WO 2005/111082); E2.3 (transferrin receptor, Salk Institute); Bevacizumab (Avastin) (VEGF, Genentech); HuMV833 (VEGF, Tsukuba Research Lab-WO/2000/034337, University of Texas); IMC-18F1 (VEGFR1, Imclone); IMC-1121 (VEGFR2, Imclone)

In another embodiment, the recombinant protein is a fusion protein having a least one Cys, preferably at least one Cys-Cys bond. In some embodiments, the fusion protein is a fusion protein containing an antibody domain, for example an Ig fusion protein. A fusion protein typically includes two or more domains, where a first domain including a peptide of interest is fused, directly or indirectly to a second polypeptide. In some embodiments, the second domain includes one or more domains of an Ig heavy chain constant region, preferably having an amino acid sequence corresponding to the hinge, $C_{H2}$ and $C_{H3}$ regions of a human immunoglobulin Cγ1 chain. Construction of immunoglobulin fusion proteins is discussed in *Current Protocols in Immunology*, (ed. Diane Hollenbaugh, Alejandro Aruffo) *UNIT* 10.19A, Published May 1, 2002, by John Wiley and Sons, Inc.

3. Selenocysteine-Containing Polypeptide Conjugates

In some embodiments, the addition of one or more selenocysteines can be used to facilitate linkage of second therapeutic, prophylactic or diagnostic agent to the selenocysteine containing polypeptide. Methods of utilizing cysteines as reactive sites for attachment of a second agent, for example, via a disulfide bridge, are known in the art. See for example, Ritter, *Pharmaceutical Technology*, 42-47 (2012), Miao, et al., *Bioconjug. Chem.*, 19(1):15-19 (2008); and Dosio, et al., *Toxins (Basel)*, 3(7):848-83 (2011). Accordingly, one or more selenocysteines can be added to a recombinant polypeptide, or substitute for an existing amino acid such as cysteine, to create or replace a reactive site for conjugation of the second agent. The recombinant polypeptide and the second agent can be conjugated via a linker. In a preferred embodiment, the recombinant polypeptide engineered to a contain one or more selenocysteines is an antibody, for example a therapeutic antibody.

In some embodiments, the second agent is a toxin, diagnostic imaging agent, purification ligand or other engineered element that modifies the stability, activity, pharmacokinetics, or other properties of the protein. The second agent can be a small molecule.

In a preferred embodiment, the second agent is a therapeutic agent. For example, the second agent can be a chemotherapeutic drug. The majority of chemotherapeutic drugs can be divided into: alkylating agents, antimetabolites, anthracyclines, plant alkaloids, topoisomerase inhibitors, and other antitumour agents. All of these drugs affect cell division or DNA synthesis and function in some way. Additional therapeutics include monoclonal antibodies and the new tyrosine kinase inhibitors e.g. imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to, cisplatin, carboplatin, oxaliplatin, mechlorethamine, cyclophosphamide, chlorambucil, vincristine, vinblastine, vinorelbine, vindesine, taxol and derivatives thereof, irinotecan, topotecan, amsacrine, etoposide, etoposide phosphate, teniposide, epipodophyllotoxins, trastuzumab (HERCEPTIN®), cetuximab, and rituximab (RITUXAN® or MABTHERA®), bevacizumab (AVASTIN®), and combinations thereof.

In some preferred embodiments, recombinant antibody including one or more selenocysteine polypeptides manufactured according to the disclosed methods is conjugated with second therapeutic agent such as a chemotherapeutic drug.

Conditions to be Treated

As discussed above, substituting one or more naturally occurring Cys residues with a Sec can increase activity, lower dosage, reduce toxicity, improve stability, increase efficacy, increase half-life or combinations thereof of a selenocysteine containing protein relative to its cysteine containing counterpart. Accordingly, therapeutic proteins containing one or more selenocysteine residues can be prepared according to the compositions and methods disclosed herein and administered to a subject in need thereof in an effective amount to reduce or alleviate one or more symptoms of a disease or disorder. Therapeutic proteins such as enzymes and antibodies which contain one or more cysteine residues or disulfide bonds can be replaced with Sec to increase activity, lower dosage, reduce toxicity, improve stability, increase efficacy, increase half-life, or attach a second agent or combinations thereof are discussed above and known in the art, and can be administered to subject to treat diseases or disorders including, but not limited to, infectious diseases, cancers, metabolic disorders autoimmune disorders, inflammatory disorders, and age-related disorders.

C. Administration

The recombinant selenocysteine containing polypeptides disclosed herein can be part of a pharmaceutical composition. The compositions can be administered in a physiologically acceptable carrier to a host. Preferred methods of administration include systemic or direct administration to a cell. The compositions can be administered to a cell or patient, as is generally known in the art for protein therapy applications.

The compositions can be combined in admixture with a pharmaceutically acceptable carrier vehicle. Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween®, Pluronics® or PEG.

The compositions can be administered parenterally. As used herein, "parenteral administration" is characterized by administering a pharmaceutical composition through a physical breach of a subject's tissue. Parenteral administration includes administering by injection, through a surgical incision, or through a tissue-penetrating non-surgical wound, and the like. In particular, parenteral administration includes subcutaneous, intraperitoneal, intravenous, intraarterial, intramuscular, intrasternal injection, and kidney dialytic infusion techniques.

Parenteral formulations can include the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Parenteral administration formulations include suspensions, solutions, emulsions in oily or aqueous vehicles, pastes, reconstitutable dry (i.e. powder or granular) formulations, and implantable sustained-release or biodegradable formulations. Such formulations may also include one or more additional ingredients including suspending, stabilizing, or dispersing agents. Parenteral formulations may be prepared, packaged, or sold in the form of a sterile injectable aqueous or oily suspension or solution. Parenteral formulations may also include dispersing agents, wetting agents, or suspending agents described herein.

Methods for preparing these types of formulations are known. Sterile injectable formulations may be prepared using non-toxic parenterally-acceptable diluents or solvents, such as water, 1,3-butane diol, Ringer's solution, isotonic sodium chloride solution, and fixed oils such as synthetic monoglycerides or diglycerides. Other parentally-administrable formulations include microcrystalline forms, liposomal preparations, and biodegradable polymer systems. Compositions for sustained release or implantation may include pharmaceutically acceptable polymeric or hydrophobic materials such as emulsions, ion exchange resins, sparingly soluble polymers, and sparingly soluble salts.

Pharmaceutical compositions may be prepared, packaged, or sold in a buccal formulation. Such formulations may be in the form of tablets, powders, aerosols, atomized solutions, suspensions, or lozenges made using known methods, and may contain from about 0.1% to about 20% (w/w) active ingredient with the balance of the formulation containing an orally dissolvable or degradable composition and/or one or more additional ingredients as described herein. Preferably, powdered or aerosolized formulations have an average particle or droplet size ranging from about 0.1 nanometers to about 200 nanometers when dispersed.

As used herein, "additional ingredients" include one or more of the following: excipients, surface active agents, dispersing agents, inert diluents, granulating agents, disintegrating agents, binding agents, lubricating agents, sweetening agents, flavoring agents, coloring agents, preservatives, physiologically degradable compositions (e.g., gelatin), aqueous vehicles, aqueous solvents, oily vehicles and oily solvents, suspending agents, dispersing agents, wetting agents, emulsifying agents, demulcents, buffers, salts, thickening agents, fillers, emulsifying agents, antioxidants, antibiotics, antifungal agents, stabilizing agents, and pharmaceutically acceptable polymeric or hydrophobic materials. Other "additional ingredients" which may be included in the pharmaceutical compositions are known. Suitable additional ingredients are described in Remington's Pharmaceutical Sciences, Mack Publishing Co., Genaro, ed., Easton, Pa. (1985).

Dosages and desired concentrations of the pharmaceutical compositions disclosed herein may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

EXAMPLES

Example 1: Construction of Exemplary Non-Naturally Occurring tRNA$^{Sec}$

PSTK recognizes certain key bases (called identity elements) in the Sep-tRNA$^{Sec}$ substrate. These have been investigated by tRNA mutagenesis and subsequent transplantation of the tRNA$^{Sec}$ identity elements into a tRNA$^{Ser}$ body. The major M. maripaludis tRNA$^{Sec}$ identity elements G2-C71 and C3-G70 were transplanted into M. maripaludis tRNA$^{Ser}$ UGA.

Mutation of the tRNA$^{Ser}$ negative determinant A5-U68 to the C5-G68 base pair present in tRNA$^{Sec}$ resulted in a tRNA$^{Sec}$ variant that phosphorylated with a relative efficiency of 68% as compared to wild-type tRNA$^{Sec}$.

Another mutant tRNA with an 8 bp acceptor stem (FIG. 4A) could be converted to Sep-tRNA$^{Sec}$ with 31% relative efficiency.

Thus, different variants of M. maripaludis tRNA$^{Ser}$ and tRNA$^{Sec}$ are properly recognized by PSTK.

Since E. coli is a system for Sec incorporation, tRNA$^{UTu}$ candidates derived from the E. coli tRNA$^{Ser}$ body were also designed (FIGS. 3 and 4). E. coli tRNA$^{Ser}$ serves as a major scaffold for tRNA$^{UTu}$, with the exception of the acceptor stem that originates from E. coli tRNA$^{Sec}$ (FIG. 3, center panel, boxed sequence elements). Major EF-Tu recognition elements were retained from tRNA$^{Ser}$ as well (FIG. 3, center panel, circled sequence elements). The amber anti-codon CUA constitutes tRNA$^{UTu}_{am}$ whereas the opal anti-codon UCA constitutes tRNA$^{UTu}_{op}$.

The experiments described below utilize the tRNA$^{UTu}_{am}$ or the tRNA$^{UTu}_{op}$, depicted in FIG. 3, center panel (SEQ ID NO:7 and SEQ ID NO:6 respectively), as indicated.

Example 2: Ser-tRNA$^{UTu}_{am}$ Forms Sec-tRNA$^{UTu}_{am}$

In vitro Ser-tRNA$^{UTu}_{am}$ conversion was confirmed by TLC separation of [$^{32}$P] Amp, [$^{32}$P] Ser-Amp and [$^{32}$P] Sec-Amp recovered by nuclease P1, treatment from [$\alpha^{32}$P] ATP radiolabeled tRNA$^{UTu}_{am}$, tRNA$^{UTu}_{am}$ after serylation and Ser-tRNA$^{UTu}_{am}$ after incubation in an in vitro Sec formation assay. The TLC was developed for 90 min under acidic conditions using 100 mM ammonium acetate and 5% acetic acid.

Example 3: tRNA$^{UTu}$ Forms the Active Selenoenzyme Formate Dehydrogenase H

Formate Dehydrogenase H (FDH$_H$) is a selenocysteine containing E. coli enzyme of known structure (Boyington, et al., Science, 275:1305-08 (1997)). A sequence encoding wildtype FDH$_H$ (FDH$_{Hop}$) or an FDH$_H$ (FDH$_{Ham}$) engineered to replace the opal codon with an amber codon was expressed in e. coli strain MH5 (BW25113 selA selB fdhF).

As shown in FIG. 5, tRNA$^{UTu}$ mediates functional Sec suppression in FDH$_H$ E. coli strain MH5 which was complemented with E. coli SelA, M. jannaschii PSTK, and either tRNA$^{UTu}{}_{op}$ and FDH$_{H\,op}$ (1) or tRNA$^{UTu}{}_{am}$ and FDH$_{H\,am}$ (4) and grown anaerobically on LB selective medium supplemented with 0.01 mM IPTG at 30° C. for 24 h. Controls used the same experimental setup with either tRNA$^{UTu}{}_{op}$ (2) or tRNA$^{UTu}{}_{am}$ (3) omitted and tested the combinations of FDH$_{H\,op}$ and FDH$_{H\,am}$ with genomically encoded *E. coli* tRNA$^{Sec}$ and plasmid encoded selB instead. Cells were overlaid with a top agar containing sodium formate and benzyl viologen. FDH$_H$ activity was then assessed by occurrence of a purple coloration upon reduction of benzyl viologen.

Example 4: $^{75}$Se Incorporates into *E. coli* Selenoprotein FDH$_H$

Cells were grown in the presence of [$^{75}$Se]-selenite in LB medium supplemented with 100 μM IPTG for protein overexpression.

6×His-tagged FDH$_H$ fusion protein was purified and detected by SDS-Page and autoradiography of the gel, with FDH$_H$ corresponding to the protein band at a relative molecular weight of approximately 80,000 Da.

Example 5: Sec Complements Thymidylate Synthase A Active Site Residue Cys146

Thymidylate Synthase (ThyA) is an *E. coli* enzyme with a Cys in the active site. When the Cys is replaced with a Ser, the protein loses its enzymatic activity.

As shown in FIG. 6, *E. coli* MH6 (lacking ThyA) was complemented with expression constructs encoding either ThyA$_{WTCys}$ (Cys146), ThyA$_{Ser}$ (Cys146Ser) or ThyA$_{am}$ (Cys146Sec) alongside with tRNA$^{UTu}{}_{am}$ and SelA.

All clones showed growth on LB agar plates while only ThyA$_{am}$ (Cys146Sec) was able to reconstitute the wild type phenotype (ThyA$_{WTCys}$) on M9 minimal medium in the absence of thymine.

Example 6: Characterization of Grx1 and GPx1 Mutants

Glutaredoxin-1 (Grx1) is an enzyme with a Cys in the active site, which is inactive when replaced with a Ser. Constructs were created for expression of Grx1$_{C11am/C14S}$Sec (where the Cys 11 codon is replaced with an amber codon that is recognized by a tRNA$^{UTu}{}_{amber}$), a Grx1$_{C11S/C14S}$ (where the Cys 11 codon is replaced with a serine codon) and Grx1$_{C14S}$ (and wherein Cys 11 codon encodes Cys).

FIG. 7A shows Sec dependent glutathione disulfide oxidoreductase activity. Pure Grx1$_{C11am/C14S}$Sec, Grx1$_{C11S/C14S}$ and Grx1$_{C14S}$ were tested for disulfide oxidoreductase activity. The reduction of a mixed disulfide between β-hydroxyethyldisulfide (HED) and glutathione by Grx1 variants is coupled to NADPH consumption by glutathione reductase. Glutathione reductase reconstitutes the reduced Grx1. The reaction was followed at 340 nm at 25° C. as a function of Grx1 concentration.

Pure Grx1$_{C11am/C14S}$Sec, Grx1$_{C11S/C14S}$ and Grx1$_{C14S}$ were also tested for peroxidase activity (FIG. 7B). The reduction of tBuOOH to the corresponding alcohol and water is coupled to the consumption of NADPH by glutathione reductase to reconstitute reduced Grx1. Peroxidase activity was determined at 340 nm as a function of reduced glutathione concentration at 25° C. Accordingly, peroxidase activity was determined by monitoring NADPH consumption at 340 nm as a function of the concentration of reduced glutathione at 25° C.

Peroxidase activity of Sec containing GPx1$_{am}$ and Cys containing GPx1$_{Cys}$, that were overexpressed in *E. coli* was compared to commercially available GPx$_{hum}$ from human erythrocytes (FIG. 7C). The activity was determined by using the glutathione peroxidase cellular activity assay kit.

Experiments shown in FIGS. 7A and 7C were performed in triplicates and error bars indicate the standard error of the mean.

Accordingly, substitution of Cys11 with Sec results in a protein with enzymatic activity, and in some assays, enhanced activity, while substitution of the Cys11 with serine results in a non-functional protein.

Sec incorporation was confirmed by mass spectroscopy (FIG. 8). The presence of selenocysteine at amino acid position 11 in Grx1$_{C11am/C14S}$Sec was confirmed by mass spectroscopy. Shown is the MS/MS spectrum of the trypsin-digested Sec-containing fragment S$_9$G$_{10}$U$_{11}$P$_{12}$Y$_{13}$S$_{14}$V$_{15}$R$_{16}$. Fragments observed in the second mass spectrometric analysis of this peptide are labeled with b3, y2, y3, y4 and y5. The Sec residue of the peptide in the MS/MS experiment was first treated with DTT, and then alkylated with iodoacetamide for oxidative protection of the selenol. The unit m/z describes the mass-to-charge ratio.

FIG. 9 is a spectrogram showing the results of Fourier transform ion cyclotron resonance (FT-ICR) mass spectrometry of Grx1$_{C11S/C14S}$ calculated: 10,650 Da. found 10,651 Da.

Sec incorporation was determined spectroscopically by assaying purified Grx1$_{C11am/C14S}$ with DTNB (Ellman's reagent). Grx1$_{C11S/C14S}$ and Grx1$_{C11S/C14S}$ served as positive and negative controls respectively.

tRNA$^{UTu}{}_{amber}$ mediated Sec suppression in response to the Amber codon resulted in a mixture of Sec and Ser containing Grx1$_{C11am/C14S}$ species. From this mixture the Grx1$_{C11am/C14S}$Sec species was specifically recovered by an affinity chromatographic purification using Activated Thiol Sepharose™ 4B which selectively binds to selenol (thiol) moieties of Sec (Cys) but not to hydroxyl groups of Ser residues.

An overall of 2 mg of the Sec and Ser containing Grx1$_{C11am/C14S}$ mixture were desalted and loaded on an Activated Thiol Sepharose™ 4B gravity flow chromatography column and incubated with the resin (2 ml bed volume) for 30 min. The column was then washed with lysis buffer (50 mM sodium phosphate, 100 mM NaCl, 1 mM EDTA, pH 7.0) to remove unbound Grx1$_{C11am/C14S}$Ser protein fraction. Subsequently, immobilized Grx1$_{C11am/C14S}$Sec proteins were eluted in the presence of 50 mM reduced glutathione in phosphate buffer. Overall 1.05 mg Grx1$_{C11am/C14S}$Sec was recovered from the Activated Thiol Sepharose™ 4B. This represents 52% of the overall Grx1 protein initially subjected to the Activated Thiol Sepharose™ 4B affinity chromatography. Homogeneity of the recovered Grx1$_{C11am/C14S}$Sec was accessed by mass spectrometry.

Grx1$_{C11am/C14S}$ was recovered after affinity chromatography on Activated Thiol SEPHAROSE®. The peaks corresponded to the masses of a Grx1$_{C11am/C14S}$ glutathione adduct (11,019.38), a glutathione plus K$^+$ adduct (11,057.34) and a glutathione plus Met adduct (11,150.42). The unit m/z describes the mass-to-charge ratio.

FIGS. 11A and 11B shows SerRS kinetics for tRNA$^{Sec}$, tRNA$^{Ser}$ and tRNA$^{UTu}{}_{amber}$. Varying concentrations (1-30 μM) of tRNA$^{Ser}$, tRNA$^{Sec}$ and tRNA$^{UTu}{}_{amber}$ were incubated in the presence 30 µM L-[14C] serine, 500 nM E. coli SerRS, 5 mM ATP at 37° C. Samples were taken in the linear range of the aminoacylation reaction and analyzed by scintillation counting. Kinetic parameters were determined by Michaelis-Menten plots of the initial aminoacylation velocity versus substrate concentration. Each, tRNA$^{Sec}$, tRNA$^{Ser}$ and tRNA$^{UTu}$ amber showed similar kinetic parameters for aminoacylation with serine by SerRS. KM values were determined in the low µM-range around 5 µM and Kcat and Kcat/KM at approximately 0.015 s$^{-1}$ and 0.0025 s$^{-1}$ µM$^{-1}$, respectively (FIG. 11A). Ser-tRNA$^{UTu}{}_{amber}$ is a substrate for SelA in vitro. While Ser-tRNA$^{Sec}$ is nearly completely converted to Sec-tRNA$^{Sec}$ by SelA, 50% conversion to Sec-tRNA$^{UTu}{}_{amber}$ is observed over a course of 20 minutes (FIG. 11B)

FIG. 12 shows in vitro conversion of tRNA$^{Sec}$ and tRNA$^{UTu}{}_{amber}$ by SelA. 5 µM SelD, 1 mM Na$_2$SeO$_3$ and 5 mM ATP were pre-incubated at pH 7.2 under anaerobic conditions at 37° C. for 30 min and then supplemented by 1 µM SelA and 10 µM of [α$^{32}$-P] radiolabeled Ser-tRNA$^{Sec}$ and Ser-tRNA$^{UTu}$ for up to 20 min. 1.54, aliquots taken at different time points were digested with Nuclease P1 and spotted onto cellulose thin layer chromatography plates After development the plates were analyzed by autoradiography. While Ser-tRNA$^{Sec}$ is nearly completely converted only approximately 50% of Sec-tRNA$^{UTu}$ is formed by SelA over a course of 20 min.

TABLE 1

Kinetic Parameters of tRNA$^{Sec}$ and tRNA$^{UTu}$

| tRNA | K$_M$ [µM] | K$_{cat}$ [s$^{-1}$] | K$_{cat}$/K$_M$ |
|---|---|---|---|
| E. coli tRNA$^{Sec}$ | 4.1 ± 1.0 | 0.02 | 0.005 |
| E. coli tRNA$^{Ser}$ | 5.7 ± 1.4 | 0.01 | 0.002 |
| tRNA$^{UTu}{}_{am}$ | 5.1 ± 1.1 | 0.012 | 0.0023 |

FIG. 13 shows in vitro conversion of tRNA$^{Sec}$ and tRNA$^{UTu}{}_{amber}$ by PSTK. 10 µM of [α32-P] radiolabeled Ser-tRNA$^{Sec}$ and Ser-tRNA$^{UTu}$ were incubated at pH 7.2 in the presence of 5 µM Methanococcus maripaludis PSTK and 5 mM ATP under anaerobic conditions at 37° C. for up to 25 min. 1.5 µL aliquots taken at different time points were digested with Nuclease P1 and spotted onto cellulose thin layer chromatography plates. After development the plates were analyzed by autoradiography. Approximately 40% of both, Ser-tRNA$^{Sec}$ and Ser-tRNA$^{UTu}$ are converted to phosphoseryl-(Sep-)tRNA by PSTK over a course of 25 min.

Example 7: Sec Complements MGMT Active Site Residue Cys145

O-6-methylguanine-DNA methyltransferase (MGMT) is an enzyme that can protect the alkyltransferase-deficient E. coli Δada, Δogt-1 strain from the DNA methylating agent N-methyl-N'-nitro-N-nitrosoguanidine (Christians, et al., PNAS, 93:6124-6128 (1996)). MGMT is capable of transferring the methyl group from DNA with O6-methylguanine to the wild-type Cys145 and designed Sec145, but not to Ser145 at the active site in a single turn over reaction. E. coli Dada Dotg-1 cells expressing either (MGMT) Cys145, amber145 (Sec/Ser) or Ser145 mutant proteins transformed with tRNA$^{UTu}{}_{amber}$ were pulsed 3x with N-Methyl-N-nitroso-N'-nitroguanidine. Dilutions of the cell cultures were plated to indicate cellular protection through active MGMT as shown by growth.

FIG. 13 shows amber145 rescues MGMT enzyme activity while Ser145 is inactive, relative to a Cys145 control.

Example 8: Genetic Optimization Increases tRNA$^{UTu}$ Mediated Sec Incorporation tRNA$^{UTu}$ mediated Sec incorporation into Grx1$_{C11am/C14S}$ was gradually increased by genetic optimization of the expression system. Initially Grx1 was expressed under the control of an IPTG inducible T7 promoter. The change from genomically encoded SelA to inducible recombinant SelA increased the Sec incorporation ratio from 23% to 37%.

A further increase to 49% was obtained by adding T7 controlled Methanococcus janaschii PSTK that was codon optimized for the E. coli expression host. By adding a second selA copy Sec insertion increased to 59% while up to 70% incorporation were obtained after the Grx1 reporter was expressed independently from SelA and PSTK under the control of an arabinose inducible PBAD promoter (FIG. 14).

Example 9: Development of Variants of tRNA$^{UTu}$

Materials and Methods
Molecular Cloning

Variants of tRNA$^{UTu}$ (SEQ ID NO:7), including variant tRNA$^{UTuX}$ (SEQ ID NO:59), were generated using quikchange site-directed mutagenesis. E. coli fdhF$_{140am}$ was cloned into the PURExpress DHFR control vector provided by NEB in place of DHFR, as described according to manufacturer.

tRNA Template Production

The tRNA$^{UTu}$ variants were generated by site directed mutagenesis using the plasmids puc18-[tRNA$^{UTu}{}_{am}$] and pGFIB-[tRNA$^{UTu}{}_{am}$] as templates (Aldag, et al., Angew. Chem. Int. Ed. Engl., 52, 1441-5 (2013)). The resulting constructs were denoted puc18-[tRNA$^{UTuX}{}_{am}$] and pGFI-[tRNA$^{UTuX}{}_{am}$]. Next, tRNA$^{Sec}$, tRNA$^{UTu}$ and tRNA$^{UTuX}$ variants were then transcribed and folded as described earlier (Aldag, et al., Angew. Chem. Int. Ed. Engl., 52, 1441-5 (2013)). For cell free protein synthesis, tRNA$^{Sec}$, tRNA$^{UTu}$, tRNA$^{UTuX}$, and tRNA$^{SecUX}$ DNA was amplified using PCR for subsequent in vitro transcription.

In Vitro Transcription

To prepare the plasmid DNA template for tRNA transcription, 100 µg of the maxi-prepped plasmid was digested with the restriction endonuclease BstNI in a 1 mL reaction at 60° C. for 4 h. Afterwards, the DNA was extracted by addition of 1 volume phenol/chloroform/isoamyalcohol (25:24:1) and precipitated by mixing with ⅒ volume sodium acetate (3 M, pH 5.2) and 2.5 volumes ethanol (100%). Samples were incubated −80° C. and centrifuged to precipitate DNA. Sedimented DNA was washed once with ethanol (70%) and resuspended in 45 µL of water. 60 µg of the linearized pUC18-tRNA$^{UTu}$ constructs were subjected to a 1 mL transcription reaction containing 4 mM each of the ribonucleotides rATP, rUTP, rGTP and rCTP, 10 µM T7 RNA polymerase, 40 mM Tris/HCl pH 7.7, 22 mM MgCl$_2$, 2 mM spermidine, 25 mM DTT, 50 µg BSA and 25 µg inorganic pyrophosphates (Sigma Aldrich). Transcription reactions were carried out at 37° C. for 6 h and precipitated with ⅒ volume sodium acetate (3M, pH 5.2) and 2.5 volume ethanol (100%), subsequently. After sedimentation, the transcribed tRNA was dissolved in water and purified on a 12% acrylamide/8 M urea denaturing gel. After acidic extraction from the gel with 1 M sodium acetate pH 5.2 and precipitation with 2.5 volumes ethanol (100%), pure tRNA was stored at −80° C.

Results

Miller, et al., "A synthetic tRNA for EF-Tu mediated selenocysteine incorporation in vivo and in vitro," *FEBS Letters*, (589)2194-2199 (2015), as well as its supplemental information including, but not limited to, data, figures, tables, and text, are specifically incorporated by reference herein in their entries.

As introduced above, organisms pay a high fitness cost for the benefit of endowing proteins with the unique properties of the 21st amino acid, selenocysteine (Sec) (Arner, *Exp. Cell Res.*, 316:1296-1303 (2010); Beld, et al., *Biochemistry*, 46:5382-5390 (2007)), and have evolved complex biosynthetic and translational mechanisms to incorporate Sec (Böck, et al., *Landes Bioscience*, 320-327 (2005); Yoshizawa, et al., *Biochim. Biophys. Acta*, 1790:1404-1414 (2009)). At the interface of Sec synthesis and insertion lies tRNA$^{Sec}$. Initially acylated by seryl-tRNA synthetase (SerRS) to form Ser-tRNASec, the bacterial enzyme SelA catalyzes the conversion of Ser to Sec in a single step on the tRNA (Böck, et al., *Landes Bioscience*, 320-327 (2005)). Once synthesized, selenocysteinyl-tRNA (Sec-tRNA$^{Sec}$) is bound by the specialized Sec-specific elongation factor SelB, which subsequently binds to a highly conserved mRNA motif denoted as Selenocysteine Insertion Sequence (SECIS), facilitating insertion of Sec at a UGA codon (Böck, et al., *Landes Bioscience*, 320-327 (2005)). In bacteria, the SECIS sequence is located directly after the suppressed UGA and is thus part of the coding sequence of bacterial genes, making engineering of newly designed selenoproteins very difficult (Aldag, et al., *Proc. Natl. Acad. Sci. U.S.A.*, 106:5481-5486 (2009); Arner, et al., *Methods Enzymol.*, 347:226-235 (2002); Xu, et al., *Nucleic Acids Res.*, 41:9800-9811 (2013)).

The Examples above highlight construction of synthetic tRNAs including tRNA$^{UTu}$, that enabled SECIS-independent and EF-Tu-dependent insertion of Sec in *Escherichia coli* (Aldag, et al., *Angew. Chem. Int. Ed. Engl.*, 52:1441-1445 (2013)). tRNA$^{UTu}$ combines the aminoacyl acceptor helix of tRNA$^{Sec}$ with the backbone of tRNA$^{Ser}$, and serves as a substrate for the essential proteins SerRS, SelA, and EF-Tu. By virtue of its interaction with EF-Tu, Sec-tRNA$^{UTu}$ circumvents the need for the Sec-specific elongation factor SelB, and more importantly does not require the SECIS mRNA motif. Sec-tRNA$^{UTu}$ therefore participates in canonical translation, allowing versatile sequence-independent production of designed selenoproteins programmed by UAG.

While SelB recognizes only Sec-tRNA$^{Sec}$ (Paleskava, et al., *J. Biol. Chem.*, 285:3014-3020 (2010); Bröcker, et al., *Angew. Chem. Int. Ed. Engl.*, 53:319-323 (2014)), EF-Tu serves all other aminoacyl-tRNAs (aa-tRNAs). Therefore, if the SelA-dependent conversion of Ser-tRNAU$^{Tu}$ to Sec-tRNAUTu is not complete, Ser will be incorporated instead of the desired Sec residue. This was an impediment in the earlier work in which ~30% misincorporation of Ser was observed (Aldag, et al., *Angew. Chem. Int. Ed. Engl.*, 52:1441-1445 (2013)). A strategy was developed to engineer an improved tRNA$^{UTu}$ with better substrate properties for SelA, misincorporation could be prevented.

The co-crystal structure of decameric *Aquifex aeolicus* SelA protein in complex with ten *Thermus tengcongensis* tRNASec molecules provided molecular insight into the enzyme's substrate recognition and coordination, illustrating the mechanism by which SelA discriminates between tRNA$^{Ser}$ and tRNA$^{Sec}$ (Itoh, et al., *Science*, 340:75-78 (2013)). This information was used to rationally engineer additional tRNA$^{UTu}$ variants to act as ideal substrates for SelA that would increase the yield of Sec conversion and finally insertion. Using site-directed mutagenesis, the sequence of the original tRNA$^{UTu}$ (SEQ ID NO:7) was incrementally changed to more closely resemble the features of tRNA$^{Sec}$ that contribute to binding of SelA. These modifications included both single and combined exchanges as well as insertions and deletions of nucleotides in various regions of the tRNA. However, they left the important tRNA$^{UTu}$ features that (i) provide thermodynamic binding specificity for EF-Tu (Schrader, et al., *J. Mol. Biol.*, 386: 1255-1264 (2009)) and (ii) contribute to the incompatibility between tRNA$^{Sec}$ and EF-Tu (Rudinger, et al., *EMBO J.*, 15:650-657 (1996)) (FIG. 15A). Twenty-nine tRNA were produced. Exemplary variants are provided below (SEQ ID NO:59-67 and 86-92). The position(s) of modifications relative to SEQ ID NO:7 are bolded and underlined. The amber anti-codon is in italics. tRNA positional markers (e.g., 1, 5, 5a, 10, 20, 30, 40, 50, 60, 67a, 70) are provided in superscript and are not part of the tRNA sequence.

UTu
G$^1$GAAG$^5$A$^{5a}$UGUGG$^{10}$CCGAGCGGU$^{20}$UGAAGGCACCGG$^{30}$UCU*CUA*AAAC$^{40}$

CGGCGACCCGAAAGGGUUCCA$^{50}$GAGUUCGAAU$^{60}$CUCUGCAU$^{67a}$CUU$^{70}$CC

GCCA (SEQ ID NO: 7; E. coli scaffold, tRNA$^{UTu}$-amber)

UTuX
G$^1$GAAG$^5$A$^{5a}$UGGUG$^{10}$CCGUCCGGU$^{20}$GAAGGCGCCGG$^{30}$UCU*CUA*AAAC$^{40}$

CGGUCGACCCGAAAGGGUUCGCA$^{50}$GGGUUCGACU$^{60}$CCCUGCAU$^{67a}$CUU$^{70}$

CCGCCA (SEQ ID NO: 59); E. coli scaffold, tRNA$^{UTuX}$-amber)

Variant A
G$^1$GAAG$^5$A$^{5a}$UGGUG$^{10}$CCGAGCGGU$^{20}$UGAAGGCGCCGG$^{30}$UCU*CUA*AA AC$^{40}$CGGCGACCCGAAAGGGUUCCA$^{50}$GAGUUCGAAU$^{60}$CUCUGCAU$^{67a}$CU U$^{70}$CCGCCA (SEQ ID NO: 60; E. coli scaffold, tRNA$^{variant\ A}$-amber)

Variant B
G$^1$GAAG$^5$A$^{5a}$UGGUG$^{10}$CCGUCCGGU$^{20}$GAAGGCGCCGG$^{30}$UCU*CUA*AAAC$^{40}$ CGGCGACCCGAAAGGGUUCCA$^{50}$GAGUUCGAAU$^{60}$CUCUGCAU$^{67a}$CUU$^{70}$CC GCCA (SEQ ID NO: 86; E. coli scaffold, tRNA$^{variant\ B}$-amber)

Variant C
G$^1$GAAG$^5$A$^{5a}$UGUG$^{10}$GCCGAGCGGU$^{20}$UGAAGGCGCCGG$^{30}$UCU*CUA*AA AC$^{40}$CGGUCGACCCGAAAGGGUUCGCA$^{50}$GAGUUCGAAU$^{60}$CUCUGCAU$^{67a}$ CUU$^{70}$CCGCCA (SEQ ID NO: 87; E. coli scaffold, tRNA$^{variant\ C}$-amber)

-continued

Variant D
G$^1$GAAG$^5$A$^{5a}$UGUG$^{10}$GCCGAGCGGU$^{20}$UGAAGGCGCCGG$^{30}$UCUCUAAA

AC$^{40}$CGGUUCGACCCGAAAGGGUUCGGCA$^{50}$GAGUUCGAAU$^{60}$CUCUGCA

U$^{67a}$CUU$^{70}$CCGCCA (SEQ ID NO: 88; E. coli scaffold, tRNA$^{variant\ D}$-amber)

Variant E
G$^1$GAAG$^5$A$^{5a}$UGUG$^{10}$GCCGAGCGGU$^{20}$UGAAGGCGCCGG$^{30}$UCUCUAAA AC$^{40}$CGGCGACCCGAAAGGGUUCCA$^{50}$GGGUUCGACU$^{60}$CCCUGCAU$^{67a}$CU U$^{70}$CCGCCA (SEQ ID NO: 61; E. coli scaffold, tRNA$^{variant\ E}$-amber)

Variant F
G$^1$GAAG$^5$A$^{5a}$UGGUG$^{10}$CUCGAGCGGU$^{20}$UGAAGGGCGCCGG$^{30}$UCUCUAAA AC$^{40}$CGGCGACCCGAAAGGGUUCCA$^{50}$GAGUUCGAAU$^{60}$CUCUGCAU$^{67a}$CU U$^{70}$CCGCCA (SEQ ID NO: 89; E. coli scaffold, tRNA$^{variant\ F}$-amber)

Variant G
G$^1$GAAG$^5$A$^{5a}$UGGUG$^{10}$CCGUGCGGU$^{20}$UGAAGGCGCCGG$^{30}$UCUCUAAA AC$^{40}$CGGCGACCCGAAAGGGUUCCA$^{50}$GAGUUCGAAU$^{60}$CUCUGCAU$^{67a}$CU U$^{70}$CCGCCA (SEQ ID NO: 90; E. coli scaffold, tRNA$^{variant\ G}$-amber)

Variant H
G$^1$GAAG$^5$A$^{5a}$UGGUG$^{10}$CCGUCCGGU$^{20}$GAAGGCGCCGG$^{30}$UCUCUAAAAC$^{40}$ CGGCGACCCGAAAGGGUUCCA$^{50}$GGGUUCGACU$^{60}$CCCUGCAU$^{67a}$CUU$^{70}$CC GCCA (SEQ ID NO: 62; E. coli scaffold, tRNA$^{variant\ H}$-amber)

Variant I
G$^1$GAAG$^5$A$^{5a}$UGGUG$^{10}$CCGUCCGGU$^{20}$GAAGGCGCCGG$^{30}$UCUCUAAAAC$^{40}$ GCGUUCGACCCGAAAGGGUUCGGCA$^{50}$GGGUUCGACU$^{60}$CCCUGCAU$^{67a}$CU U$^{70}$CCGCCA (SEQ ID NO: 63; E. coli scaffold, tRNA$^{variant\ I}$-amber)

Variant J
G$^1$GAAG$^5$A$^{5a}$UGUG$^{10}$GCCGAGCGGU$^{20}$UGAAGGCGCCGG$^{30}$UCUCUAAA AC$^{40}$CGGCGACCCGAAAGGGUUCCA$^{50}$GGGUUCGAUU$^{60}$CCCUGCAU$^{67a}$CU U$^{70}$CCGCCA (SEQ ID NO: 64; E. coli scaffold, tRNA$^{variant\ J}$-amber)

Variant K
G$^1$GAAG$^5$A$^{5a}$UGGUG$^{10}$CUGCGAGCGGU$^{20}$UGAAGCGGCGCCGG$^{30}$UCUCUA

AAAC$^{40}$CGGCGACCCGAAAGGGUUCCA$^{50}$GAGUUCGAAU$^{60}$CUCUGCAU$^{67a}$

CUU$^{70}$CCGCCA (SEQ ID NO: 91; E. coli scaffold, tRNA$^{variant\ K}$-amber)

Variant L
G$^1$GAAG$^5$A$^{5a}$UGGUG$^{10}$CCGUCCGGU$^{20}$UGAAGGCGCCGG$^{30}$UCUCUAAA AC$^{40}$CGGCGACCCGAAAGGGUUCCA$^{50}$GAGUUCGAAU$^{60}$CUCUGCAU$^{67a}$CU U$^{70}$CCGCCA (SEQ ID NO: 65; E. coli scaffold, tRNA$^{variant\ L}$-amber)

Variant M
G$^1$GAAG$^5$A$^{5a}$UGGUG$^{10}$CCGUCCGGU$^{20}$GAAGGCGCCGG$^{30}$UCUCUAAAAC$^{40}$ CGGCGACCCGAAAGGGUUCCA$^{50}$GGGUUCGAUU$^{60}$CCCUGCAU$^{67a}$CUU$^{70}$C CGCCA (SEQ ID NO: 66; E. coli scaffold, tRNA$^{variant\ M}$-amber)

Variant N
G$^1$GAAG$^5$A$^{5a}$UGGUG$^{10}$CCGUCCGGU$^{20}$GAAGGCGCCGG$^{30}$UCUCUAAAAC$^{40}$ CGGUCGACCCGAAAGGGUUCGCA$^{50}$GGGUUCGAUU$^{60}$CCCUGCAU$^{67a}$CUU$^{70}$ CCGCCA (SEQ ID NO: 67; E. coli scaffold, tRNA$^{variant\ N}$-amber)

Variant O
G$^1$GAAG$^5$A$^{5a}$UGGUG$^{10}$CCGUCCGGU$^{20}$GAAGGCGCCGG$^{30}$UCUCUAAAAC$^{40}$ CGGUUCGACCCGAAAGGGUUCGGCA$^{50}$GGGUUCGAUU$^{60}$CCCUGCAU$^{67a}$CU U$^{70}$CCGCCA (SEQ ID NO: 92; E. coli scaffold, tRNA$^{variant\ O}$-amber)

Example 10: Variants of tRNA$^{UTu}$ can Mediate Sec Insertion

Materials and Methods

In Vivo tRNA$^{UTu}$ Utilization Assay

E. coli DselA DselB DfdhF strain MH5 was co-transformed with plasmids pACYC-[E. coli selA+, M. jannaschii pstk] and pGFIB-[tRNA$^{UTu}_{am}$], or pGFIB-[tRNAU$^{TuX}_{am}$] variants as well as pRSF-[E. coli serS-fdhF$_{140am}$] and grown on LB medium supplemented with the corresponding antibiotics ampicillin, chloramphenicol, or kanamycin. As a control E. coli MH5 was co-transformed with the plasmids pACYC-[E. coli selA+, M. jannaschii pstk], pRSF-[E. coli serS-fdhF$_{1400p}$] and pET15b-[E. coli selB] to reconstitute the wild-type (WT) Sec formation apparatus using the genomically encoded tRNA$^{Sec}$. E. coli MH5 carrying plasmids pACYC-[E. coli selA+M. jannaschii pstk], pRSF-[E. coli serS-fdhF$_{140am}$] and pET15b-[E. coli selB] served as a second control. Overnight cultures of these clones were plated on LB agar plates supplemented with 10 lM IPTG, 1 lM Na2MoO4, 1 lM Na2SeO3 and 50 mM sodium formate, as previously described (Yuan, et al, Proc. Natl. Acad. Sci. U.S.A., 103:18923-18927 (2006); Araiso, et al., Nucleic Acids Res., 36:1187-1199 (2008)), and were grown anaerobically at 37° C. overnight. Plates were then overlaid with a top agar containing 1 mg/mL benzyl viologen (BV), 250 mM sodium formate, and 25 mM KH2PO4 pH 7.0. The appearance of a purple color indicated catalytically active FDHH, which depends on Sec insertion at position 140.

Results

The 29 tRNA variants were tested for their capability to mediate Sec insertion, using E. coli FDH$_H$ as a reporter protein (FIG. 16A-16Q). A natural selenoenzyme, FDH$_H$ contains an essential Sec residue at position 140, and catalyzes the electron transfer from formate onto the artificial electron acceptor benzyl viologen under anaerobic conditions. FDH$_H$-mediated BV reduction was used as a sensitive colorimetric in vivo reporter system for functional Sec insertion, as reduced BV adopts a dark purple color (Lacourciere, et al., Proc. Natl. Acad. Sci. USA., 99:9150-9153 (2002)) (FIG. 15B). Consequently, the E. coli ΔselA ΔselB ΔfdhF triple deletion strain MH5 was complemented with a vector encoding SelA, PSTK, FDH$_{H140am}$ and each tRNA$^{UTu}{}_{am}$ variant, subsequently grown in the presence of formate and BV (Aldag, et al., *Angew. Chem. Int. Ed. Engl.*, 52:1441-1445 (2013)). To serve as a positive control, FDH$_{H140op}$ expressed with the genomic WT tRNA$^{Sec}{}_{op}$ was also grown in the presence of SelB (FIG. 15B).

Using this cell based assay, a tRNA variant capable of producing active FDH$_H$ with the same apparent BV reduction activity as the WT was identified from among the 29 tRNA$^{UTu}$ variants (FIGS. 15B and 16A-16Q), notably producing visibly more reduced BV than the original synthetic variant. This improved tRNA was named tRNA$^{UTuX}{}_{am}$; it differs from the original tRNA$^{UTu}$ in 11 positions (FIGS. 15A, 16A-16Q).

Variants E, H, J, and L also exhibited strong BV reduction activity, and variants A, I, M, and N exhibited moderate BV reduction activity, in this assay. Variants B, C, D, F, G, K, and O, and the other 13 variants tested appeared to be inactive in this assay.

Example 11: tRNA$^{UTuX}$ Exhibits Improved Properties In Vitro

Materials and Methods

Purification of *E. coli* SelA, SelB, SelD, SerRS, and EF-Tu

*E. coli* SelA, SelB, SelD, SerRS, and EF-Tu were expressed in *E. coli* BL21 cells as N-terminal 6×His tag fusion proteins using constructs encoded in the pCA24N vector from the ASKA GFP-minus strain collection. Cells were overexpressed and purified using Ni-NTA gravity flow columns, as previously reported (Aldag, et al., *Angew. Chem. Int. Ed. Engl.*, 52, 1441-5 (2013)). Purified SelA, SelD, SerRS, and EF-Tu were dialyzed against storage buffer (100 mM HEPES pH 7.5, 200 mM KCl, 10 mM MgCl$_2$, 1 mM DTT, 15% glycerol) and concentrated by Amicon Ultra filter (Millipore) for storage at −80° C. SelB was eluted from Ni-NTA resin with SelB Buffer (100 mM KH$_2$PO$_4$, 2 mM DTT, 1M sorbitol, 200 mM arginine, 12% glycerol, 200 mM imidazole, pH 7.2), concentrated as described above, and stored at −80° C.

Folding, Radiolabelling and Aminoacylation of tRNA

In vitro transcribed tRNA variants were refolded by slow-cooling 300 μL of tRNA from 85° C. to 50° C., and were then chilled on ice for 15 minutes.

To radiolabel samples, 100 μl folded tRNA was incubated with sodium phosphate (7 μM), *E. coli* CCA-adding enzyme (5 U), and an excess of [α$^{32}$P]ATP (~50 μCi for 350 μl reaction). Samples were incubated at room temperature in a shielded box for one hour, thereby enzymatically exchanging 3′-terminal AMP with [$^{32}$P]AMP (Oshikane, et al., *Science*, 312, 1950-4 (2006)).

Following radiolabeling, samples were purified by acidic phenol-chloroform (pH ~4) extraction and ethanol precipitation. Folded and radiolabeled tRNA samples were stored at −80° C.

Selenocysteinylation of radiolabeled tRNA was conducted by incubating 10 μl of 25 μM tRNA samples with SelA (1 μg/ml), SerRS (1 μg/ml), SelD (2 μg/ml), inorganic pyrophosphatase (1 U), sodium selenite (80 μM), HEPES buffer (5 mM, pH 7.5), magnesium chloride (700 μM), NH$_4$Cl (7 mM), potassium chloride (3 mM), GTP (2 mM), ATP (5 mM), L-serine (2 mM), and DTT (200 μM) in a total reaction volume of 300 μl. Reactions were conducted at 37° C. under anaerobic conditions.

Following selenocysteinylation reaction, samples were purified by acidic phenol-chloroform (pH ~4) extraction and ethanol precipitation, and stored in sealed vials at −80° C. Selenocysteinylation was confirmed by thin-layer chromatography of nuclease P1 digests.

Serylation Kinetics

To determine the kinetic parameters of tRNA serylation by *E. coli* SerRS, 0.1-10 μM of tRNA were incubated in the presence of 30 μM [14C] radiolabeled L-serine (Sigma), 5 mM ATP and SerRS (5 nM-10 μM) in SerRS buffer (100 mM Hepes pH 7.0, 10 mM KCl, 10 mM Mg-acetate, 1 mM DTT and 1 mg/mL BSA). Reactions were carried out in 50 μL volume at 37° C. Samples of 9 μl were taken after different time points and quenched by spotting on filter paper discs (3 mm, Whatman) that had prior soaking in 45 μL of 5% trichloric acid (TCA). Aminoacyl-tRNA was assayed by quantification of the [$^{14}$C] radio signal in a scintillation counter (S6500 Scintillation Counter, Beckman Coulter) (Aldag, et al., *Angew. Chem. Int Ed. Engl.*, 52, 1441-5 (2013)). The kinetic parameters were determined by Michaelis-Menten plots of the initial aminoacylation velocity versus substrate concentration.

In Vitro Sec-tRNA Formation

To characterize in vitro formation of Sec-tRNA, tRNA species were radiolabeled using [a-$^{32}$P]ATP and the *E. coli* CCA editing enzyme [Sherrer, et al., *Nucleic Acids Res.*, 36:1871-1880 (2008)]. Ser-tRNA formation by SerRS, selenophosphate production by SelD, and Ser to Sec conversion by SelA was carried out under anoxic conditions as previously described (Aldag, et al., *Angew. Chem. Int. Ed. Engl.*, 52:1441-1445 (2013)). Conversion rates were determined by autoradiography and by quantitation of aminoacyl-AMP after thin layer chromatography of nuclease P1 digests of aminoacyl-tRNA$^{UTu}$ (Sheppard, et al., *Methods*, 44:139-145 (2008)). For use in cell free protein synthesis experiments, Sec-tRNA was phenol-chloroform extracted, ethanol precipitated, and resuspended in RNase free H2O to desired concentration.

Ser-tRNA Hydrolysis Protection by SelA

Hydrolysis protection assays of Ser-tRNA species by SelA were conducted in a manner analogous to previously described protection of Sep-tRNA by EF-Tu (Park, et al., *Science*, 333, 1151-4 (2011)). Briefly, serylated and [α$^{32}$P]-labeled tRNA$^{Sec}$, tRNA$^{UTu}$ and tRNA$^{UTuX}$ (10 μM) were incubated with SelA (50 μM) for 10 min at room temperature. Following the addition of nuclease P1, 1.5 μl aliquots were taken at different time points between 0-25 min. Degradation was evaluated using thin-layer chromatography analyzed by autoradiography. Controls reactions were carried out in the absence of SelA.

Results

To validate the observed BV color formation, tRNA$^{UTuX}{}_{am}$ was then characterized in a set of in vitro experiments. While the modifications introduced in tRNA$^{UTuX}$ focused on better interaction with SelA, it was a prerequisite to retain robust Ser-tRNA$^{UTuX}$ formation by SerRS. Serylation assays of tRNA$^{UTuX}$, tRNA$^{Sec}$, and the original tRNA$^{UTu}$ did not reveal any significant differences among the three tRNA species (Table 2), as the K$_M$ (3.51M), k$_{cat}$ (0.42 min$^{-1}$), and k$_{cat}$/K$_M$ (0.12 μM$^{-1}$ min$^{-1}$) of tRNA$^{UTuX}$ were found to be very close to those of tRNA$^{Sec}$ and tRNA$^{UTu}$.

TABLE 2

SerRS kinetics for tRNA$^{Sec}$, tRNA$^{UTu}$ and tRNA$^{UTuX}$

| tRNA | $K_m$ [μM] | $k_{cat}$ [min$^{-1}$] | $K_{cat}/K_m$ [μM$^{-1}$ min$^{-1}$] |
|---|---|---|---|
| tRNA$^{Sec}$ | 11.1 ± 2.2 | 0.33 | 0.029 ± 0.006 |
| tRNA$^{UTu}$ | 2.0 ± 0.2 | 0.39 | 0.20 ± 0.02 |
| tRNA$^{UTuX}$ | 3.5 ± 0.5 | 0.42 | 0.12 ± 0.02 |

Varying concentrations (1-30 μM) of E. coli tRNA$^{Sec}$, tRNA$^{UTu}$ and tRNA$^{UTuX}$ were incubated in the presence 30 μM L-[14C] serine, 500 nM E. coli SerRS, and 5 mM ATP at 37° C. Samples were taken in the linear range of the aminoacylation reaction and analyzed by scintillation counting. Kinetic parameters were determined by Michaelis-Menten plots of the initial aminoacylation velocity versus substrate concentration.

Subsequently, conversion of Ser-tRNA$^{UTuX}$ to Sec-tRNA by SelA was examined (FIG. 15C). In contrast to the original tRNA$^{UTu}$, which showed about ~50% SelA-dependent conversion to Sec-tRNA, Ser-tRNA$^{UTuX}$ and WT Ser-tRNA$^{Sec}$ were very similar and yielded ~90% Sec formation (after 20 min). Tighter binding of Ser-tRNA$^{UTuX}$ to SelA was further confirmed by RNase protection in the presence of excess SelA protein, revealing that within 20 min twice the amount of Ser-tRNA$^{UTu}$ was digested by nuclease P1 than Ser-tRNA$^{UTuX}$ or Ser-tRNA$^{Sec}$ (FIG. 17). Nuclease protection of Ser-tRNA variants by SelA. Ser-tRNA$^{Sec}$, Ser-tRNA$^{UTu}$ and Ser-tRNA$^{UTuX}$ samples were incubated with an excess SelA for 10 minutes, followed by addition of nuclease P1. Digestion of each tRNA sample was monitored over time using thin layer chromatography (TLC) followed by autoradiography. While ~25% of Ser-tRNA$^{UTu}$ was hydrolyzed after 25 min, as indicated by the occurrence of Ser-AMP tRNA$^{UTu}$ spots, less than 15% of Ser-tRNA$^{Sec}$ and Ser-tRNA$^{UTuX}$ were digested. Controls were carried out in the absence of SelA, which uniformly resulted in ~80% of the Ser-tRNA species being hydrolyzed by nuclease P1 after 25 min.

While the modifications introduced in tRNA$^{UTuX}$ focused on better interaction with SelA, it was a prerequisite to retain robust Ser-tRNA$^{UTuX}$ formation by SerRS. Serylation assays of tRNA$^{UTuX}$, tRNA$^{Sec}$, and the original tRNA$^{UTu}$ did not reveal any significant differences among the three tRNA species (Table 2), as the $K_M$ (3.5 lM), $k_{cat}$ (0.42 min$^{-1}$), and $k_{cat}/K_M$ (0.12 μM$^{-1}$ min$^{-1}$) of tRNA$^{UTuX}$ were found to be very close to those of tRNA$^{Sec}$ and tRNA$^{UTu}$. Subsequently, conversion of Ser-tRNA$^{UTuX}$ to Sec-tRNA by SelA was examined (FIG. 15C). In contrast to the original tRNA$^{UTu}$, which showed about ~50% SelA-dependent conversion to Sec-tRNA, Ser-tRNAUTuX and WT Ser-tRNASec were very similar and yielded ~90% Sec formation (after 20 min). Tighter binding of Ser-tRNA$^{UTuX}$ to SelA was further confirmed by RNase protection in the presence of excess SelA protein, revealing that within 20 min twice the amount of Ser-tRNA$^{UTu}$ was digested by nuclease P1 than Ser-tRNA$^{UTuX}$ or Ser-tRNA$^{Sec}$ (FIG. 17).

Example 12: tRNA$^{UTuX}$ Exhibits Improved Selenoprotein Synthesis

Materials and Methods

FDH$_H$ and Grx1 Activity Measurements

FDH$_H$ was purified and specific activity was measured using benzyl viologen (BV) reduction as previously described (Aldag, et al., Angew. Chem. Int. Ed. Engl., 52, 1441-5 (2013), Bröcker, et al., Angew. Chem. Int. Ed. Engl., 53, 319-23 (2014)). Grx1 was purified and DTNB binding was measured colorimetrically as previously described (Aldag, et al., Angew. Chem. Int. Ed. Engl., 52, 1441-5 (2013)).

SecUx
(SEQ ID NO: 93)
GGAAGAUGGUCGUCUCCGGUGAGGCGGCUGGACUCUAAAUCCA

GUUGGGGCCGCCAGCGGUCCCGGUCAGGUUCGACUCCUUGCAUC

UUCCGCCA

Cell-Free Selenoprotein Synthesis

Cell-free in vitro translation experiments were conducted using the PURExpress in vitro Protein Synthesis Kit (E6800S) or PURExpress DRF123 kit (E6850S, New England Biolabs Inc.), as noted. Reactions were prepared according to the manufacturer's instructions inside an anaerobic chamber, and were supplemented with 1 lM sodium molybdate, 40 U RNasin Plus RNase Inhibitor (Promega), and 250 ng of fdhF mutants at position 140 cloned into PURE vector. Reactions were normalized against expressed dihydrofolate reductase (DHFR) as a negative control, a protein that did not exhibit measurable reduction of BV. For translation mediated by tRNA$^{Sec}_{am}$, tRNA$^{Sec}_{op}$, tRNA$^{Sec}_{CGU}$, tRNA$^{Sec}_{GCC}$, tRNA$^{Sec}_{CCU}$, and tRNA$^{Sec}_{UCG}$, PURExpress kit reactions were supplemented with 12 lM Sec-tRNA$^{Sec}_{am}$, 12 lM SelB, and were allowed to proceed for two hr at 37° C. For expression mediated by tRNA$^{UTu}_{am}$ (SEQ ID NO:7), tRNA$^{UTuX}_{am}$ (SEQ ID NO:59), or tRNA$^{SecUX}_{am}$ (SEQ ID NO:93), PURExpressDRF 123 kit reactions were prepared in the absence of RF1, supplemented with 70 lM Sec-tRNA, 67 lM EF-Tu, and were allowed to proceed for five hr at 37° C. Plasmid containing fdhF with corresponding cognate codon at position 140 was also added to each reaction. Following protein synthesis, 0.7 mg/mL BV and 7 mM sodium formate were added to the reaction mixture to a final volume of 30 lL. FDH$_H$ activity was monitored over time via absorbance at 578 nm measuring using a Nanodrop 2000 (Thermo-Scientific Nano-Drop 2000 UV-vis Spectrophotometer). As a negative control, a reaction was prepared with 12 lM Ser-tRNA$^{Sec}_{am}$ instead of Sec-tRNA$^{Sec}_{am}$; absence of BV reduction activity was confirmed following this reaction.

Results

To determine the yield of Sec insertion by tRNA$^{UTuX}$ the specific activity of purified FDH$_H$ following expression in vivo was measured. Using FDH$_{H140op}$ produced by WT tRNA$^{Sec}$ as a standard, the specific activity of FDH$_{H140am}$ synthesized in the presence of either tRNA$^{UTuX}_{am}$ or tRNA$^{UTu}_{am}$ was measured for comparison. FDH$_H$ made with tRNA$^{UTu}_{am}$ had ~70% of the specific activity of the enzyme made with WT tRNA$^{Sec}$, and tRNA$^{UTuX}_{am}$ produced an enzyme with activity equivalent to the WT (FIG. 18A). More specifically, Compared to WT tRNA$^{Sec}_{op}$, synthetic variants tRNA$^{UTuX}$ and tRNA$^{UTu}$ mediated Sec insertion into FDH$_{H140am}$ allowed 98.5±15.8% and 71.1±17.0% BV reduction activity, respectively.

A similar analysis was then performed using the small E. coli redox protein glutaredoxin, Grx1, which contains two Cys residues (positions 11 and 14). These residues were mutated to amber11/Ser14 and Cys11/Ser14 to generate Grx1 variants containing a single Cys or Sec residue at position 11 (Aldag, et al., Angew. Chem. Int. Ed. Engl., 52:1441-1445 (2013)). Grx1amber11/Ser14 was then expressed in vivo in the presence of either tRNA$^{UTuX\ am}$ or tRNA$^{UTu\ am}$ and purified while Grx1Cys11/Ser14 served as a control. DTNB [5,50-dithiobis-(2-nitrobenzoic acid)] reacts with Cys and Sec residues, while it has no affinity for Ser (Ellman, *Arch. Biochem. Biophys.*, 82:70-77 (1959)). This results in a visible color change, which can be quantified spectroscopically. This reaction was used to determine the Sec insertion ratio in correlation to Grx1Cys11/Ser14. In agreement with the results obtained for $FDH_H$ (FIG. 18A), DTNB treatment of the Grx1amber11/Ser14 gene product synthesized with $tRNA^{UTuX}_{am}$ gave the same colorimetric signal intensity as Grx1Cys11/Ser14; this indicated stoichiometric Sec insertion. In contrast, the Grx1amber11/Ser14 gene product made by the original $tRNA^{UTu}_{am}$ (Aldag, et al., *Angew. Chem. Int. Ed. Engl.*, 52:1441-1445 (2013)) had a weaker signal, exhibiting only 70% of the WT intensity (FIG. 18B). More specifically, relative to WT $tRNA^{Sec}_{op}$, expression of $Grx1_{C11am}$ with $tRNA^{UTuX}$ and $tRNA^{UTu}$ resulted in 99.2±8.4% and 71.2±7.1% DTNB coupling, respectively. This is in line with the earlier finding of 30% misincorporation of Ser (Aldag, et al., *Angew. Chem. Int. Ed. Engl.*, 52:1441-1445 (2013)). These results were confirmed by intact mass Fourier transform ion cyclotron resonance (FT-ICR) mass spectrometry of purified $Grx1_{C11a}$. Peaks at masses of 11018.33 and 11040.31 Da were observed, which correspond to the calculated masses for a Grx1-Sec11-GSH (11019.43) and a Grx1-Sec11-GSH/Na+ adduct (11040.39), respectively. No mass peaks that coincide with a Grx1-Ser11 species were detected.

In vitro protein synthesis has previously been very successful in synthesizing proteins containing non-standard amino acids (Kang, et al., *Biochem. Cell Biol.*, 86:92-99 (2008); Seebeck, et al., *Chem. Commun. (Camb.)*, 47:6141-6143 (2011)). Sec insertion has also been observed in eukaryotic cell free systems (Gupta, et al., *J. Mol. Biol.*, 425:2415-2422 (2013); Mehta, et al., *J. Biol. Chem.*, 279:37852-37859 (2004)), detected as read-though products of a luciferase reporter protein. The capacity of $tRNA^{Sec}$ and the synthetic $tRNA^{UTu}$ to synthesize a natural selenoenzyme was tested by in vitro translation using the PURExpress in vitro translation system (NEB). To achieve Sec insertion, Sec-$tRNA^{Sec}_{am}$ was prepared biochemically and added to the reaction. However, as Sec-$tRNA^{Sec}$ must compete with canonical tRNA for EF-Tu binding, it was believed that a large quantity would be required to mediate translation. Additionally, while translation of *E. coli* $FDH_H$ enabled sensitive colorimetric detection of Sec insertion, the large size of the protein and presence of both molybdenum and iron-sulfur cofactors meant an extended elongation time would likely be required.

Translation reactions were run under anoxic conditions, using a plasmid containing the $fd_{hF140am}$ gene under a T7 promoter to facilitate transcription of $FDH_{H140am}$ mRNA. To eliminate competition for the UAG140 codon, the translation system lacked release factor 1 (PURExpressDRF123 kit, NEB) while including RF2 and RF3, and was supplemented with sodium molybdate, RNase inhibitor, and elongation factor SelB. Using Sec-$tRNA^{Sec}_{am}$, active $FDH_H$ was successfully produced after the standard 2 h reaction time, yet these conditions produced active selenoenzyme only with wild-type Sec-$tRNA^{Sec}$. However, in the absence of SelB but with the addition of an excess of EF-Tu, elevated levels of Sec-tRNA, and a long (5 h) incubation time, all three synthetic tRNA variants ($tRNA^{UTu}_{am}$, $tRNA^{UTuX}_{am}$, and the recently reported $tRNA^{SecUX}_{am}$ (Thyer, et al., *J. Am. Chem. Soc.*, 137:46-49 (2015)) were found to give active $FDH_H$ protein (FIG. 19A). Using the specific activity calculated for WT $FDH_H$, the in vitro yield of active protein under the respective optimal conditions for each tRNA was roughly 34.7 ng using $tRNA^{Sec\ am}$, 47.1 ng using $tRNA^{SecUX}$, 78.7 ng using $tRNA^{UTu}$, and 83.6 ng using $tRNA^{UTuX}$. Thus, each synthetic tRNA produced $FDH_H$ activity similar to both one another and WT $tRNA^{Sec}$.

Although selenocysteine is encoded by UGA in nature, many *E. coli* codons can be reassigned to Sec if the WT UGA codon preceding the SECIS element is replaced by a sense codon (Bröcker, et al., *Angew. Chem. Int. Ed. Engl.*, 53:319-323 (2014)). Using the cell-free selenoprotein synthesis system, the capacity to in vitro recode sense codons in $FDH_H$ to Sec was tested. Mutant genes encoding $fdhF_{140}$GGC, $fdhF_{140}$CGA, $fdhF_{140}$AGG, $fdhF_{140}$ACG, and WT $fdhF_{140}$op were paired with their respective cognate tRNASec mutants, and expressed in vitro in the presence of SelB. While several of these codons did not produce active $FDH_H$ in vivo, all variants tested were found to yield active enzyme in vitro (FIG. 19B) with estimated yields of 5.3 ng using $tRNASec^{GCC}$ ($fdhF_{140}$GGC), 10.9 ng using $tRNA^{Sec}$ UCG ($fdhF_{140}$CGA), 18.4 ng using $tRNA^{Sec\ CCU}$ ($fdhF_{140}$AGG), 2.6 ng using $tRNA^{Sec}$ CGU ($fdhF_{140}$ACG) and 12.8 ng using WT $tRNA^{Sec\ op}$ ($fdhF_{140}$op).

In light of the in vitro recoding capacity of codons AGG and CGA, the activity of these fdhF variants was reinvestigated in vivo. Translation of $fdhF_{140}$AGG and $fdhF_{140}$CGA mRNA, isolation of $FDH_H$, and determination of specific activity showed recoding levels of AGG and CGA to be 65% and 46%, respectively. These results are incorporated in the data shown in FIG. 20A-20B.

The major improvement of $tRNAU^{TuX}$ over $tRNA^{UTu}$ is seen in its ability to be an almost WT $tRNA^{Sec}$-like substrate for SelA ensuring optimal Ser to Sec conversion (FIG. 17). At the same time, $tRNA^{UTuX}$ is a better SerRS substrate than $tRNA^{Sec}$ (Table 2). These properties make $tRNA^{UTuX}$ a very good $tRNA^{UTu}$ molecule for selenoprotein production. Based on similar criteria for elongation and release factor recognition/rejection a different tRNA molecule for canonical Sec insertion was recently selected (Thyer, et al., *J. Am. Chem. Soc.*, 137:46-49 (2015)). As its design began with the WT $tRNA^{Sec}$ scaffold, $tRNA^{SecUX}$ and $tRNA^{UTuX}$ are of different sequence in the D-arm, anticodon stem, variable arm, and T-arm; however, the two tRNAs contain the same important structural parameters for EF-Tu binding (Rudinger, et al., *EMBO J.*, 15:650-657 (1996)). This demonstrates that similar recognition and biological properties can be achieved by different nucleic acid landscapes.

While cell free synthesis of selenoproteins has previously been reported in partially purified components of the eukaryotic pathway (including purified Sec-$tRNA^{Sec}$) (Gupta, et al., *J. Mol. Biol.*, 425:2415-2422 (2013)), an in vitro translation system was established for selenoproteins using commercially available bacterial components. Since protein synthesis quality controls for EF-Tu and SelB are relaxed in this PURExpress translation system, it was foreseen that protein yields would be low. Yet the availability of a sensitive color assay (benzyl-viologen reduction (Lacourciere, et al., *Proc. Natl. Acad. Sci. USA.*, 99:9150-9153 (2002)) encouraged synthesis of $FDH_H$, a selenoprotein whose enzyme activity depends on the presence of Sec, an iron sulfur cluster, and molybdenum as cofactor. The strategy was successful. Addition or co-expression of SelA and SelD (and selenite) may increase Sec-$tRNA^{UTuX}$ yield leading to additional rounds of protein synthesis. In view of the extensive efforts to optimize bacterial cell-free expression systems (Jewett, et al., *Mol. Syst. Biol.*, 4:220 (2008)) and the success of generating Example 13: Selenocysteine Insertion into FDH$_H$ at Positions 8, 11, 15, and 42

Materials and Methods

Amber and Serine mutants were made at position 8, 11, 15 and 42 in E. coli FDH$_H$. Cells were transformed with each mutant variant, along with each of tRNA$^{UTuX}$ (SEQ ID NO:59), tRNA$^{UTu}$ (SEQ ID NO:7), and tRNA$^{SecUX}$ (SEQ ID NO:93). Cells were then plated on benzyl viologen containing media and grown anaerobically, with purple color showing FDH$_H$ activity.

Results tRNA$^{UTu}$ (SEQ ID NO:7), tRNA$^{UTuX}$ (SEQ ID NO:59) and tRNA$^{SecUX}$ (SEQ ID NO:93) are each capable of efficiently inserting selenocysteine into E. coli formate dehydrogenase H (FDH$_H$) at position 140 (Aldag, et al., *Angew. Chem. Int. Ed. Engl.*, 52:1441-1445 (2013), Miller, et al., *FEBS Letters*, (589)2194-2199 (2015), Thyer, et al., *J. Am. Chem. Soc.*, 137:46-49 (2015), and the Examples above). In a side by side comparison, all 3 variants were further shown to mediate insertion of Sec at position 140 in FDH$_H$ using a cell-free translation system (Miller, et al., *FEBS Letters*, (589)2194-2199 (2015) and the Examples above).

The three variants were tested for their capacity to insert selenocysteine into FDH$_H$ at positions 8, 11, 15, and 42. In the WT enzyme, each of these positions contains a cysteine residue, and all four are responsible for coordinating a [4Fe-4S] cluster. Results show that selenocysteine can substitute for Cys at each position, producing active protein, while serine substitution results in loss of activity. As shown in FIG. 21, while all three tRNA variants are capable of inserting Sec at each position, tRNA$^{UTuX}$ mediated insertion resulted in relatively poor activity in this assay; tRNA$^{UTu}$ mediated inserted resulted in relatively moderate activity in this assay, and tRNA$^{SecUX}$ insertion resulted in relatively high activity in this assay. The basis of this difference in Sec insertion capacity is unclear, and contrasts with insertion data at position 140 (Example 12).

We claim:

1. An isolated nucleic acid comprising a nucleic acid sequence encoding a non-naturally occurring tRNA$^{Sec}$, wherein the non-naturally occurring tRNA$^{Sec}$ is recognized by SerRS, when aminoacylated with serine the Ser-tRNA$^{Sec}$ is a substrate for SelA, and when aminoacylated with seleocysteine the Sec-tRNA$^{Sec}$ is recognized by EF-Tu, wherein the non-naturally occurring tRNA$^{Sec}$ comprises at least 80% sequence identity to SEQ ID NO:6, 7, or 8.

2. The isolated nucleic acid of claim 1, wherein the non-naturally occurring tRNA$^{Sec}$ comprises one or more mutations relative to a parent tRNA$^{Sec}$, wherein the parent tRNA$^{Sec}$ is a variant of a naturally occurring E. coli tRNA$^{Ser}$, wherein the acceptor stem of E. coli tRNA$^{Sec}$ is replaced with the acceptor stem of E. coli tRNA$^{Sec}$.

3. The isolated nucleic acid of claim 1, wherein the non-naturally occurring tRNA$^{Sec}$ comprises at least 90% sequence identity to SEQ ID NO:6, 7, or 8.

4. The isolated nucleic acid of claim 1, wherein the non-naturally occurring tRNA$^{Sec}$ exhibits tighter binding with SelA than the tRNA of SEQ ID NO:7, while retaining Ser-tRNA formation by SerRS.

5. The isolated nucleic acid of claim 1, wherein the non-naturally occurring tRNA$^{Sec}$ comprises one or more mutations at positions U8, G9, or A27 in the core region; A14 or G15 in the D-arm; U21 in the D-loop; A52 or U62 in the T-arm; A59 in the T-loop; U44 or G48 in the variable arm; or a combination thereof relative to SEQ ID NO:6, 7, or 8.

6. The isolated nucleic acid of claim 5, wherein the non-naturally occurring tRNA$^{Sec}$ comprises substitutions at U8, G9, and A27 in the core region; substitutions at A14 and G15 in the D-arm; deletion of U21 in the D-loop; substitutions at A52 and U62 in the T-arm; a substitution at A59 in the T-loop; and the insertion of residues 44 and 48 in the variable arm relative to SEQ ID NO:6, 7, or 8.

7. The isolated nucleic acid of claim 6, wherein the non-naturally occurring tRNA$^{Sec}$ comprises the following mutations: U8G, G9U, and A27G in the core region; A14U and G15C in the D-arm; deletion of U21 in the D-loop; A52G and U62C in the T-arm; A59C in the T-loop; and the insertion of residues U44 and G48 in the variable arm relative to SEQ ID NO:6, 7, or 8.

8. The isolated nucleic acid of claim 1, wherein the non-naturally occurring tRNA$^{Sec}$ comprises the backbone of SEQ ID NO:6, 7, or 8, with one or more mutations selected from the group consisting of (i) nucleotide positions 9 and/or 10 remain unchanged or are substituted; (ii) nucleotides 15 and/or 16 remain unchanged or are substituted; (iii) nucleotide 20 remains unchanged or is deleted; (iv) one or both of nucleotides 25 and 26 remain unchanged, one or both of nucleotides 25 and 26 are substituted, a nucleotide is inserted between nucleotides 25 and 26, or a combination thereof; (v) nucleotide 28 remains unchanged or is substituted; (vi) one or two nucleotides are inserted between nucleotides 45 and 46; (vii) one or two nucleotides are inserted between nucleotides 61 and 62; (viii) nucleotide 65 remains the same or is substituted; (ix) nucleotide 72 remains the same or is substituted; (x) nucleotide 75 remains the same or is substituted, or a combination thereof relative to SEQ ID NO:6, 7, or 8.

9. The isolated nucleic acid of claim 1, wherein the non-naturally occurring tRNA$^{Sec}$ comprises the sequence of any one of SEQ ID NO:59-85, or a variant thereof with a substituted anticodon.

10. The isolated nucleic acid of claim 1, wherein the non-naturally occurring tRNA$^{Sec}$ comprises the sequence of SEQ ID NO:59, or a variant thereof with a substituted anticodon.

11. The isolated nucleic acid of claim 1 further comprising a heterologous expression control sequence.

12. An expression vector comprising the isolated nucleic acid of claim 1 operably linked to a heterologous expression control sequence.

13. A host cell comprising the isolated nucleic acid of claim 1.

14. The host cell of claim 13, wherein the host cell is a prokaryote, archaeon, or eukaryote.

15. The host cell of claim 14, wherein the prokaryotic cell is *E. coli*.

16. The host cell of claim 13, wherein the nucleic acid is incorporated into the genome of the cell.

17. The host cell of claim 16, wherein the host cell is a genetically recoded organism.

18. A non-naturally occurring tRNA$^{sec}$ comprising a sequence at least 80% identical to SEQ ID NO:6, 7, or 8, wherein the tRNA$^{sec}$ is recognized by SerRS, when aminoacylated with serine the Ser-tRNA$^{Sec}$ is a substrate for SelA, and when aminoacylated with seleocysteine the Sec-tRNA$^{Sec}$ is recognized by EF-Tu.

19. The non-naturally occurring tRNA$^{sec}$ of claim 18, wherein the tRNA$^{sec}$ exhibits tighter binding with SelA than the tRNA of SEQ ID NO:7, while retaining Ser-tRNA formation by SerRS.

20. A non-naturally occurring tRNA$^{sec}$ comprising the nucleic acid sequence of any one of SEQ ID NO:59-85, or a variant thereof with a substituted anticodon.

* * * * *

SEQUENCE LISTING

<160> NUMBER OF SEQ ID NOS: 93

<210> SEQ ID NO 1
<211> LENGTH: 95
<212> TYPE: RNA
<213> ORGANISM: Escherichia coli

<400> SEQUENCE: 1
ggaagaucgu cgucuccggu gaggcggcug gacuucaaau ccaguugggg ccgccagcgg    60
ucccgggcag guucgacucc ugugaucuuc cgcca    95

<210> SEQ ID NO 2
<211> LENGTH: 93
<212> TYPE: RNA
<213> ORGANISM: Methanococcus maripaludis

<400> SEQUENCE: 2
ggcacggggu gcuuaucuug guagaugagg gcggacuuca gauccgucga guuccguugg    60
aauucggggu ucgauucccc cccugcgccg cca    93

<210> SEQ ID NO 3
<211> LENGTH: 90
<212> TYPE: RNA
<213> ORGANISM: Homo sapiens

<400> SEQUENCE: 3
gcccggauga uccucagugg ucuggggugc aggcuucaaa ccuguagcug ucuagggaca    60
gagugguuca auuccaccuu ucgggcgcca    90

<210> SEQ ID NO 4
<211> LENGTH: 88
<212> TYPE: RNA
<213> ORGANISM: Escherichia coli

<400> SEQUENCE: 4
ggaagugugg ccgagcgguu gaaggcaccg gucuugaaaa ccggcgaccc gaaaggguuc    60
cagaguucga aucucugcgc uuccgcca    88

<210> SEQ ID NO 5

```
<211> LENGTH: 90
<212> TYPE: RNA
<213> ORGANISM: Methanococcus maripaludis

<400> SEQUENCE: 5
gcagaggugg uugagcuugg ccaaaggcgc cggacuugaa auccgguucu ccacugggga    60
gcggggguuc aaaucccucc cucugcgcca                                    90

<210> SEQ ID NO 6
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 6
ggaagaugug gccgagcggu ugaaggcacc ggucuucaaa accggcgacc cgaaagggtu    60
ccagaguucg aaucucugca ucuuccgcca                                    90

<210> SEQ ID NO 7
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 7
ggaagaugug gccgagcggu ugaaggcacc ggucucuaaa accggcgacc cgaaagggtu    60
ccagaguucg aaucucugca ucuuccgcca                                    90

<210> SEQ ID NO 8
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 8
ggaagaugug gccgagcggu ugaaggcacc ggucuuuaaa accggcgacc cgaaagggtu    60
ccagaguucg aaucucugca ucuuccgcca                                    90

<210> SEQ ID NO 9
<211> LENGTH: 88
<212> TYPE: RNA
<213> ORGANISM: Artificial Sequence
<220> FEATURE:
<223> OTHER INFORMATION: Synthetic tRNA

<400> SEQUENCE: 9
ggcacugugg ccgagcgguu gaaggcaccg gucuucaaaa ccggcgaccc gaaaggguuc    60
cagaguucga aucucugcgg ugccgcca                                      88

<210> SEQ ID NO 10
<211> LENGTH: 88
<212> TYPE: RNA
<213> ORGANISM: Artificial Sequence
<220> FEATURE:
<223> OTHER INFORMATION: Synthetic tRNA

<400> SEQUENCE: 10
ggcacugugg ccgagcgguu gaaggcaccg gucucuaaaa ccggcgaccc gaaaggguuc    60
cagaguucga aucucugcgg ugccgcca                                      88
```

<210> SEQ ID NO 11
<211> LENGTH: 88
<212> TYPE: RNA
<213> ORGANISM: Artificial Sequence
<220> FEATURE:
<223> OTHER INFORMATION: Synthetic tRNA

<400> SEQUENCE: 11
ggcacugugg ccgagcgguu gaaggcaccg gucuuuaaaa ccggcgaccc gaaaggguuc    60
cagaguucga aucucugcgg ugccgcca                                      88

<210> SEQ ID NO 12
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 12
gggcacugug gccgagcggu ugaaggcacc ggucuucaaa accggcgacc cgaaaggguu    60
ccagaguucg aaucucugcg gugcccgcca                                    90

<210> SEQ ID NO 13
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 13
ggcacuggug gccgagcggu ugaaggcacc ggucuucaaa accggcgacc cgaaagggu     60 ccagaguucg aaucucugcc ggugccgcca                                    90

<210> SEQ ID NO 14
<211> LENGTH: 88
<212> TYPE: RNA
<213> ORGANISM: Artificial Sequence
<220> FEATURE:
<223> OTHER INFORMATION: Synthetic tRNA

<400> SEQUENCE: 14
ggcacugugg ccgagcgguu gaaggcaccg gucuucaaaa ccggcgaccc gaaaggguuc    60
cugaguucga aucucagcgg ugccgcca                                      88

<210> SEQ ID NO 15
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 15
gggcacuggu ggccgagcgg uugaaggcac cggucuucaa aaccggcgac ccgaaagggu    60
uccagaguuc gaaucucugc cggugcccgc ca                                 92

<210> SEQ ID NO 16
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 16
gggcacugug gccgagcggu ugaaggcacc ggucuucaaa accggcgacc cgaaagggüu      60 ccugaguucg aaucucagcg gugcccgcca                                       90

<210> SEQ ID NO 17
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 17
ggcacuggug gccgagcggu ugaaggcacc ggucuucaaa accggcgacc cgaaagggüu      60 ccugaguucg aaucucagcc ggugccgcca                                       90

<210> SEQ ID NO 18
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 18
gggcacuggu ggccgagcgg uugaaggcac cggucuucaa aaccggcgac ccgaaagggu      60
uccugaguuc gaaucucagc cggugcccgc ca                                    92

<210> SEQ ID NO 19
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 19
gggcacugug gccgagcggu ugaaggcacc ggucucuaaa accggcgacc cgaaagggüu      60 ccagaguucg aaucucugcg gugcccgcca                                       90

<210> SEQ ID NO 20
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 20
ggcacuggug gccgagcggu ugaaggcacc ggucucuaaa accggcgacc cgaaagggüu      60 ccagaguucg aaucucugcc ggugccgcca                                       90

<210> SEQ ID NO 21
<211> LENGTH: 88
<212> TYPE: RNA
<213> ORGANISM: Artificial Sequence
<220> FEATURE:
<223> OTHER INFORMATION: Synthetic tRNA

<400> SEQUENCE: 21
ggcacugugg ccgagcgguu gaaggcaccg gucucuaaaa ccggcgaccc gaaagggüuc      60 cugaguucga aucucagcgg ugccgcca                                         88

<210> SEQ ID NO 22
<211> LENGTH: 92

<212> TYPE: RNA
<213> ORGANISM: Artificial Sequence
<220> FEATURE:
<223> OTHER INFORMATION: Synthetic tRNA

<400> SEQUENCE: 22
gggcacuggu ggccgagcgg uugaaggcac cggucucuaa aaccggcgac ccgaaagggu    60
uccagaguuc gaaucucugc cggugcccgc ca                                 92

<210> SEQ ID NO 23
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 23
gggcacugug gccgagcggu ugaaggcacc ggucucuaaa accggcgacc cgaaagggu u   60 ccugaguucg aaucucagcg gugcccgcca                                    90

<210> SEQ ID NO 24
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 24
ggcacuggug gccgagcggu ugaaggcacc ggucucuaaa accggcgacc cgaaagggu u   60 ccugaguucg aaucucagcc ggugccgcca                                    90

<210> SEQ ID NO 25
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 25
gggcacuggu ggccgagcgg uugaaggcac cggucucuaa aaccggcgac ccgaaagggu    60
uccugaguuc gaaucucagc cggugcccgc ca                                 92

<210> SEQ ID NO 26
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 26
gggcacugug gccgagcggu ugaaggcacc ggucuuuaaa accggcgacc cgaaagggu u   60 ccagaguucg aaucucugcg gugcccgcca                                    90

<210> SEQ ID NO 27
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 27
ggcacuggug gccgagcggu ugaaggcacc ggucuuuaaa accggcgacc cgaaagggu u   60 ccagaguucg aaucucugcc ggugccgcca          90

<210> SEQ ID NO 28
<211> LENGTH: 88
<212> TYPE: RNA
<213> ORGANISM: Artificial Sequence
<220> FEATURE:
<223> OTHER INFORMATION: Synthetic tRNA

<400> SEQUENCE: 28
ggcacugugg ccgagcgguu gaaggcaccg gucuuuaaaa ccggcgaccc gaaagggyuc          60
cugaguucga aucucagcgg ugccgcca          88

<210> SEQ ID NO 29
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 29
gggcacuggu ggccgagcgg uugaaggcac cggucuuuaa aaccggcgac ccgaaagggu          60
uccagaguuc gaaucucugc cggugcccgc ca          92

<210> SEQ ID NO 30
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 30
gggcacugug gccgagcggu ugaaggcacc ggucuuuaaa accggcgacc cgaaagggyu          60
ccugaguucg aaucucagcg gugcccgcca          90

<210> SEQ ID NO 31
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 31
ggcacuggug gccgagcggu ugaaggcacc ggucuuuaaa accggcgacc cgaaagggyu          60
ccugaguucg aaucucagcc ggugccgcca          90

<210> SEQ ID NO 32
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 32
gggcacuggu ggccgagcgg uugaaggcac cggucuuuaa aaccggcgac ccgaaagggu          60
uccugaguuc gaaucucagc cggugcccgc ca          92

<210> SEQ ID NO 33
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 33
ggcgcggugg uugagcuugg ccaaaggcgc cggacuucaa auccgguucu ccacugggga    60
gcggggguuc aaaucccucc cgcgccgcca                                    90

<210> SEQ ID NO 34
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 34
ggcgcggugg uugagcuugg ccaaaggcgc cggacucuaa auccgguucu ccacugggga    60
gcggggguuc aaaucccucc cgcgccgcca                                    90

<210> SEQ ID NO 35
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 35
ggcgcggugg uugagcuugg ccaaaggcgc cggacuuuaa auccgguucu ccacugggga    60
gcggggguuc aaaucccucc cgcgccgcca                                    90

<210> SEQ ID NO 36
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 36
gggcgcggug guugagcuug gccaaaggcg ccggacuuca aauccgguuc uccacugggg    60
agcggggguu caaaucccuc ccgcgcccgc ca                                 92

<210> SEQ ID NO 37
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 37
ggcgcgggug guugagcuug gccaaaggcg ccggacuuca aauccgguuc uccacugggg    60 agcgggggguu caaaucccuc cccgcgccgc ca                                92

<210> SEQ ID NO 38
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 38
ggcgcggugg uugagcuugg ccaaaggcgc cggacuucaa auccgguucu ccacugggga    60 gcgugggguuc aaaucccacc cgcgccgcca                                   90

<210> SEQ ID NO 39

```
<211> LENGTH: 94
<212> TYPE: RNA
<213> ORGANISM: Artificial Sequence
<220> FEATURE:
<223> OTHER INFORMATION: Synthetic tRNA

<400> SEQUENCE: 39
gggcgcgggu gguugagcuu ggccaaaggc gccggacuuc aaauccgguu cuccacuggg    60 gagcggggu ucaaaucccu ccccgcgccc gcca                                  94

<210> SEQ ID NO 40
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 40
gggcgcggug guugagcuug gccaaaggcg ccggacuuca aauccgguuc uccacugggg    60 agcgugggu caaaucccac ccgcgcccgc ca                                    92

<210> SEQ ID NO 41
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 41
ggcgcgggug guugagcuug gccaaaggcg ccggacuuca aauccgguuc uccacugggg    60 agcgugggu caaaucccac cccgcgccgc ca                                    92

<210> SEQ ID NO 42
<211> LENGTH: 94
<212> TYPE: RNA
<213> ORGANISM: Artificial Sequence
<220> FEATURE:
<223> OTHER INFORMATION: Synthetic tRNA

<400> SEQUENCE: 42
gggcgcgggu gguugagcuu ggccaaaggc gccggacuuc aaauccgguu cuccacuggg    60
gagcgugggu caaauccca ccccgcgccc gcca                                  94

<210> SEQ ID NO 43
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 43
gggcgcggug guugagcuug gccaaaggcg ccggacucua aauccgguuc uccacugggg    60 agcggggu caaaucccuc ccgcgcccgc ca                                     92

<210> SEQ ID NO 44
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 44
ggcgcgggug guugagcuug gccaaaggcg ccggacucua aauccgguuc uccacugggg    60
```
agcggggguu caaaucccuc cccgcgccgc ca                                          92

<210> SEQ ID NO 45
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 45
ggcgcggugg uugagcuugg ccaaaggcgc cggacucuaa auccgguucu ccacugggga          60
gcguggguuc aaaucccacc cgcgccgcca                                           90

<210> SEQ ID NO 46
<211> LENGTH: 94
<212> TYPE: RNA
<213> ORGANISM: Artificial Sequence
<220> FEATURE:
<223> OTHER INFORMATION: Synthetic tRNA

<400> SEQUENCE: 46
gggcgcgggu gguugagcuu ggccaaaggc gccggacucu aaauccgguu cuccacuggg          60 gagcggggu ucaaaucccu ccccgcgccc gcca                                        94

<210> SEQ ID NO 47
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 47
gggcgcggug guugagcuug gccaaaggcg ccggacucua aauccgguuc uccacugggg          60
agcguggguu caaacccac ccgcgcccgc ca                                         92

<210> SEQ ID NO 48
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 48
ggcgcgggug guugagcuug gccaaaggcg ccggacucua aauccgguuc uccacugggg          60
agcguggguu caaacccac cccgcgccgc ca                                         92

<210> SEQ ID NO 49
<211> LENGTH: 94
<212> TYPE: RNA
<213> ORGANISM: Artificial Sequence
<220> FEATURE:
<223> OTHER INFORMATION: Synthetic tRNA

<400> SEQUENCE: 49
gggcgcgggu gguugagcuu ggccaaaggc gccggacucu aaauccgguu cuccacuggg          60
gagcgugggu ucaaauccca ccccgcgccc gcca                                       94

<210> SEQ ID NO 50
<211> LENGTH: 92
<212> TYPE: RNA
<213> ORGANISM: Artificial Sequence
<220> FEATURE:

<223> OTHER INFORMATION: Synthetic tRNA

<400> SEQUENCE: 50
gggcgcggug guugagcuug gccaaaggcg ccggacuuua aauccgguuc uccacugggg    60
agcggggguu caaaucccuc ccgcgcccgc ca    92

<210> SEQ ID NO 51
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 51
ggcgcgggug guugagcuug gccaaaggcg ccggacuuua aauccgguuc uccacugggg    60
agcggggguu caaaucccuc cccgcgccgc ca    92

<210> SEQ ID NO 52
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 52
ggcgcggugg uugagcuugg ccaaaggcgc cggacuuuaa auccgguucu ccacgggga    60 gcguggguuc aaaucccacc cgcgccgcca    90

<210> SEQ ID NO 53
<211> LENGTH: 94
<212> TYPE: RNA
<213> ORGANISM: Artificial Sequence
<220> FEATURE:
<223> OTHER INFORMATION: Synthetic tRNA

<400> SEQUENCE: 53
gggcgcgggu gguugagcuu ggccaaaggc gccggacuuu aaauccgguu cuccacuggg    60 gagcggggu ucaaauccou ccccgcgccc gcca    94

<210> SEQ ID NO 54
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 54
gggcgcggug guugagcuug gccaaaggcg ccggacuuua aauccgguuc uccacugggg    60
agcguggguu caaaucccac ccgcgcccgc ca    92

<210> SEQ ID NO 55
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 55 gggcgcgggug guugagcuug gccaaaggcg ccggacuuua aauccgguuc uccacugggg    60 agcgugggu caaaucccac ccgcgccgc ca    92

```
<210> SEQ ID NO 56
<211> LENGTH: 94
<212> TYPE: RNA
<213> ORGANISM: Artificial Sequence
<220> FEATURE:
<223> OTHER INFORMATION: Synthetic tRNA

<400> SEQUENCE: 56
gggcgcgggu gguugagcuu ggccaaaggc gccggacuuu aaauccgguu cuccacuggg      60
gagcgugggu ucaaauccca ccccgcgccc gcca                                 94

<210> SEQ ID NO 57
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 57
ggcgcggugg uugagcuugg ccaaaggcgc cggacuugaa auccgguucu ccacugggga      60
gcggggguuc aaaucccucc cgcgccgcca                                      90

<210> SEQ ID NO 58
<211> LENGTH: 88
<212> TYPE: RNA
<213> ORGANISM: Artificial Sequence
<220> FEATURE:
<223> OTHER INFORMATION: Synthetic tRNA

<400> SEQUENCE: 58
ggcacugugg ccgagcgguu gaaggcaccg gucuugaaaa ccggcgaccc gaaagggguuc    60 cagaguucga aucucugcgg ugccgcca                                        88

<210> SEQ ID NO 59
<211> LENGTH: 91
<212> TYPE: RNA
<213> ORGANISM: Artificial Sequence
<220> FEATURE:
<223> OTHER INFORMATION: synthetic polynucleotide - tRNA

<400> SEQUENCE: 59
ggaagauggu gccguccggu gaaggcgccg gucucuaaaa ccggucgacc cgaaaggguu      60
cgcaggguuc gacucccugc aucuuccgcc a                                    91

<210> SEQ ID NO 60
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 60
ggaagauggu gccgagcggu ugaaggcgcc ggucucuaaa accggcgacc cgaaaggguu      60
ccagaguucg aaucucugca ucuuccgcca                                      90

<210> SEQ ID NO 61
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 61
```

```
ggaagaugug gccgagcggu ugaaggcgcc ggucucuaaa accggcgacc cgaaagggu    60 ccaggguucg acucccugca ucuuccgcca                                     90
```

<210> SEQ ID NO 62
<211> LENGTH: 89
<212> TYPE: RNA
<213> ORGANISM: Artificial Sequence
<220> FEATURE:
<223> OTHER INFORMATION: synthetic polynucleotide - tRNA

<400> SEQUENCE: 62

```
ggaagauggu gccguccggu gaaggcgccg gucucuaaaa ccggcgaccc gaaaggguuc    60
caggguucga cucccugcau cuuccgcca                                      89
```

<210> SEQ ID NO 63
<211> LENGTH: 93
<212> TYPE: RNA
<213> ORGANISM: Artificial Sequence
<220> FEATURE:
<223> OTHER INFORMATION: synthetic polynucleotide - tRNA

<400> SEQUENCE: 63

```
ggaagauggu gccguccggu gaaggcgccg gucucuaaaa ccgguucgac ccgaaagggu    60
ucggcagggu ucgacucccu gcaucuuccg cca                                 93
```

<210> SEQ ID NO 64
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 64

```
ggaagaugug gccgagcggu ugaaggcgcc ggucucuaaa accggcgacc cgaaagggu    60 ccaggguucg auucccugca ucuuccgcca                                     90
```

<210> SEQ ID NO 65
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 65

```
ggaagauggu gccguccggu ugaaggcgcc ggucucuaaa accggcgacc cgaaagggu    60 ccagaguucg aaucucugca ucuuccgcca                                     90
```

<210> SEQ ID NO 66
<211> LENGTH: 89
<212> TYPE: RNA
<213> ORGANISM: Artificial Sequence
<220> FEATURE:
<223> OTHER INFORMATION: synthetic polynucleotide - tRNA

<400> SEQUENCE: 66

```
ggaagauggu gccguccggu gaaggcgccg gucucuaaaa ccgcgaccc gaaaggguuc     60 caggguucga uucccugcau cuuccgcca                                      89
```

<210> SEQ ID NO 67
<211> LENGTH: 91
<212> TYPE: RNA
<213> ORGANISM: Artificial Sequence

```
<220> FEATURE:
<223> OTHER INFORMATION: synthetic polynucleotide - tRNA

<400> SEQUENCE: 67
ggaagauggu gccguccggu gaaggcgccg gucucuaaaa ccggucgacc cgaaaggguu    60
cgcaggguuc gauucccugc aucuuccgcc a                                  91

<210> SEQ ID NO 68
<211> LENGTH: 91
<212> TYPE: RNA
<213> ORGANISM: Artificial Sequence
<220> FEATURE:
<223> OTHER INFORMATION: synthetic polynucleotide - tRNA

<400> SEQUENCE: 68
ggaagauggu gccguccggu gaaggcgccg gucuucaaaa ccggucgacc cgaaaggguu    60
cgcaggguuc gacucccugc aucuuccgcc a                                  91

<210> SEQ ID NO 69
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 69
ggaagauggu gccgagcggu ugaaggcgcc ggucuucaaa accggcgacc cgaaaggguu    60
ccagaguucg aaucucugca ucuuccgcca                                    90

<210> SEQ ID NO 70
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 70
ggaagaugug gccgagcggu ugaaggcgcc ggucuucaaa accggcgacc cgaaaggguu    60
ccaggguucg acucccugca ucuuccgcca                                    90

<210> SEQ ID NO 71
<211> LENGTH: 89
<212> TYPE: RNA
<213> ORGANISM: Artificial Sequence
<220> FEATURE:
<223> OTHER INFORMATION: synthetic polynucleotide - tRNA

<400> SEQUENCE: 71
ggaagauggu gccguccggu gaaggcgccg gucuucaaaa ccggcgaccc gaaaggguuc    60
caggguucga cucccugcau cuuccgcca                                     89

<210> SEQ ID NO 72
<211> LENGTH: 93
<212> TYPE: RNA
<213> ORGANISM: Artificial Sequence
<220> FEATURE:
<223> OTHER INFORMATION: synthetic polynucleotide - tRNA

<400> SEQUENCE: 72
ggaagauggu gccguccggu gaaggcgccg gucuucaaaa ccgguucgac cgaaagggu     60 ucggcagggu ucgacucccu gcaucuuccg cca                                93
```

<210> SEQ ID NO 73
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 73
ggaagaugug gccgagcggu ugaaggcgcc ggucuucaaa accggcgacc cgaaagggu    60 ccaggguucg auucccugca ucuuccgcca                                    90

<210> SEQ ID NO 74
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 74
ggaagauggu gccguccggu ugaaggcgcc ggucuucaaa accggcgacc cgaaagggu    60 ccagaguucg aaucucugca ucuuccgcca                                    90

<210> SEQ ID NO 75
<211> LENGTH: 89
<212> TYPE: RNA
<213> ORGANISM: Artificial Sequence
<220> FEATURE:
<223> OTHER INFORMATION: synthetic polynucleotide - tRNA

<400> SEQUENCE: 75
ggaagauggu gccguccggu gaaggcgccg gucuucaaaa ccggcgaccc gaaagggug    60 caggguucga uucccugcau cuuccgcca                                     89

<210> SEQ ID NO 76
<211> LENGTH: 91
<212> TYPE: RNA
<213> ORGANISM: Artificial Sequence
<220> FEATURE:
<223> OTHER INFORMATION: synthetic polynucleotide - tRNA

<400> SEQUENCE: 76
ggaagauggu gccguccggu gaaggcgccg gucuucaaaa ccggucgacc cgaaagggu    60 cgcaggguuc gauucccugc aucuuccgcc a                                  91

<210> SEQ ID NO 77
<211> LENGTH: 91
<212> TYPE: RNA
<213> ORGANISM: Artificial Sequence
<220> FEATURE:
<223> OTHER INFORMATION: synthetic polynucleotide - tRNA

<400> SEQUENCE: 77
ggaagauggu gccguccggu gaaggcgccg gucuuaaaa ccggucgacc cgaaagggu     60 cgcaggguuc gacucccugc aucuuccgcc a                                  91

<210> SEQ ID NO 78
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 78
ggaagauggu gccgagcggu ugaaggcgcc ggucuuaaaa accggcgacc cgaaagggu    60 ccagaguucg aaucucugca ucuuccgcca                                    90

<210> SEQ ID NO 79
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 79
ggaagaugug gccgagcggu ugaaggcgcc ggucuuaaaa accggcgacc cgaaagggu    60 ccagguucg acucccugca ucuuccgcca                                     90

<210> SEQ ID NO 80
<211> LENGTH: 89
<212> TYPE: RNA
<213> ORGANISM: Artificial Sequence
<220> FEATURE:
<223> OTHER INFORMATION: synthetic polynucleotide - tRNA

<400> SEQUENCE: 80
ggaagauggu gccguccggu gaaggcgccg gucuuuaaaa ccggcgaccc gaaagggnuc    60
caggguucga cucccugcau cuuccgcca                                     89

<210> SEQ ID NO 81
<211> LENGTH: 93
<212> TYPE: RNA
<213> ORGANISM: Artificial Sequence
<220> FEATURE:
<223> OTHER INFORMATION: synthetic polynucleotide - tRNA

<400> SEQUENCE: 81
ggaagauggu gccguccggu gaaggcgccg gucuuuaaaa ccgguucgac ccgaaagggu    60
ucggcagggu ucgacucccu gcaucuuccg cca                                93

<210> SEQ ID NO 82
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 82
ggaagaugug gccgagcggu ugaaggcgcc ggucuuaaaa accggcgacc cgaaagggu    60 caggguucg auucccugca ucuuccgcca                                     90

<210> SEQ ID NO 83
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 83
ggaagauggu gccguccggu ugaaggcgcc ggucuuaaaa accggcgacc cgaaagggu    60 ccagaguucg aaucucugca ucuuccgcca                                    90

<210> SEQ ID NO 84
<211> LENGTH: 89
<212> TYPE: RNA

```
<213> ORGANISM: Artificial Sequence
<220> FEATURE:
<223> OTHER INFORMATION: synthetic polynucleotide - tRNA

<400> SEQUENCE: 84
ggaagauggu gccguccggu gaaggcgccg gucuuuaaaa ccggcgaccc gaaagggguuc    60 caggguucga uucccugcau cuuccgcca                                      89

<210> SEQ ID NO 85
<211> LENGTH: 91
<212> TYPE: RNA
<213> ORGANISM: Artificial Sequence
<220> FEATURE:
<223> OTHER INFORMATION: synthetic polynucleotide - tRNA

<400> SEQUENCE: 85
ggaagauggu gccguccggu gaaggcgccg gucuuuaaaa ccggucgacc cgaaagggguu    60 cgcaggguuc gauucccugc aucuuccgcc a                                   91

<210> SEQ ID NO 86
<211> LENGTH: 89
<212> TYPE: RNA
<213> ORGANISM: Artificial Sequence
<220> FEATURE:
<223> OTHER INFORMATION: synthetic polynucleotide - tRNA

<400> SEQUENCE: 86
ggaagauggu gccguccggu gaaggcgccg gucucuaaaa ccggcgaccc gaaagggguuc    60 cagaguucga aucucugcau cuuccgcca                                      89

<210> SEQ ID NO 87
<211> LENGTH: 92
<212> TYPE: RNA
<213> ORGANISM: Artificial Sequence
<220> FEATURE:
<223> OTHER INFORMATION: synthetic polynucleotide - tRNA

<400> SEQUENCE: 87
ggaagaugug gccgagcggu ugaaggcgcc ggucucuaaa accggucgac cgaaagggu     60 ucgcagaguu cgaaucucug caucuuccgc ca                                  92

<210> SEQ ID NO 88
<211> LENGTH: 94
<212> TYPE: RNA
<213> ORGANISM: Artificial Sequence
<220> FEATURE:
<223> OTHER INFORMATION: synthetic polynucleotide - tRNA

<400> SEQUENCE: 88
ggaagaugug gccgagcggu ugaaggcgcc ggucucuaaa accgguucga cccgaaaggg    60
uucggcagag uucgaaucuc ugcaucuucc gcca                                94

<210> SEQ ID NO 89
<211> LENGTH: 92
<212> TYPE: RNA
<213> ORGANISM: Artificial Sequence
<220> FEATURE:
<223> OTHER INFORMATION: synthetic polynucleotide - tRNA

<400> SEQUENCE: 89
ggaagauggu gcucgagcgg uugaagggcg ccggucucua aaaccggcga cccgaaaggg    60
uuccagaguu cgaaucucug caucuuccgc ca                                  92
```

```
<210> SEQ ID NO 90
<211> LENGTH: 90
<212> TYPE: RNA
<213> ORGANISM: Artificial Sequence
<220> FEATURE:
<223> OTHER INFORMATION: synthetic polynucleotide - tRNA

<400> SEQUENCE: 90
ggaagauggu gccgugcggu ugaaggcgcc ggucucuaaa accggcgacc cgaaaggguu      60
ccagaguucg aaucucugca ucuuccgcca                                      90

<210> SEQ ID NO 91
<211> LENGTH: 94
<212> TYPE: RNA
<213> ORGANISM: Artificial Sequence
<220> FEATURE:
<223> OTHER INFORMATION: synthetic polynucleotide - tRNA

<400> SEQUENCE: 91
ggaagauggu gcugcgagcg guugaagcgg cgccggucuc uaaaaccggc gacccgaaag      60
gguuccagag uucgaaucuc ugcaucuucc gcca                                 94

<210> SEQ ID NO 92
<211> LENGTH: 93
<212> TYPE: RNA
<213> ORGANISM: Artificial Sequence
<220> FEATURE:
<223> OTHER INFORMATION: synthetic polynucleotide - tRNA

<400> SEQUENCE: 92
ggaagauggu gccguccggu gaaggcgccg gucucuaaaa ccgguucgac ccgaaagggu      60
ucggcagggu ucgauucccu gcaucuuccg cca                                  93

<210> SEQ ID NO 93
<211> LENGTH: 95
<212> TYPE: RNA
<213> ORGANISM: Artificial Sequence
<220> FEATURE:
<223> OTHER INFORMATION: synthetic polynucleotide - tRNA

<400> SEQUENCE: 93
ggaagauggu cgucuccggu gaggcggcug gacucuaaau ccaguugggg ccgccagcgg      60
ucccggucag guucgacucc uugcaucuuc cgcca                                95
```